US012171748B2

(12) United States Patent
Xiao et al.

(10) Patent No.: US 12,171,748 B2
(45) Date of Patent: Dec. 24, 2024

(54) NITROIMIDAZOLE FORMULATIONS

(71) Applicant: IRP Health Pty Ltd, Mount Waverly (AU)

(72) Inventors: Zhicheng Xiao, Langwarrin (AU); David Xiang Yu, Frankston South (AU); Colin William Pouton, Alphington (AU); Zhiyong He, Pakenham (AU)

(73) Assignee: IRP HEALTH PTY LTD, Mount Waverly (AU)

( * ) Notice: Subject to any disclaimer, the term of this patent is extended or adjusted under 35 U.S.C. 154(b) by 813 days.

(21) Appl. No.: 17/059,378

(22) PCT Filed: May 29, 2019

(86) PCT No.: PCT/AU2019/050531
§ 371 (c)(1),
(2) Date: Nov. 27, 2020

(87) PCT Pub. No.: WO2019/227149
PCT Pub. Date: Dec. 5, 2019

(65) Prior Publication Data
US 2021/0220335 A1    Jul. 22, 2021

(30) Foreign Application Priority Data

May 29, 2018   (AU) .................... 2018901902

(51) Int. Cl.
| A61K 31/4164 | (2006.01) |
| A23K 20/121 | (2016.01) |
| A23K 20/137 | (2016.01) |
| A23K 20/195 | (2016.01) |
| A23K 50/30 | (2016.01) |
| A23L 33/00 | (2016.01) |
| A23L 33/10 | (2016.01) |
| A61K 9/00 | (2006.01) |
| A61K 31/4375 | (2006.01) |
| A61P 31/04 | (2006.01) |

(52) U.S. Cl.
CPC ........ *A61K 31/4164* (2013.01); *A23K 20/121* (2016.05); *A23K 20/137* (2016.05); *A23K 20/195* (2016.05); *A23K 50/30* (2016.05); *A23L 33/127* (2016.08); *A23L 33/40* (2016.08); *A61K 9/0056* (2013.01); *A61K 31/4375* (2013.01); *A61P 31/04* (2018.01); *A23V 2002/00* (2013.01)

(58) Field of Classification Search
CPC . A61K 31/4164; A23K 20/137; A23L 33/127; A61P 31/04; A23V 2002/00
See application file for complete search history.

(56) References Cited

U.S. PATENT DOCUMENTS

| 3,715,433 A | 2/1973 | Roche |
| 6,280,768 B1 | 8/2001 | McDevitt |
| 2009/0324801 A1 | 12/2009 | Lopez De Hierro et al. |
| 2015/0196029 A1 | 7/2015 | Amelotti et al. |
| 2017/0037043 A1 | 2/2017 | Liu |

FOREIGN PATENT DOCUMENTS

| CN | 101032564 A | 9/2007 | |
| CN | 102318745 A | 1/2012 | |
| CN | 102327426 A | * 1/2012 | |
| CN | 102813928 A | * 12/2012 | |
| CN | 105641337 A | 6/2016 | |
| CN | 105961851 A | 9/2016 | |
| CN | 107753524 A | 3/2018 | |
| CN | 107875206 A | 4/2018 | |
| DE | 202013011160 U1 | * 6/2014 | ......... A61K 31/4164 |
| EP | 1905436 A1 | 4/2008 | |
| GB | 1459339 A | 12/1976 | |
| KR | 10-2016-0102857 A | 8/2016 | |
| WO | 02/21933 A2 | 3/2002 | |

(Continued)

OTHER PUBLICATIONS

Huang. Molecular and Clinical Characteristics of Clostridium difficile Infection in a University Hospital in Shanghai, China, (Clinical Infectious Diseases), Dec. 2008, pp. 1606-1608, [online], [retrieved on Sep. 14, 2023]. Retrieved from the internet <URL: https://academic.oup.com/cid/article (Year: 2008).*

Zhi.Berberine Blocks the Relapse of Clostridium difficile Infection in C57BL/6 Mice after Standard Vancomycin Treatment, ( Antimicrobial Agents and Chemotherapy), Jun. 2015, vol. 59, [online],[retrieved on Oct. 2, 2023]. Retrieved from the internet <URL: https://journals.asm.org/doi/full/10.1128/a (Year: 2015).*

Keessen et al. Clostridium difficile Infection Associated with Pig Farms, (Emerging Infectious Diseases), Jun. 2013, pp. 1032-1034, [online], [retrieved on Oct. 19, 2023]. Retrieved from the internet <URL: Clostridium difficile Infection Associated with Pig Farms—PMC (nih.gov) > (Year: 2013).*

(Continued)

*Primary Examiner* — Sarah Pihonak
*Assistant Examiner* — Mikhail O'Donnel Robinson
(74) *Attorney, Agent, or Firm* — HOLLAND & HART LLP

(57) ABSTRACT

The disclosure relates to nitroimidazoles and related compounds and derivatives, formulations thereof, and their use in the prevention and/or treatment of infectious disease in animals. In particular, the disclosure relates to 5-nitroimidazoles and related compounds and derivatives, formulations thereof, and their use in the prevention and/or treatment of infectious disease in animals including bacterial, viral, parasitic or fungal infections. More particularly, the invention relates to metronidazole and related compounds and derivatives, formulations thereof, and their use in the prevention and/or treatment of infectious disease caused by *Clostridium* species. Most preferably, the nitroimidazole is metronidazole administered in combination with berberine, or a berberine alkaloid, in a synergistic weight ratio of 1:1 or 1:2.

9 Claims, 14 Drawing Sheets

(56) References Cited

FOREIGN PATENT DOCUMENTS

| WO | 2007/034009 A2 | 3/2007 |
|---|---|---|
| WO | 2015/065983 A1 | 5/2015 |
| WO | 2016/015634 A1 | 2/2016 |
| WO | 2017/142895 A1 | 8/2017 |

OTHER PUBLICATIONS

Of Huang et al. Molecular and Clinical Characteristics of Clostridium difficile Infection in a University Hospital in Shanghai, China, ( Clinical Infectious Diseases), Dec. 2008, pp. 1606-1608 (Year: 2008).*
"Firming Night Cream", Mintel GNPD, Obtained from the Internet, <URL: http://www.gnpd.com/sinatra/recordpage/4788207/>, Last Retreived Apr. 17, 2018, Published May 2017.
"Improved Liquid Soft Gels", Mintel GNPD, Obtained from the Internet, <URL: http://www.gnpd.com/sinatra/recordpage/10248500/>, Last Retreived May 8, 2018, Published Jan. 2006.
"International Search Report and Written Opinion of the International Searching Authority," issued in connection with Int'l Appl. No. PCT/AU2019/050531 dated Jul. 15, 2019 (18 pages).
"New Tesmin Capsule", Mintel GNPD, Obtained from the Internet, <URL: http://www.gnpd.com/sinatra/recordpage/609437/>, Last Retreived May 8, 2018, Published Nov. 2006.
"Official Title: A Randomized, Open Label, Active Control, Safety, Tolerability and Pharmacokinetics Study of Two Dr. Reddy's Formulations of Metronidazole Versus Immediate Release Metronidazole (Flagyl) in Patients With Mild to Moderate C. Difficile Associated Diarrhea (CDAD)", NCT01559545, ClincalTrials.Gov, Obtained from the Internet, <URL: https://clinicaltrials.gov /ct2/show/ NCT01559545>.
"Official Title: Addition of a Probiotic (Lactobacillus GG) to Metronidazole for the Treatment of Clostridium Difficile Associated Disease", NCT00304863, ClinicalTrials. Gov, Obtained from the Internet, <URL: https://clinicaltrials.gov/ct2/show/NCT00304863>.
"Official Title: Efficacy of Metronidazole Prophylaxis Against Clostridium Difficile-Associated Diarrhea in High Risk Adult Patients: A Randomized Clinical Trial", NCT02200328, ClinicalT rials.Gov, Obtained from the Internet, <URL: https://clinicaltrials.gov/ct2/show/study/NCT02200328>.
"Stomach Tablets", Mintel GNPD, Obtained from the Internet, <URL: http://www.gnpd.com/sinatra/recordpage/143272/>, Last Retreived May 8, 2018, Published Apr. 2002.
"Turmeric/Boswellia Complex Herbal Supplement Tablets", Mintel GNPD, Obtained from the Internet, <http://www.gnpd.com/sinatra/recordpage/1251324/>, Last Reteived May 7, 2018, Published Jan. 2010.
"Whole Body Healthy Inflammation Response Dietary Supplement", Mintel GNPD, Obtained from the Internet, <URL: http://www.gnpd.com/sinatra/recordpage/2512819/>, Last Retrieved Apr. 17, 2018, Published Jun. 2014.
Berge, S. M. et al., "Pharmaceutical salts", Journal of Pharmaceutical Science, vol. 66, No. 1, 1977, 1-19.
Brown, "Antibiotic resistance breakers: can repurposed drugs fill the antibiotic discovery void?", Nature Reviews Drug Discovery, vol. 14, No. 12, (2015), pp. 821-832.
Brunton, L. L., et al., Goodman & Gilman's, The Pharmacological Basis of Therapeutics, 2005.
Chakraborty et al., "Berberine Hydrochloride Could Prove to Be a Promising Bullet Against Clostridium Difficile Infection: A Preliminary Study from South India", Asian Journal of Pharmaceutical and Clinical Research, vol. 10, No. 12, Jan. 1, 2017, pp. 419-424.
De Pablos et al, "Anticoccidial activity of maslinic acid against infection with Eimeria tenella in chickens", Parasitology Research (2010), vol. 107, No. 3, pp. 601-604.
Dr. Reddy's Laboratories Limited: A Safety, Tolerability and Pharmacokinetic Study of Two Formulations of Metronidazole Versus Immediate Release Metronidazole in Patient With C. Difficile Colitis, ClincalTrials.Gov, May 22, 2018, XP009524502.

Edward, D. I., et al., "Nitroimidazole drugs-action and resistance mechanisms I. Mechanism of action", Journal of Antimicrobial Chemotherapy, vol. 31, No. 1, Jan. 1993, pp. 9-20.
European Patent Office, "Supplementary European search report and Search Opinion", issued in connection with European Patent Application No. 19811375.5 dated Feb. 9, 2022, 6 pages.
Fang, et al., "Synthesis and biological activities of novel amine-derived bis-azoles as potential antibacterial and antifungal agents", European Journal of Medicinal Chemistry, 2010, vol. 45, No. 9, pp. 4388-4398.
Gould, P. L., et al., "Salt selection for basic drugs", International Journal of Pharmaceutics, vol. 33 No. (1-3), 1986, pp. 201-217.
Huang et al., "Molecular and Clinical Characteristics of Clostridium difficile Infection in a University Hospital in Shanghai, China", Clinical Infectious Diseases, vol. 47, No. 12, (2008), pp. 1606-1608.
Kalani et al, "In Vitro, In Silico and In Vivo Studies of Ursolic Acid as an Anti-Filarial Agent", PLoS One, vol. 9, No. 1, Nov. 6, 2014, 13 pages.
Kapoor, V. K., et al., "Medicinal Significance of Nitroimidazoles—Some Recent Advances", Journal of Scientific & Industrial Research, vol. 62, 2003, pp. 659-665.
Kim, P. et al., "Structure-activity relationships of antitubercular nitroimidazoles. I. Structural features associated with aerobic and anaerobic activities of 4- and 5-nitroimidazoles", J. Med. Chem., vol. 52, No. 5, pp. 1317-1328.
Kyne, Dr L., et al. "Association between antibody response to toxin A and protection against recurrent Clostridium difficile diarrhoea", Lancet, vol. 357, No. 9251, pp. 189-193.
Kyne, L. et al., "Asymptomatic carriage of Clostridium difficile and serum levels of IgG antibody against toxin A", N. Engl. J. Med., vol. 342, Feb. 10, 2000, 390-397.
Lv et al, "Berberine Blocks the Relapse of Clostridium difficile Infection in C57BL/6 Mice after Standard Vancomycin Treatment", Antimicrobial Agents and Chemotherapy, vol. 59, No. 7, (2015), pp. 3726-3735.
Magi, G., et al., "Antimicrobial activity of essential oils and carvacrol, and synergy of carvacrol and erythromycin, against clinical, erythromycin-resistant Group A *Streptococci*", Front Microbiol., vol. 6, 2015.
Malik, T. A., et al, "In vivo anticoccidial activity of berberine [18,5,6-dihydro-9,10-dimethoxybenzo(g)-1,3-benzodioxolo(5,6-a) quinolizinium]—An isoquinoline alkaloid present in the root bark of Berberis lyceum", Phytomedicine vol. 21, No. 5, 2014, pp. 663-669.
Malik, T. A., et al, "Synergistic approach for treatment of chicken coccidiosis using berberine—A plant natural product", Microbial Pathogenesis, vol. 93, Apr. 2016, pp. 56-62.
Martin, J. S. H., et al, "Clostridium difficile infection: epidemiology, diagnosis and understanding transmission", nature reviews gastroenterology & hepatology, vol. 13, 2016, pp. 206-216.
Martins, T. A. F. et al, "Benznidazole/Itraconazole Combination Treatment Enhances Anti-Trypanosoma cruzi Activity in Experimental Chagas Disease", PLoS One, vol. 10, No. 6, 2015 , Pages. 12 Pages.
Mathias, F. et al., "An Efficient One-Pot Catalyzed Synthesis of 2,4-Disubstituted 5-Nitroimidazoles Displaying Antiparasitic and Antibacterial Activities" Molecules, vol. 22 No 8, 2017, pp. 1278.
Merrigan., M, et al., "Human Hypervirulent Clostridium difficile Strains Exhibit Increased Sporulation as Well as Robust Toxin Production", Journal of Bacteriology, vol. 192, No. 19, 2010, pp. 4904-4911.
Mingo, E., et al, "Selective antibacterial effect on Campylobacter of a winemaking waste extract (WWE) as a source of active phenolic compounds", Food Science and Technology vol. 68, 2016, pp. 418-424.
Minns, L. A., et al., "A Novel Triterpenoid Induces Transforming Growth Factor Production by Intraepithelial Lymphocytes to Prevent Ileitis", Gastroenterology, vol. 127, No. 1, pp. 119-126.
Mital, A., et al., "Synthetic Nitroimidazoles: Biological Activity and Mutagenicity Relationship", Scientia Pharmaceutica, vol. 77, No. 3, 2009, pp. 497-520.

(56) References Cited

OTHER PUBLICATIONS

Miyamoto, Y., et al., "Expanded therapeutic potential in activity space of next-generation 5-nitroimidazole antimicrobials with broad structural diversity", Proc. Natl. Acad. Sci., vol. 110, No. 43, Oct. 7, 2013, pp. 17564-17569.

Muthamilselvan et al, "Herbal Remedies for Coccidiosis Control: A Review of Plants, Compounds, and Anticoccidial Actions", Evidence-Based Complementary and Alternative Medicine, vol. 2016, Article ID 2657981, Jan. 22, 2016, 19 Pages.

Rowe, R.C., Handbook of Pharmaceutical Excipients, 6th Ed., Pharmaceutical Press and American Pharmacists Association, 2009.

Sambol, S. P., et al., "Colonization for the Prevention of Clostridium difficile Disease in Hamsters", The Journal of Infectious Diseases, vol. 186, Issue 12, Dec. 15, 2002, pp. 1781-1789.

Stella, V. J. et al., "Prodrugs Do They Have Advantages in Clinical Practice?", Drugs, vol. 29, 1985, pp. 455-473.

Upcroft, J. A., et al., "5-Nitroimidazole Drugs Effective against Metronidazole-Resistant Trichomonas vaginalis and Giardia duodenalis", Antimicrobial Agents and Chemotherapy, vol. 50, No. 1, Jan. 2006, pp. 344-347.

Warny, M., et al., "Human antibody response to Clostridium difficile toxin A in relation to clinical course of infection", Infect Immun., vol. 62, No. 2, Feb. 1, 1994, pp. 384-389.

Weina, M., et al., "Berberine inhibits the proliferation and migration of breast cancer ZR-75-30 cells by targeting Ephrin-B2", Phytomedicine, vol. 25, Feb. 2017, pp. 45-51.

Xiang et al, "Four New Prenylated Isoflavonoids in Tadehagi triquetrum", Journal of Agricultural and Food Chemistry vol. 53, No. 2, 2005, pp. 267-271.

Xu et al, "Inhibitory effects of berberine on the activation and cell cycle progression of human peripheral lymphocytes", Cellular & Molecular Immunology, vol. 2, No. 4, Aug. 2005, pp. 295-300.

Xu, Shaohua, In Vitro/Vivo Activity of Berberine with or without Vancomycin against Clinical Isolates of Toxin-Producing Clostridium difficile, «Chinese Master's Theses Full-text Database Medicine and Health Sciences», No. 04, 2016, E060-60.

Zhang, L. et al., "Synthesis and bioactive evaluation of novel hybrids of metronidazole and berberine as new type of antimicrobial agents and their transportation behavior by human serum albumin", Bioorganic & Medicinal Chemistry, vol. 21, No. 14, pp. 4158-4169.

"3 Day Weekend Body", Mintel GNPD, Obtained from the Internet, <URL: http://www.gnpd.com/sinatra/recordpage/1809870/>, Last Retreived Apr. 19, 2018, Published May 2012.

"Cream", Mintel GNPD, Obtained from the Internet, <URL: http://www.gnpd.com/sinatra/recordpage/1917931/>, Last Retrieved Apr. 23, 2018, Published Oct. 2012.

AH3/4546, "Masroodeetoos", Traditional Knowledge Digital Library, Obtained from the Internet, <URL: http://www.tkdl.res.in/tkdl/LangDefault/Formulation/Member_Docs/BC/unani/highlight.asp?a=/tkdl/langdefault/formulation/member_docs/bc/unani/ah3-4546.asp&b=indian%20frankincense%20and%20infection&c=T&stypePrint=GLOBAL-SIMPLE-SEARCH?str=Global>, Last Retrieved May 14, 2018.

\* cited by examiner

Fibrauretin (palmatine)

Palmatine chloride

Matrine

Oxymatrine

Arecoline

Arecoline hydrobromide

Baicalin

Baicalein

Anemonin

Andrographolide (Ia)

azyomycin misonidazole benzindazole secnidazole ornidazole (Ic)

ipronidazole ronidazole

"MF" nitroimidazole

"MCA" nitroimidazole

R = H fexinidazole
R = CH₃ azanidazole sulphimidazole 5-nitromegazol

R = 5-Cl-thiophen-2-yl

NITROIMIDAZOLE FORMULATIONS

CROSS REFERENCE TO RELATED APPLICATIONS

This application is a U.S. National Entry and claims priority to PCT International Patent Application No. PCT/AU2019/050531, filed May 29, 2019, and entitled "NITROIMIDAZOLE FORMULATIONS", which claims priority to Australian Patent Application No. 2018901902 filed May 29, 2018, the entire disclosures of which are incorporated herein by this reference.

TECHNICAL FIELD

This invention relates to nitroimidazoles and related compounds, formulations thereof, and their use in the prevention and/or treatment of infectious disease in animals. In particular, the invention relates to 5-nitroimidazoles and related compounds, formulations thereof, and their use in the prevention and/or treatment of infectious disease in animals including bacterial, viral, parasitic or fungal infections. More particularly, the invention relates to metronidazole and related compounds and derivatives, formulations thereof, and their use in the prevention and/or treatment of infectious disease caused by *Clostridium* species.

Throughout this disclosure, various publications are referred to by first author and year of publication. Full citations for these publications, in the order they appear in the application, are presented in a References section immediately before the claims.

BACKGROUND

Antibiotic use has been a staple in animal production worldwide for decades. It is estimated that the world uses about 63,000 tons of antibiotics each year to raise livestock such as cattle and pigs, which is roughly twice that of antibiotics prescribed by doctors globally to fight infections in people, with current trends suggesting world consumption of antibiotics in animals will go up by two-thirds in the next 20 years.

Antimicrobial resistance (AMR) is a natural process whereby microbes evolve to be able to resist the action of antibiotic drugs. This leads to antibiotics becoming less effective over time and in extreme cases, ultimately useless. AMR has increasingly become a problem because the pace at which new antibiotics are discovered has slowed dramatically and consequently there are a very limited number of new drugs. Meanwhile, antibiotic use has risen exponentially increasing the development of resistance.

The overuse of antibiotics contributes to the spread of antibiotic-resistance genes by promoting the selection of antibiotic-resistant bacteria in animals. In addition, waste materials from animals may contain antibiotic residues, resulting in their wider dissemination in the environment. These are major problems of intensive farming methods and the issues caused by their use are largely those of developed rather than developing countries.

Antimicrobial resistance threatens the effective prevention and treatment of an ever-increasing range of infections in animals caused by bacteria, parasites, viruses and fungi. The wide and overuse of antibiotics in food-producing animals contributes to the emergence of antibiotic-resistant bacteria which can contaminate the food and then consumers who in turn can then develop antibiotic-resistant infections. FIG. 1 depicts the spread of AMR from food-producing animal to human.

The fear is the overuse of antibiotics in food-producing animals leading to the spread of drug-resistant bacteria to humans and then in turn the overuse of antibiotics in humans will and has given rise to 'superbugs'—bacteria that are resistant to several classes of antibiotics. Already, it has been estimated that superbugs have caused more than 320,000 deaths each year in China and the US with the death toll expected to exceed 10 million by year 2050 and have cost the world over 100 trillion USD.

The global burden of infections resistant to existing antimicrobial medicines is growing at an alarming rate. For example, use of β-lactam antibiotics and fluoroquinolones can lead to secondary infection and further complications such as overgrowth of *Clostridium difficile* (CD). CD is a bacterium that can cause symptoms ranging from diarrhea to life-threatening inflammation of the colon. CD epidemiology is discussed in Martin et al. 2016.

Illness from CD most commonly affects older adults often in long-term care facilities and typically occurs after use of antibiotic medications. However, studies show increasing rates of CD infection among people traditionally not considered high risk, such as younger and healthy individuals without a history of antibiotic use or exposure to health care facilities. Each year in the United States, about a half million people get sick as a result of release of CD toxins, and in recent years, CD infections have become more frequent, severe and difficult to treat with the rise of antimicrobial resistance. Another difficulty faced in the treatment of CD is the rate of recurrence. Up to 20 percent of people who have been infected with CD get sick again. After two or more recurrences, rates of further recurrence increase up to 65 percent.

Patients with infections caused by drug-resistant bacteria are at an increased risk of worse clinical outcomes and death, and consume more health-care resources than patients infected with non-resistant strains of the same bacteria. It is important to develop new antimicrobial therapies to combat the world wide resistance problems facing human and animal health.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

The present disclosure relates to a method for the prevention and/or treatment of an infectious disease in a mammal, wherein the method comprises administering to the mammal a nitroimidazole.

The present disclosure is based on the finding that a combination of a nitroimidazole and a berberine alkaloid can be used in the prevention and/or treatment of infectious disease caused by *Clostridium*. Surprisingly, it has been found that a nitroimidazole demonstrates synergy in combination with a berberine alkaloid in the prevention and/or treatment of infectious disease caused by *Clostridium*. In this regard, it has been found that administration of metronidazole in combination with berberine sulfate significantly increased efficacy compared to metronidazole and berberine sulfate alone in the prevention and/or treatment of infectious disease caused by *Clostridium*.

Thus, the present disclosure relates to a method for the prevention and/or treatment of an infectious disease in a mammal, wherein the method comprises administering to the mammal a nitroimidazole, wherein the infectious disease is caused by bacteria from the genus *Clostridium*.

The present disclosure also relates to a composition comprising a nitroimidazole and one or more agents suitable for the prevention and/or treatment of an infectious disease in a mammal.

The present disclosure also relates to a composition comprising a synergistically effective amount of a nitroimidazole and one or more agents suitable for the prevention and/or treatment of an infectious disease in a mammal.

The present disclosure also relates to a composition comprising a nitroimidazole and a berberine alkaloid.

The present disclosure also relates to a composition comprising a synergistically effective amount of a nitroimidazole and a berberine alkaloid.

The present disclosure also relates to an animal feed comprising a nitroimidazole, wherein the animal feed is for consumption by a mammal.

The present disclosure also relates to an animal feed comprising a composition as described herein, wherein the animal feed is for consumption by a mammal.

The present disclosure also relates to an animal feed comprising a synergistic composition as described herein, wherein the animal feed is for consumption by a mammal.

The present disclosure also relates to a dosing regimen comprising administering a nitroimidazole for 1 to 6 weeks and in an amount effective to prevent and/or treat an infectious disease in a mammal.

The present disclosure also relates to a dosing regimen comprising administering a composition as described herein for 1 to 6 weeks and in an amount effective to prevent and/or treat an infectious disease in a mammal.

The present disclosure also relates to a dosing regimen comprising administering a synergistic composition as described herein for 1 to 6 weeks and in an amount effective to prevent and/or treat an infectious disease in a mammal.

The present disclosure also relates to a dosing regimen comprising administering:
  an animal feed comprising a nitroimidazole as described herein; or
  an animal feed comprising a composition as described herein; or
  an animal feed comprising a synergistic composition as described herein;
  for 1 to 6 weeks and in an amount effective to prevent and/or treat an infectious disease in a mammal.

The present disclosure also relates to a dosing regimen comprising administering a composition as described herein for 1 to 6 weeks and in an amount effective to prevent and/or treat an infectious disease in a mammal, wherein the infectious disease is caused by bacteria from the genus *Clostridium*.

The present disclosure also relates to a dosing regimen comprising administering a synergistic composition as described herein for 1 to 6 weeks and in an amount effective to prevent and/or treat an infectious disease in a mammal, wherein the infectious disease is caused by bacteria from the genus *Clostridium*.

The present disclosure also relates to a dosing regimen comprising administering:
  an animal feed comprising a nitroimidazole as described herein; or
  an animal feed comprising a composition as described herein; or
  an animal feed comprising a synergistic composition as described herein;
  for 1 to 6 weeks and in an amount effective to prevent and/or treat an infectious disease in a mammal, wherein the infectious disease is caused by bacteria from the genus *Clostridium*.

The present disclosure also relates to a method for preventing and/or treating an infectious disease in an animal, the method comprising administering a composition as described herein.

The present disclosure also relates to a method for preventing or treating an infectious disease in an animal, the method comprising administering a synergistic composition as described herein.

The present disclosure also relates to a method for preventing or treating an infectious disease caused by bacteria from the genus *Clostridium* in a mammal, the method comprising administering a composition as described herein.

The present disclosure also relates to a method for preventing or treating an infectious disease caused by bacteria from the genus *Clostridium* in a mammal, the method comprising administering a synergistic composition as described herein.

The present disclosure also relates to a method for preventing or treating an infectious disease caused by bacteria from the genus *Clostridium* in a mammal, the method comprising administering an animal feed as described herein.

The present disclosure also relates to a method for preventing or treating an infectious disease caused by bacteria from the genus *Clostridium* in a mammal, the method comprising administering:
  an animal feed comprising a nitroimidazole as described herein; or
  an animal feed comprising a composition as described herein; or
  an animal feed comprising a synergistic composition as described herein,
  to the mammal.

The present disclosure also relates to a method for the reduction of feed conversion ratio in a food-producing animal, wherein the method comprises the step of administering a nitroimidazole to the food-producing animal, wherein the food-producing animal is a mammal.

The present disclosure also relates to a method for the reduction of feed conversion ratio in a food-producing animal, wherein the method comprises the step of administering a composition as described herein, wherein the food-producing animal is a mammal.

The present disclosure also relates to a method for the reduction of feed conversion ratio in a food-producing animal, wherein the method comprises the step of administering a synergistic composition as described herein, wherein the food-producing animal is a mammal.

The present disclosure also relates to a method for the reduction of feed conversion ratio in a food-producing animal, wherein the method comprises the step of administering:
  an animal feed comprising a nitroimidazole; or
  an animal feed comprising a composition as described herein; or
  an animal feed comprising a synergistic composition as described herein,
  to the food-producing animal, wherein the food-producing animal is a mammal.

The present disclosure also relates to a method for improving or maintaining gastrointestinal health in a mammal, wherein the method comprises the step of administering a nitroimidazole to the mammal.

The present disclosure also relates to a method for improving or maintaining gastrointestinal health in a mammal, wherein the method comprises the step of administering a composition as described herein.

The present disclosure also relates to a method for improving or maintaining gastrointestinal health in a mammal, wherein the method comprises the step of administering a synergistic composition as described herein.

The present disclosure also relates to a method for improving or maintaining gastrointestinal health in a mammal, wherein the method comprises the step of administering an animal feed as described herein.

an animal feed comprising a nitroimidazole as described herein; or
an animal feed comprising a composition as described herein; or
an animal feed comprising a synergistic composition as described herein,
to the mammal.

The present disclosure also relates to use of a nitroimidazole in the preparation of: a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole and one or more agents suitable for the prevention and/or treatment of an infectious disease in a mammal in the preparation of a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole and a berberine alkaloid in the preparation of a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole in the preparation of a medicament for
(i) the prevention and/or treatment of an infectious disease in a mammal, wherein the infectious disease is caused by bacteria from the genus *Clostridium*;
or
(ii) improving or maintaining gastrointestinal health in a mammal;
or
(iii) the reduction of feed conversion ratio in a food-producing animal, wherein the food-producing animal is a mammal.

The present disclosure also relates use of a nitroimidazole and one or more agents suitable for the prevention and/or treatment of an infectious disease in a mammal in the preparation of a medicament for:
(i) the prevention and/or treatment of an infectious disease in a mammal, wherein the infectious disease is caused by bacteria from the genus *Clostridium*;
or
(ii) improving or maintaining gastrointestinal health in a mammal;
or
(iii) the reduction of feed conversion ratio in a food-producing animal, wherein the food-producing animal is a mammal.

The present disclosure also relates to use of a nitroimidazole and a berberine alkaloid in the preparation of a medicament for:
(i) the control, prevention and/or treatment of an infectious disease in a mammal, wherein the infectious disease is caused by bacteria from the genus *Clostridium*;
or
(ii) improving or maintaining gastrointestinal health in an animal;
or
(iii) the reduction of feed conversion ratio in a food-producing animal.

The present disclosure also relates to use of a nitroimidazole in:
(i) the prevention and/or treatment of an infectious disease in a mammal, wherein the infectious disease is caused by bacteria from the genus *Clostridium*;
or
(ii) improving or maintaining gastrointestinal health in a mammal;
or
(iii) the reduction of feed conversion ratio in a food-producing animal, wherein the food-producing animal is a mammal.

The present disclosure also relates to use of a nitroimidazole and one or more agents suitable for the prevention and/or treatment of an infectious disease in a mammal in:
(i) the prevention and/or treatment of an infectious disease in a mammal, wherein the infectious disease is caused by bacteria from the genus *Clostridium*;
or
(ii) improving or maintaining gastrointestinal health in a mammal;
or
(iii) the reduction of feed conversion ratio in a food-producing animal, wherein the food-producing animal is a mammal.

The present disclosure also relates to use of a nitroimidazole and a berberine alkaloid in:
(i) the prevention and/or treatment of an infectious disease in a mammal, wherein the infectious disease is caused by bacteria from the genus *Clostridium*;
or
(ii) improving or maintaining gastrointestinal health in a mammal;
or
(iii) reduction of feed conversion ratio in a food-producing animal, wherein the food-producing animal is a mammal.

The present disclosure also relates to use of a nitroimidazole in the preparation of a medicament for the prevention and/or treatment of an infectious disease in a mammal.

The present disclosure also relates to use of a nitroimidazole and one or more agents suitable for the prevention and/or treatment of an infectious disease in an animal in the preparation of a medicament for the prevention and/or treatment of an infectious disease in a mammal.

The present disclosure also relates to use of a nitroimidazole and a berberine alkaloid in the preparation of a medicament for the prevention and/or treatment of an infectious disease in a mammal.

The present disclosure also relates to use of a nitroimidazole in the prevention and/or treatment of an infectious disease in a mammal.

The present disclosure also relates to use of a nitroimidazole and one or more agents suitable for the prevention and/or treatment of an infectious disease in a mammal in the prevention and/or treatment of an infectious disease in a mammal.

The present disclosure also relates to use of a nitroimidazole and a berberine alkaloid in the prevention and/or treatment of an infectious disease in a mammal.

The present disclosure also relates to a nitroimidazole for use in the prevention and/or treatment of an infectious disease in a mammal.

The present disclosure also relates to a nitroimidazole for use in improving or maintaining gastrointestinal health in a mammal.

The present disclosure also relates to a nitroimidazole for use in the reduction of feed conversion ratio in a food-producing animal, wherein the food-producing animal is a mammal.

The present disclosure also relates to a nitroimidazole and one or more agents suitable for the prevention and/or treatment of an infectious disease in a mammal for use in the prevention and/or treatment of an infectious disease in a mammal.

The present disclosure also relates to a nitroimidazole and any one or more agents suitable for the prevention and/or treatment of an infectious disease in a mammal for use in improving or maintaining gastrointestinal health in a mammal.

The present disclosure also relates to a nitroimidazole and any one or more agents suitable for the prevention and/or treatment of an infectious disease in a mammal for use in the reduction of feed conversion ratio in a food-producing animal, wherein the food-producing animal is a mammal.

The present disclosure also relates a nitroimidazole and a berberine alkaloid for use in the prevention and/or treatment of an infectious disease in a mammal.

The present disclosure also relates to a nitroimidazole and a berberine alkaloid for use in improving or maintaining gastrointestinal health in a mammal.

The present disclosure also relates to a nitroimidazole and a berberine alkaloid for use in the reduction of feed conversion ratio in a food-producing animal, wherein the food-producing animal is a mammal.

DEFINITIONS

Unless specifically defined otherwise, all technical and scientific terms used herein shall be taken to have the same meaning as commonly understood by one of ordinary skill in the art (e.g., chemistry, biochemistry, formulation science, food and nutritional science, animal science and animal husbandry, cell culture, and molecular biology). Further, unless otherwise required by context, singular terms shall include pluralities and plural terms shall include the singular. Thus, as used in this specification and the appended claims, the singular forms "a", "an" and "the" include plural referents unless the context clearly indicates otherwise. Thus, the term "a mammal" means "one or more mammals" unless the context clearly indicates otherwise.

The term "about" as used herein refers to a range of +/−10% of the specified value.

As used herein the term "acceptable excipient" refers to a solid or liquid filler, carrier, diluent or encapsulating substance that may be safely used in administration. Depending upon the particular route of administration, a variety of carriers, well known in the art may be used. These carriers or excipients may be selected from a group including sugars, starches, cellulose and its derivatives, malt, gelatine, talc, calcium sulfate, vegetable oils, synthetic oils, polyols, which may be used to aid in the solubilisation of nitroimidazoles as discussed in, for example, U.S. Pat. No. 8,658,678, alginic acid, phosphate buffered solutions, emulsifiers, isotonic saline, and pyrogen-free water. Excipients for pharmaceutical applications are discussed, for example, in Remington: The Science and Practice of Pharmacy, 2005 Remington: The Science and Practice of Pharmacy, 2005 or the Handbook of Pharmaceutical Excipients, 2009. Excipients for veterinary applications are discussed in, for example, in the Merck Veterinary Manual (online at www.merckvetmanual.com) or the CRC Handbook of Food, Drug and Cosmetic Excipients, 2005.

As used herein the term "acceptable salt" refers to salts which are toxicologically safe for systemic administration. Acceptable salts, including acceptable acidic/anionic or basic/cationic are described in Gould, 1986; S. M. Berge et al., 1977; and Stahl and Wermuth (Eds.) (2011).

Acceptable salts of the acidic or basic compounds of the invention can of course be made by conventional procedures (such as reacting a free acid with the desired salt-forming base or reacting a free base with the desired salt-forming acid).

Acceptable salts of acidic compounds include salts with cations and may be selected from alkali or alkaline earth metal salts, including, sodium, lithium, potassium, calcium, magnesium and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like, and salts with organic bases. Suitable organic bases include N-methyl-D-glucamine, arginine, benzathine, diolamine, olamine, procaine and tromethamine.

Acceptable salts of basic compounds include salts with anions and may be selected from organic or inorganic acids. Suitable anions include acetate, acylsulfates, acylsulfonates, adipate, ascorbate, benzoate, besylate, bromide, camsylate, caprate, caproate, caprylate, chloride, citrate, docusate, edisylate, estolate, formate, fumarate, gluceptate, gluconate, glucuronate, hippurate, hyclate, hydrobromide, hydrochloride, iodide, isethionate, lactate, lactobionate, laurate, malate, maleate, mesylate, methylbromide, methylsulfate, napsylate, nitrate, octanoate, oleate, pamoate, phosphate, polygalacturonate, salicylate, stearate, succinate, sulfate, sulfonate, sulfosalicylate, tannate, tartrate, terephthalate, tosylate, triethiodide and the like.

Imidazoles such as nitromidazoles are amphoteric in regard to their ability to act as a base or an acid. An example of an acceptable salt of a nitromidazole, when acting as an acid, is sodium nitroimidazolate (sodium is the cation; nitroimidazolate is the anion). An example of an acceptable salt of a nitromidazole, when acting as a base, is the imidazolium hydrochloride chloride salt (nitroimidazolium is the cation; chloride is the anion).

Berberine is a positively charged quaternary ammonium cation. Acceptable salts of beberine include without limitation chloride, hemisulfate and iodide salts.

The present invention also contemplates nitroimidazole salts as acceptable salts. For example, an acceptable salt of berberine is berberine nitroimidazolate and, vice versa, an acceptable salt of nitroimidiazole is berberine nitroimidazolate, where berberine is the cation and nitroimidazolate is the anion. It will be recognised that berberine nitroimidazolate may display a combination of the biological activity possessed by the berberine ammonium cation and the biological activity possessed by the nitroimidazolate counter anion.

As used herein "acceptable solvent" is a solvent which for the purpose of the disclosure may not interfere with the biological activity of the solute. Examples of suitable solvents include, but are not limited to, water, ethanol and acetic acid, glycerol, liquid polyethylene glycols and mixtures thereof. A particular solvent is water. The term "solvate" refers to a complex of variable stoichiometry formed by a solute (for example, a berberine alkaloid) and a solvent. In particular, the solvent used is an "acceptable solvent" as defined herein. When water is the solvent, the molecule is referred to as a hydrate.

The term "animal feed", as used herein, refers to any compound, preparation, or mixture suitable for, or intended for consumption/intake by an animal. As used herein, the term "feed additive" refers to a substance which is added to a feed for a number of reasons. A feed additive may be added to the feed for the purpose of supplementing the feed. In this case, the feed additive may be referred to as a "feed supplement". It would be understood that supplementing feed includes, but is not limited to enhancing digestibility of the feed, completing the nutritional value of the feed, improving or maintaining the health of the recipient such as improving or maintaining the immune defence or improving or maintaining gastrointestinal health. The feed additive may be added to the feed for the purpose of improving the shelf-life of the feed. In that regard, the feed additive may be used as a preservative to avoid the spoilage of feed. A feed additive or a feed supplement may also be considered a feed herein.

As used herein the term "antimicrobial activity" is defined herein as an activity that kills or inhibits the growth of microorganisms including, but not limited to bacteria, viruses, parasites, and fungi. Whilst a substance which displays antimicrobial activity may be used in the prevention and/or treatment of an infectious disease, it would also be recognised that a substance which displays antimicrobial activity may be used as a preservative to avoid the spoilage of food.

As used herein "IRP001" refers to berberine, which as described herein is an isoquinoline plant natural product with antimicrobial activity. The terms "IRP001" and "berberine" are used interchangeably herein. As used herein, "IRP001 chloride" or "IRP001 Cl" denotes the chloride salt of berberine; and "IRP001 sulfate" refers to the hemisulfate salt of berberine. Thus, it would be appreciated that the terms "IRP001 sulfate", "berberine sulfate", "IRP001 hemisulfate, and "berberine hemisulfate" are equivalent herein. The molecular structures of the berberine quaternary ammonium cation, and the chloride and hemisulfate salts are shown in FIG. 2.

As used herein, the term "berberine alkaloid(s)" refers to berberine and related compounds and derivatives thereof which share similar structures and characteristics to berberine and are suitable for the compositions/animal feeds/animal feed additives/dosing regimens/methods/uses of the disclosure. As described herein berberine is an isoquinoline quaternary alkaloid and plant natural product with antimicrobial activity.

Berberine alkaloids include, but are not limited to the protoberberines. Non-limiting examples of berberine alkaloids are: beberine, berberrubine, coreximine, tetrahydropalmatine, jatrorrhizine, 13-hydroxyberberine chloride, coralyne chloride, 7,8-dihydro-13-methylberberine, fibrauretin (palmatine), 13-benzylberberine and acceptable salts thereof.

Berberine alkaloids can exist in different isomers or different isomeric forms, for example, various tautomers or tautomeric forms. It will be understood that the term "berberine alkaloid(s)" encompasses different isomeric forms in isolation from each other as well as mixtures.

Berberine alkaloids can also exist in various amorphous forms and crystalline forms (i.e. polymorphs). It will be also understood that the term "berberine alkaloid(s)" encompasses different amorphous and crystalline forms in isolation from each other as well as mixtures.

As used herein, the term "berberine alkaloid(s)" encompasses acceptable salts, solvates, solvates of said salts and pro-drugs thereof.

Thus, it will be understood that reference to a "berberine alkaloid(s)" encompasses, where permitted, all derivatives, isomeric forms, racemates, amorphous or crystalline forms, solvates, acceptable salts, solvates of said salts, and prodrugs thereof in isolation from each other as well as mixtures.

As used herein, the term "comprise", or variations such as "comprises" or "comprising" will be understood to imply the inclusion of a stated element, integer or step, or group of elements, integers or steps, but not the exclusion of any other element, integer or step, or group of elements, integers or steps.

The term "composition" as used herein is intended to encompass a product comprising the specified ingredients in the specified amounts, as well as any product which results, directly or indirectly, from combination of the specified ingredients in the specified amounts.

As used herein, the term "derivative(s)" encompasses compounds that are generated from a parent compound. Herein, a reference to derivatives also includes a reference to metabolites. Derivatives may result from e.g. functionalization, substitution, redox manipulation, unsaturation and/or ring incorporation of the parent compound.

It would be recognised that the term "nitroimidazoles" is used to represent a group of antibiotic compounds, based on a nitroimidazole heterocycle (Edwards 1993). Nitroimidazoles are themselves part of a larger family of nitroheterocyle antibiotics, including nitrothiazoles, nitrofurans and nitrothiophenes. Nitroheterocyle antibiotics can be considered as prodrugs in that are activated by reduction in the target microbe to generate the bioactive species: toxic, short-lived radical intermediates. Microbial specificity results, in part, from differences in redox potentials between mammals and microbes.

The present disclosure is directed to 2-, 4- and 5-nitroimidazoles. In particular, the present disclosure is directed to 5-nitroimidazoles and more particularly metronidazole.

Table 1 depicts a general formula, formula (I), for the nitroimidazole compounds of the present disclosure and general formulae: formula (Ia), formula (Ib), and formula (Ic) for the 2-, 4- and 5-nitroimidazole compounds of the present disclosure.

TABLE 1

Nitroimidazoles of the present disclosure

| Formulae | Description |
| --- | --- |
| $\underset{n(R)}{\overset{R}{\underset{|}{N}}}\diagdown\!\!\!\!\!\diagup^{NO_2}_{N}$ | General formula for nitroimidazoles of the present disclosure |

TABLE 1-continued

Nitroimidazoles of the present disclosure

| Formulae | Description |
| --- | --- |
| (I) [structure: imidazole ring with R¹ on N1, NO₂ on C2, R⁵ on C5, R⁴ on C4] | General formula for 2-nitroimidazoles of the present disclosure |
| (Ia) [structure: imidazole ring with R¹ on N1, R² on C2, R⁵ on C5, O₂N on C4] | General formula for 4-nitroimidazoles of the present disclosure |
| (Ib) [structure: imidazole ring with R¹ on N1, R² on C2, O₂N on C5, R⁴ on C4] | General formula for 5-nitroimidazoles of the present disclosure |
| (Ic) | |

With respect to Formula (I), n is 0, 1 or 2; and R is independently hydrogen or a substituent as defined herein.

With respect to Formulae (Ia) to (Ic): $R^1$ is a substituent on the N1 atom of the imidazole ring; $R^2$ is a substituent on the C2 atom of the imidazole ring; $R^4$ is a substituent on the C4 atom of the imidazole ring; and $R^5$ is a substituent on the C5 atom of the imidazole ring.

With respect to Formula (Ia), $R^1$, $R^4$ and $R^5$ are each independently hydrogen or a substituent as defined herein. With respect to Formula (Ib), $R^1$, $R^2$ and $R^5$ are each independently hydrogen or a substituent as defined herein. With respect to Formula (Ic), $R^1$, $R^2$ and $R^4$ are each independently hydrogen or a substituent as defined herein.

It would be understood that a range of nitroimidazoles, can be obtained by isolation from natural sources, such as natural plant sources or soils, through modification of biosynthetic pathways, through chemical synthesis and/or chemical derivatisation. Derivatives can be generated from functionalization and/or substitution of the nitroimidazole heterocycle. Derivatization may also include the incorporation of other various sized ring structures into the nitroimidazole heterocycle (hereinafter "ring incorporation"). Substituents may also be derivatised i.e. through functionalisation, redox manipulation, i.e., oxidation or reduction, and unsaturation. In addition to functionalization, redox manipulation, and unsaturation, substituents may also be derivatised through ring incorporation.

Nitroimidazoles can exist in different isomers or different isomeric forms, for example, various tautomers or tautomeric forms. It will be understood that the term "nitroimidazole(s)" and the like, for example, "5-nitroimidazole(s)", "4-nitroimidazole(s)" and "2-nitroimidazole(s)" encompasses different isomeric forms of nitroimidazoles in isolation from each other as well as combinations.

Nitroimidazoles can also exist in various amorphous forms and crystalline forms (i.e. polymorphs). It will be understood that the term "nitroimidazole(s)" encompasses different amorphous and crystalline forms in isolation from each other as well as combinations.

Thus it will be understood that reference to a "nitroimidazole(s)" encompasses, where permitted, all derivatives, isomeric forms, racemates, amorphous or crystalline forms, and acceptable salts of the nitroimidazole(s) and solvates thereof and prodrugs thereof. For example, it will be understood that a reference to the nitroimidazole "metronidazole" encompasses, where permitted, all derivatives, isomeric forms, racemates, amorphous or crystalline forms, and acceptable salts of metronidazole and solvates thereof and prodrugs thereof.

The term "animal subject" or the term "animal" as used herein refer to any mammal. Thus, the disclosure relates to "animal subjects"/"animals" that are mammals. The mammal may be human. The mammal may be non-human, for example, a horse, dog, cat, sheep, cattle, pig or primate. The terms "subject", "individual" and "patient" are used interchangeably herein.

As used herein, the term "food-producing animal" refers to a mammal that is farmed for the production of food for consumption by another animal, for example, a human. It would be understood that the term "food-producing animal" includes, for example, a pig.

It will be understood that the term "isomer" refers to structural or constitutional isomers, tautomers, regioisomers, geometric isomers, or stereoisomers including enantiomers or diastereisomers. Further, a racemate will be understood to comprise an equimolar mixture of a pair of enantiomers.

It will be understood that the term "prodrug" refers to an inactive form of a compound which is transformed in vivo to the active form or species. Suitable prodrugs include esters, ethers, N-oxides, phosphonate esters etc, of the active form of the compound. Pro-drugs are useful when the desired active form of a compound has chemical or physical properties which make its administration difficult or inefficient. For example, the desired active form may be poorly soluble or it may be poorly transported or it may have an undesirably short plasma half-life and thus have low bioavailability. As discussed above, nitroheterocycle antibiotics such as nitroimidazoles can be considered as prodrugs because they are reduced in vivo to give the bioactive species. Nonetheless, the present disclosure contemplates prodrugs of nitroimidazoles. For example, suitable variation of the $R^1$ substituent of nitroimidazoles can improve the pharmacokinetic profile of these compounds by reducing metabolic degradation through oxidation (see Kapoor et al. 2003). In this regard, replacement of the metronidazole $R^1$ 1-(2-hydroxyethyl) substituent, which is readily oxidised metabolically, has resulted in the development of other clinically useful antibiotic compounds such as tinidazole, panidazole, orinidazole, secnidazole, carnidazole and ternidazole (see Table 2 and FIG. 7). Table 2 and FIG. 7 also depict metronidazole methyl ether, metronidazole acetate and metronidazole benzoate. Further discussion of pro-drugs may be found in Stella, V. J. et al. 1985.

The present disclosure also contemplates where the "prodrug" is formed from two active agents. For example, a berberine alkaloid, or an appropriate derivative may be the acid partner in an ester "prodrug" with a nitromidiazole, or an appropriate derivative, is the alcohol partner in the ester "prodrug". It will be recognised that such a "prodrug" may display a combination of the biological activity possessed by the berberine alkaloid and the biological activity possessed by the nitroimidazole. The present disclosure further contemplates berberine alkaloid and nitroimidazole hybrid molecules, for example, the hybrid molecules disclosed in Zhang et al. 2013; Fang et al. 2001; CN 106749227 A and CN 102516242 B. The disclosure of these compounds and the subject matter relating to these compounds is hereby incorporated by reference. Thus, the term "nitroimidazole" includes, but is not limited to the compounds disclosed in the above references. It would also be understood that the term "nitroimidazole" as used herein also encompasses, where permitted, all derivatives, isomeric forms, racemates, amorphous or crystalline forms, acceptable salts, solvates thereof, and prodrugs thereof of the compounds disclosed in the above references.

As used herein a "safe" residue level of berberine is one that poses an insignificant risk of disease, particularly cancer. As used herein, the term "no residue" refers to any residue remaining in the edible tissues of food-producing animals that is so low that it presents an insignificant risk of cancer to consumers. More specifically, an insignificant risk of cancer is defined as a 1 in 1 million increase in risk.

As used herein, the term "optionally substituted" means that the radical, group or moiety being referred to is "substituted" or "unsubstituted". The term "substituted" means that the radical, group or moiety may have one or more substituents, or has one or more substituents present. Accordingly, the term "unsubstituted" means that the corresponding radical, group or moiety has no substituents.

Where a radical, group or moiety has a plurality of substituents, and a selection of various substituents is specified, the substituents are selected independently of one another and do not need to be identical. When a radical, group or moiety is a substituted group, at least one hydrogen atom on the radical, group of moiety is replaced with a substituent. In the case of an oxo substituent (=O) two hydrogen atoms are replaced.

As used herein, the terms "substituted", "substituent" and "substituents" encompass all permissible substituents of organic compounds. This disclosure is not intended to be limited in any manner by the permissible substituents of organic compounds. Representative permissible substituents include, but are not limited to: alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfonamido and permissible combinations thereof including, but not limited to alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocyclthio, heteroarylthio, alkylsulfonyl, arylsulfonyl, wherein any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted and wherein the further substituent is itself optionally further substituted.

In certain embodiments, the term "substituent(s)" includes, but is not limited to: alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl and arylsulfonyl, wherein any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted with, for example, any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^x$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Substituents may also be derivatised i.e. through functionalisation, redox manipulation, i.e., oxidation or reduction, and unsaturation. In addition to functionalization, redox manipulation, and unsaturation, substituents may also be derivatised through ring incorporation (hereinafter "ring incorporation").

As used herein, the term "substituted" means that the carbon backbone of the group being referred to is substituted, however, the term "substituted" also includes the possibility for substitution on a heteroatom, such as nitrogen, which is located on the carbon backbone. Thus, the term "substituted" means that one or more hydrogen atoms on the carbon backbone is replaced by one or more of the groups indicated. Where more than one substitution occurs, they may be on the same, adjacent or remote carbon atoms, i.e., located on carbon atoms that are 0, 1, 2, 3, 4, 5, 6, 7, 8, 9, 10 or more carbon atoms apart. For the purposes of this disclosure, heteroatoms such as nitrogen may have hydrogen substituents and/or any permissible substituents of organic compounds described herein which satisfy the valencies of the heteroatoms.

As used herein, "alkyl" means a straight saturated aliphatic hydrocarbon chain or a branched saturated aliphatic hydrocarbon chain. The alkyl group may contain from 1 to 25 carbon atoms. The term "$C_{1-10}$alkyl" means an alkyl group containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. An "alkyl" group may be substituted or unsubstituted. In this regard, the term "haloalkyl", as used herein, refers to "alkyl" substituted with one or more halo i.e. one or more of F, Cl, Br or I. An example of "haloalkyl" is —CF$_3$.

As used herein, "cycloalkyl" means a cyclic saturated aliphatic hydrocarbon. Representative "cycloalkyls" include cyclopropyl, cyclobutyl, cyclopentyl, cyclohexyl, and the like. The term "$C_{1-10}$cycloalkyl" means a cycloalkyl group containing from 1 to 10 carbon atoms. A "cycloalkyl" group may be substituted or unsubstituted.

As used herein, the term "oxaalkyl" means an alkyl group containing an oxygen atom, i.e., the alkyl group contains the species —O—. The term "$C_{1-10}$oxaalkyl" means an alkyl group containing from 1 to 10 carbon atoms and also containing an oxygen atom i.e., the alkyl group contains the species —O— within the chain. An "oxaalkyl" group may be substituted or unsubstituted.

As used herein, the term "cyclooxaalkyl" means a cycloalkyl group containing an oxygen atom, i.e., the cycloalkyl group contains the species —O—. The term "$C_{1-10}$cyclooxaalkyl" means a cycloalkyl group containing from 1 to 10 carbon atoms and also containing an oxygen atom, i.e., the cycloalkyl group contains the species —O—. A "cyclooxaalkyl" group may be substituted or unsubstituted.

As used herein, the term "alkenyl" means an alkyl, as defined above, containing one double bond between adjacent carbon atoms. The alkenyl group may contain from 1 to 25 carbon atoms. The term "$C_{1-10}$alkenyl" means an alkenyl group containing from 1 to 10 carbon atoms, where $C_1$alkenyl denotes a double bond between a methylene substituent and the carbon atom bearing said methylene substituent. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An "alkenyl" group may be substituted or unsubstituted.

As used herein, "cycloalkenyl" means a cyclic unsaturated aliphatic hydrocarbon. Representative "cycloalkenyls", include cyclopentenyl and cyclohexenyl, and the like. The term "$C_{1-10}$cycloalkenyl" means a cycloalkenyl group containing from 1 to 10 carbon atoms. A "cycloalkenyl" group may be substituted or unsubstituted.

As used herein, the term "oxaalkenyl" means an alkenyl group, as defined above, containing an oxygen atom, i.e., the alkenyl group contains the species —O— within the chain. The term "$C_{1-10}$oxaalkenyl" means an alkenyl group containing from 1 to 10 carbon atoms and also containing an oxygen atom, i.e., the alkenyl group contains the species —O— within the chain. A "oxaalkenyl" group may be substituted or unsubstituted.

As used herein, the term "cyclooxaalkenyl" means a cycloalkenyl group, as defined above, containing an oxygen atom, i.e., the alkenyl group contains the species —O— within the chain. The term "$C_{1-10}$cyclooxaalkenyl" means a cycloalkenyl group containing from 1 to 10 carbon atoms and also containing an oxygen atom, i.e., the cycloalkenyl group contains the species —O—. A "cyclooxaalkenyl" group may be substituted or unsubstituted.

As used herein, the term "alkadienyl" means an alkyl group, as defined above, containing two double bonds where one double bond is between a first pair of adjacent carbon atoms and the other double bond is between a second pair of adjacent carbon atoms as in the structure —C=C—C=C—. The term "alkadienyl", as used herein, also means an alkyl group, as defined above, wherein one carbon atom has two double bonds with each of its two adjacent carbon atoms as in the structure —C=C=C—C—. As used herein, the alkadienyl group may contain from 1 to 25 carbon atoms. The term "$C_{3-10}$alkadienyl" means an alkadienyl group containing from 3 to 10 carbon atoms and two double bonds. An "alkadienyl" group may be substituted or unsubstituted.

Following the above, the term "$C_3$alkadienyl", as used herein, denotes, for example, a propadienyl group such as in the structure:

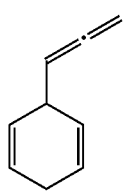

Also, the term "C₃alkadienyl", as used herein, denotes, for example, a moiety where there is a double bond between a propylene substituent and the carbon atom bearing said propylene substituent such as in the structure:

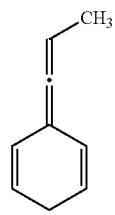

Alkadienyls include cis and/or trans isomers i.e an alkadienyl group may include: cis:cis; trans:trans; cis:trans, or trans:cis double bonds.

As used herein, the term "cycloalkadienyl" means a cycloalkyl group, as defined above, containing two double bonds where one double bond is between a first pair of adjacent carbon atoms and the other double bond is between a second pair of adjacent carbon atoms as in the structure —C═C—C═C—. The term "cycloalkadienyl", as used herein, also means a cycloalkyl group, as defined above, wherein one carbon atom has two double bonds with each of its two adjacent carbon atoms as in the structure —C═C═C—C—. A "cycloalkadienyl" group may be substituted or unsubstituted.

As used herein, the term "oxaalkadienyl" means an alkadienyl group, as defined above, which contains an oxygen atom, i.e., the alkadienyl group contains the species —O—. The term "$C_{1-10}$oxaalkadienyl" means an oxaalkadienyl group containing from 1 to 10 carbon atoms and also containing an oxygen atom, i.e., the oxaalkadienyl group contains the species —O—. An "oxaalkadienyl" group may be substituted or unsubstituted.

As used herein, the term "cyclooxaalkadienyl" means a cycloalkadienyl group, as defined above, which contains an oxygen atom, i.e., the cycloalkadienyl group contains the species —O—. The term "$C_{1-10}$cyclooxaalkadienyl" means a cyclooxaalkadienyl group containing from 1 to 10 carbon atoms and also containing an oxygen atom, i.e., the cyclooxaalkadienyl group contains the species —O—. A "cyclooxaalkadienyl" radial may be substituted or unsubstituted.

As used herein, the term "alkynyl" means any alkyl or alkenyl, as defined above, which additionally contains at least one triple bond between adjacent carbons. The alkynyl group may contain from 2 to 25 carbon atoms. Representative straight chain and branched alkynyls include acetylenyl, propynyl, 1-butynyl, 2-butynyl, 1-pentynyl, 2-pentynyl, 3-methyl-1-butynyl, and the like. An "alkynyl" radical may be substituted or unsubstituted.

As used herein, the term "aryl" as used herein refers to a mono- or polycyclic unsaturated aromatic hydrocarbon radical. The aryl radical may have 3 to 22 carbon atoms, which can be optionally substituted. The term "aryl" also includes systems in which the aromatic cycle is part of a bi- or polycyclic saturated, partially unsaturated and/or aromatic system, such as where the aromatic cycle is fused to another aromatic cycle or a cycloalkyl, heteroaryl or heterocyclyl group as defined herein via any desired and possible ring member of the aromatic cycle. The bonding to the nitroimidazoles of the present disclosure can be affected via any possible ring member of the aryl radical. Non-limiting examples of suitable aryl radicals are phenyl, biphenyl, naphthyl, 1-naphthyl, 2-naphthyl, binaphthyl, 1,2,3,4-tetrahydronaphthyl, acenaphthyl, anthracenyl, azulenyl, benzfluoryl, benzphenanthryl, chrysyl, indanyl, indenyl, fluoryl, fluorenyl, picenyl and pyrenyl. An "aryl" radical may be substituted or unsubstituted.

As used herein, the term "heteroaryl" refers to an unsaturated aromatic hydrogen radical having at least one heteroatom. The heteroaryl group may have, for example, one, two, three, four, five or six rings, which may be fused or bicyclic. In certain embodiments, "heteroaryl" refers to an aromatic monocyclic ring system containing five members (a 5-membered heteroaryl) of which at least one member is a N atom (a 5-membered nitrogen-containing heteroaryl); a O atom (a 5-membered oxygen-containing heteroaryl); or a S atom (a 5-membered sulfur-containing heteroaryl).

Such 5-membered heteroaryl groups may contain additional O, N or S atoms. For example, the 5-membered heteroaryl groups may contain one, two or three additional N atoms. Thus, in certain embodiments, the "heteroaryl" may be a 5-membered heteroaryl group containing: two nitrogen atoms; or a N atom and a O atom; or a N atom and a S atom. In certain embodiments, the "heteroaryl" may be a 5-membered heteroaryl group containing: two oxygen atoms; or a O atom and a S atom. In certain embodiments, the "heteroaryl" may be a 5-membered heteroaryl group containing two sulfur atoms. In certain embodiments, the "heteroaryl" may be a 5-membered heteroaryl group containing three nitrogen atoms. In certain embodiments, the "heteroaryl" may be a 5-membered heteroaryl group containing four nitrogen atoms.

In certain embodiments, "heteroaryl" refers to an aromatic monocyclic ring containing six members (a 6-membered heteroaryl) of which at least one member is a N atom (a 5-membered nitrogen-containing heteroaryl); a O atom (a 6-membered oxygen-containing heteroaryl); or a S atom (a 6-membered sulfur-containing heteroaryl).

Such 6-membered heteroaryl groups may contain additional O, N or S atoms. For example, the 6-membered heteroaryl groups may contain one, two or three additional N atoms. Thus, in certain embodiments, the "heteroaryl" may be a 6-membered heteroaryl group containing: two nitrogen atoms; or a N atom and a O atom; or a N atom and a S atom. In certain embodiments, the "heteroaryl" may be a 6-membered heteroaryl group containing: two oxygen atoms; or a O atom and a S atom. In certain embodiments, the "heteroaryl" may be a 6-membered heteroaryl group containing two sulfur atoms. In certain embodiments, the "heteroaryl" may be a 6-membered heteroaryl group containing three nitrogen atoms. In certain embodiments, the "heteroaryl" may be a 6-membered heteroaryl group containing four nitrogen atoms.

In certain embodiments, "heteroaryl" refers an aromatic bicyclic or fused ring containing nine members of which at least one member is a N, O or S atom and which optionally contains one, two or three additional N atoms; or an aromatic bicyclic ring containing ten members of which at least one member is a N, O or S atom. For example, the aromatic bicyclic ring containing ten members is one in which one, two or three members are a N atom.

By way of non-limiting example, suitable heteroaryl groups include furanyl, pyridyl, pyrimidyl, phthalimido, phthalazinyl, thiophenyl, pyrrolyl, imidazolyl, pyrazolyl, thiazolyl, isothiazolyl, oxazolyl, oxadiazolyl, pyronyl, pyrazinyl, tetrazolyl, thionaphthyl, benzofuranyl, isobenzofuryl, indolyl, oxyindolyl, isoindolyl, indazolyl, indolinyl, azaindolyl, isoindazolyl, coumarinyl, isocoumarinyl, quinolyl, isoquinolyl, cinnolinyl, quinazolinyl, pyridopyridyl, benzoxazinyl, quinoxadinyl, chromenyl, isochromenyl, chromanyl, isochromanyl, carbolinyl, thiazolyl, isoxazolyl, isoxazolonyl, isothiazolyl, triazolyl, oxadiazolyl, thiadiazolyl, naphthyridinyl, triazinyl, purinyl, pyridopyrimidinyl, pteridinyl, benzodioxepinyl and pyridazyl. A "heteroaryl" radical may be "optionally substituted" i.e. the "heteroaryl" radical may be substituted or unsubstituted.

As used herein the term, "heterocyclyl" refers to a saturated or partially unsaturated ring having at least three members of which at least one member is a heteroatom such as N, O or S and which optionally contains one additional heteroatom such as an additional O atom or additional N atom. Hence, the term "heterocyclyl" encompasses a saturated or partially unsaturated ring having four members of which at least one member is a N, O or S atom and which optionally contains one additional O atom or one or two additional N atoms; a saturated or partially unsaturated ring having five members of which at least one member is a N, O or S atom and which optionally contains one additional O atom or one, two or three additional N atoms; a saturated or partially unsaturated ring having six members of which one, two or three members are an N, O or S atom and which optionally contains one additional O atom or one, two or three additional N atoms; saturated or partially unsaturated ring having seven members of which one, two or three members are an N, O or S atom and which optionally contains one additional O atom or one, two or three additional N atoms; a saturated or partially unsaturated ring having eight members of which one, two or three members are an N, O or S atom and which optionally contains one additional O atom or one, two or three additional N atoms; a saturated or partially unsaturated bicyclic ring having nine members of which at least one member is a N, O or S atom and which optionally contains one, two or three additional N atoms; or a saturated or partially unsaturated bicyclic ring having ten members of which one, two or three members are an N, O or S atom and which optionally contains one additional O atom or one, two or three additional N atoms. By way of non-limiting example, suitable heterocyclyl groups include pyrrolinyl, pyrrolidinyl, dioxolanyl, tetrahydrofuranyl, morpholinyl, imidazolinyl, imidazolidinyl, pyrazolidinyl, piperidinyl, pyranyl, dihydropyranyl, benzopyranyl, tetrahydropyranyl, thiopyranyl, tetrahydrothiopyranyl and piperazinyl. A "heterocyclyl" radical may be substituted or unsubstituted.

As used herein, the term "halo" refers to a halogen. In particular, the term "halo" refers to any one of fluorine, chlorine, bromine and iodine.

As used herein, the term "heteroatom" refers to an atom other than carbon or hydrogen. Examples of a heteroatom are N, O, S and P and Si. In particular, the term "heteroatom" refers to any one of N, O and S.

As used herein, the term "alkaryl" refers to an aryl group with an alkyl substituent. Binding is through the aryl group. The alkyl and aryl moieties of such a group are as defined herein. Non-limiting examples of alkaryl include tolyl, xylyl, butylphenyl, mesityl, ethyltolyl, methylindanyl, methylnaphthyl, methyltetrahydronaphthyl, ethylnaphthyl, dimethylnaphthyl, propylnaphthyl, butylnaphthyl, methylfluoryl and methylchrysyl. An "alkaryl" group may be substituted or unsubstituted.

As used herein, the term "aralkyl" refers to an alkyl group with an aryl substituent. Binding is through the alkyl group. The aryl and alkyl moieties of such a group are as defined herein. Non-limiting examples of aralkyl include benzyl, methylbenzyl, ethylbenzyl, dimethylbenzyl, diethylbenzyl, methylethylbenzyl, methoxybenzyl, chlorobenzyl, dichlorobenzyl, trichlorobenzyl, phenethyl, phenylpropyl, diphenylpropyl, phenylbutyl, biphenylmethyl, fluorobenzyl, difluorobenzyl, trifluorobenzyl, phenyltolylmethyl, trifluoromethylbenzyl, bis (trifluoromethyl)benzyl, propylbenzyl, tolylmethyl, fluorophenethyl, fluorenylmethyl, methoxyphenethyl, dimethoxybenzyl dichlorophenethyl, phenylethylbenzyl, isopropylbenzyl, diphenylmethyl, propylbenzyl, butylbenzyl, dimethylethylbenzyl, phenylpentyl, tetramethylbenzyl, phenylhexyl, dipropylbenzyl, triethylbenzyl, cyclohexylbenzyl, naphthylmethyl, diphenylethyl, triphenylmethyl and hexamethylbenzyl.

As used herein, the term "heterocyclylalkyl" refers to an alkyl group with a heterocyclyl substituent. Binding is through the alkyl group. The heterocyclyl and alkyl moieties of such a group are to be understood with regard to the definitions of heterocyclyl and alkyl provided herein. By way of non-limiting example, suitable heterocyclylalkyl groups include methyl, ethyl, propyl, butyl, pentyl and hexyl substituted with one or more of the heterocyclyl groups including pyrrolidinyl, tetrahydrofuranyl, morpholinyl, piperidinyl and piperazinyl.

The term "arylamino" refers to an amine group with an aryl substituent. Binding is through the amine group. Such groups have the number of carbon atoms as indicated. The aryl moiety of such a group may be substituted as defined herein, with regard to the definition of aryl. By way of non-limiting example, suitable arylamino groups include phenylamino, biphenylamino, methylphenylamino, methoxyphenylamino, tolylamino and chlorophenylamino.

As used herein, the term "alkoxy or "alkoxyl" refers to the group alkyl as defined above which contains at least one O atom, where the at least one oxgen atom is at the position where the alkoxy group is attached to the remainder of the organic compound. By way of non-limiting example, suitable alkoxy groups include, for example, methoxy (—O—$CH_3$), ethoxy (—O—$CH_2$—$CH_3$), propoxy (—O—$CH_2$—$CH_2$—$CH_3$ (straight chain alkyl) or —O—CH—$(CH_3)_2$ (branched chain alkyl)) and —O—$CH_2$—$CH_2$—O—$CH_3$. The alkoxy may be substituted or unsubstituted. In this regard, the term "haloalkoxy", as used herein, refers to "alkoxy" substituted with one or more halo i.e. one or more of F, Cl, Br or I. An example of "haloalkoxy" is —$OCF_3$.

As used herein, the term "aryloxy" refers to the group aryl as defined above which contains at least one O atom, where the at least one oxgen atom is at the position where the aryloxy group is attached to the remainder of the organic compound. By way of non-limiting example, suitable aryloxy groups include, for example, phenoxy, tolyloxy and xylyoxy. The aryloxy may be substituted or unsubstituted.

Other "compound" group definitions will be readily understandable by the skilled person based on the previous definitions of their constituent parts, and the usual conventions of nomenclature.

With respect to structural notation it would be understood that ══ refers to either a single bond or a double bond.

As used herein the term "treatment", "treat", "treating" and the like refer to the control, healing or amelioration of a disease, disorder or condition, or a decrease in the rate of advancement of a disease, disorder or condition, or defending against or inhibiting a symptom or side effect, reducing the severity of the development of a symptom or side effect, and/or reducing the number or type of symptoms or side effects suffered by an animal subject, as compared to not administering a pharmaceutical composition comprising a compound of the invention. The term "treatment" encompasses use in a palliative setting.

The term "prevention", "prevent", "preventing" and the like as used herein are intended to encompass treatments that are used to delay or slow down the development of a disease, disorder or condition, or symptom or side effect thereof.

With regard to "prevention" and "treatment", the term "effective amount", as used herein, refers to an amount when administered to an animal, achieves a desired effect. For example, an effective amount of a composition disclosed herein is an amount that prevents or treats an infectious disease in a pig. The exact total effective amount depends on the purpose of the treatment and other factors including the animal subject (e.g. cattle versus pig), route of administration, body weight and severity of the disease, disorder or condition.

Throughout this disclosure, various aspects, components and embodiments can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6, unless where integers are required or implicit from context. This applies regardless of the breadth of the disclosed range. Where specific values are required, these will be indicated in the specification.

BRIEF DESCRIPTION OF DRAWINGS

FIG. 11 shows activity against *C. difficile* of berberine sulfate alone at at concentration of 128 µg/mL.

FIG. 12 shows activity against *C. difficile* of metronidazole alone at a concentration of 0.25 µg/mL.

FIG. 13 shows activity against *C. difficile* of berberine sulfate (128 µg/mL) and metronidazole (0.25 µg/mL) together.

Figure 1:
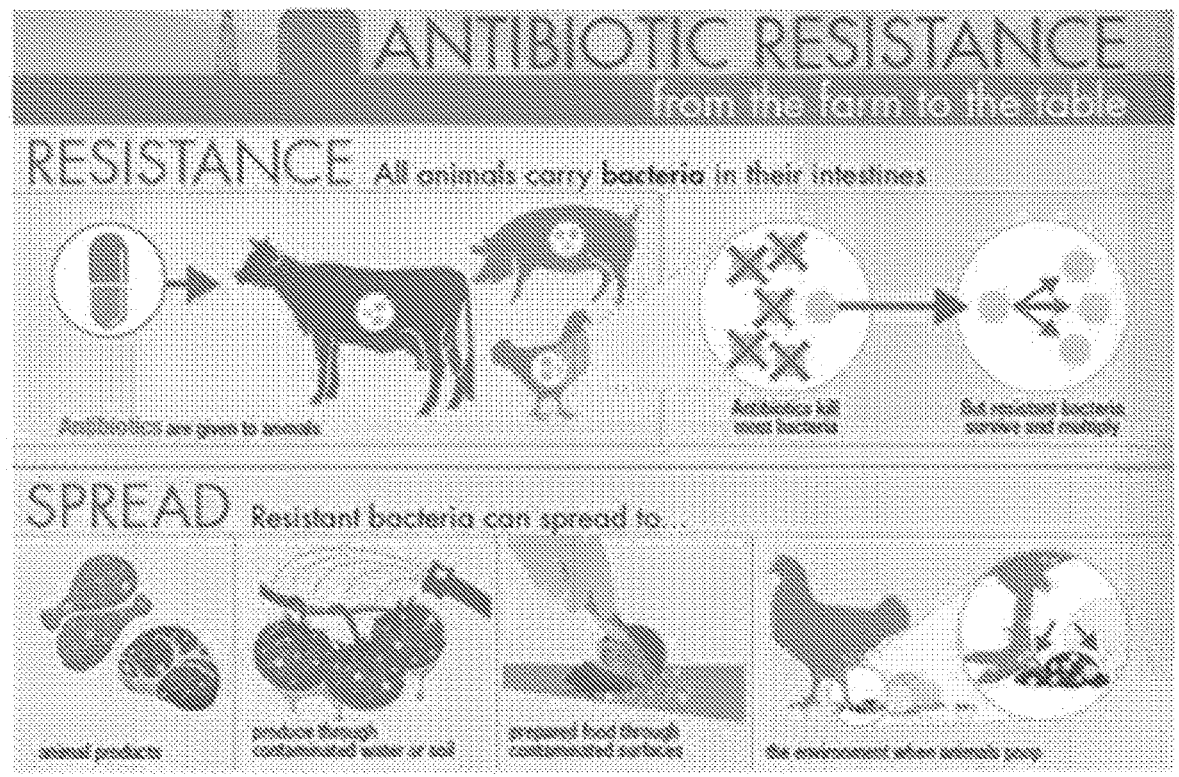
FIG. 1 depicts the spread of AMR from food-producing animal to human. Figure is taken from https://www.cdc.gov/foodsafety/challenges/from-farm-to-table.html.

Specific embodiments of the disclosure are described below. It will be appreciated that these embodiments are illustrative and not restrictive.

DETAILED DESCRIPTION OF INVENTION

Methods for the Prevention and/or Treatment of an Infectious Disease

The present disclosure relates to a method for the prevention and/or treatment of an infectious disease in a mammal, wherein the method comprises administering to the mammal a nitroimidazole.

Animal Subject

The present disclosure is directed to animal subjects that are mammals. Preferably, the mammal is human. The mammal is preferably non-human. The non-human mammal preferably is a horse, dog, cat, sheep, cattle, pig or primate. Preferably, the non-human mammal is a food-producing animal. The food-producing animal is preferably a pig. The mammal preferably is a horse, dog, cat, sheep, cattle, pig or primate.

Nitroimidazole Compounds

The nitroimidazoles of the present disclosure are in accordance with the general formula (I) shown in Table 1 and below for ease of reference.

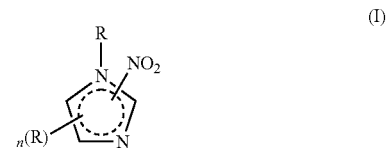

(I)

With respect to Formula (I), n is 0, 1 or 2; and R is independently selected from hydrogen and a substituent as defined herein.

Further, it would be understood that the nitroimidazoles of the present disclosure encompass compounds of general Formula (I), isomeric forms, acceptable salts, solvates thereof, and prodrugs thereof.

The nitroimidazole compounds of the present disclosure can be classified into subgroups by the substitution position of the nitro group in the ring. The subgroups are 5-nitroimidazole compounds; 4-nitroimidazole compounds; and 2-nitroimidazole compounds. The subgroups are structurally related and share similar characteristics and similar bioactivities. General formulae for these subgroups are shown in Table 1 and below for ease of reference.

2-Nitroimidazole Compounds

Preferably, the nitroimidazole is a 2-nitroimidazole. Preferably, the nitroimidazole is a 2-nitroimidazole of Formula (Ia):

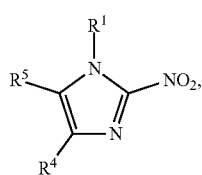

(Ia)

wherein $R^1$, $R^4$ and $R^5$ are each independently hydrogen or a substituent as defined herein.

Preferably, $R^1$, $R^4$ and $R^5$ are each independently selected from: hydrogen, alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl, wherein any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, $R^1$, $R^4$ and $R^5$ are each independently selected from: hydrogen, alkyl, cycloalkyl, oxaalkyl, cyclooxaalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl, wherein any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, R$^1$, R$^4$ and R$^5$ are each independently selected from: hydrogen alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, heterocyclyl, alkaryl, aralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, alkylhetereocyclyl and heterocyclylalkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, alkynyl, aryl, heteroaryl, heterocyclyl, alkaryl, aralkyl, alkylhetereocyclyl and heterocyclylalkyl.

Preferably, R$^1$, R$^4$ and R$^5$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio, heterocycylthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, R$^1$, R$^4$ and R$^5$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, R$^1$, R$^4$ and R$^5$ are each independently selected from: hydrogen, alkyl, cycloalkyl, aryl, heteroaryl, heterocyclyl, halo, nitro, cyano (—CN), carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, aryl, heteroaryl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, aryl, heteroaryl, hetereocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, any one of the groups alkyl, cycloalkyl, aryl, heteroaryl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, aryl, heteroaryl, hetereocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, R$^1$, R$^4$ and R$^5$ are each independently selected from: hydrogen, alkyl, cycloalkyl, heterocyclyl, halo, nitro, cyano (—CN), carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, disulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy) alkyl, alkylamino, dialkylamino, hydroxyalkylamino, aralkyloxy, mercaptoalkyl or thioalkyl, alkylthio, heterocyclylthio, alkylsulfonyl, wherein any one of the groups alkyl, cycloalkyl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, heterocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, any one of the groups alkyl, cycloalkyl, heterocyclyl, carboxy or carboxyl (—C(═O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino) alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, heterocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, the heterocyclyl group is further substituted with any one or more of alkyl, cycloalkyl, heterocyclyl, halo, nitro, —CN, —C(═O)OR$^x$, —C(═O)R$^x$, —C(═O)NR$^x$R$^y$, —OR$^x$, —NR$^x$R$^Y$, —NR$^x$C(═O)R$^y$, —NR$^x$C(═O)OR$^y$, —NR$^x$C(═S)OR$^y$, —NR$^x$C(═O)NR$^y$R$^z$, —NR$^x$C(═S)NR$^y$R$^z$, —NR$^v$C(═NR$^x$)NR$^y$R$^z$, —OH, ═O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, R$^1$, R$^4$ and R$^5$ are connected to any other one of atoms of the imidazole heterocycle, where permissible, so as to form a ring structure. The ring structure is preferably substituted. Preferably, the ring structure is derivatised.

The 2-nitroimidazole is preferably selected from the group consisting of: azomycin, misonidazole, benzindazole, an acceptable salt thereof and a prodrug thereof. Preferably, the 2-nitroimidazole is selected from the group consisting of: azomycin, misonidazole and benzindazole.

4-Nitroimidazole Compounds

Preferably, the nitroimidazole is a 4-nitroimidazole. Preferably, the nitroimidazole is a 4-nitroimidazole of Formula (Ib):

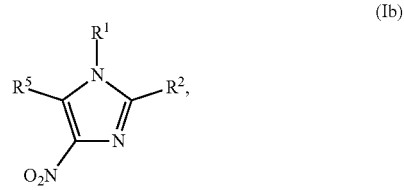

(Ib)

wherein R$^1$, R$^2$ and R$^5$ are each independently absent or a substituent as defined herein.

Preferably, R$^1$, R$^2$ and R$^5$ are each independently selected from: hydrogen, alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, halo, nitro, cyano (—CN), carboxy or carboxyl (—C(═O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocyclylthio, heteroarylthio, alkylsulfonyl, arylsulfonyl, wherein any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(═O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (═O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, oxaalkyl, cycloaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, R$^1$, R$^2$ and R$^5$ are each independently selected from: hydrogen, alkyl, cycloalkyl, oxaalkyl, cyclooxaalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl, wherein any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate) alkyl, alkylurea, alkylthiourea, alkylguanidino, hydroxyalkyl, alkoxy, aryloxy, alkoxyalkyl, (alkylamino) alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocycylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heterocyclyl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocyclthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylheterocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^x$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylheterocyclyl and heterocyclylalkyl.

Preferably, R$^1$, R$^2$ and R$^5$ are each independently selected from: hydrogen alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, alkylheterocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocyclthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylheterocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocyclthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, heterocyclyl, alkaryl, aralkyl, alkylheterocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, alkylheterocyclyl and heterocyclylalkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylheterocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocyclthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, heterocyclyl, alkaryl, aralkyl, alkylheterocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, alkylheterocyclyl and heterocyclylalkyl.

Preferably, R$^1$, R$^2$ and R$^5$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio, heterocyclthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, R$^1$, R$^2$ and R$^5$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocyclthio, alkylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, R$^1$, R$^2$ and R$^5$ are each independently selected from: hydrogen, alkyl, cycloalkyl, aryl, heteroaryl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino) alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^x$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, any one of the groups alkyl, cycloalkyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino) alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^x$C(=NR$^x$) NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, R$^1$, R$^2$ and R$^5$ are each independently selected from: hydrogen, alkyl, cycloalkyl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy) alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S) NR$^y$R$^z$, —NR$^x$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, any one of the groups alkyl, cycloalkyl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino) alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O) NR$^y$R$^z$, —NR$^x$C(=S)NR$^y$R$^z$, —NR$^x$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, the heterocyclyl group is further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, R$^1$, R$^2$ and R$^5$ are connected to any other one of atoms of the imidazole heterocycle, where permissible, so as to form a ring structure. The ring structure is preferably substituted. Preferably, the ring structure is derivatised.

The 4-nitroimidazole is preferably selected from the group consisting of: isometronidazole, azathioprine, 4-nitromegazol, CGI-17341, PA-824, an acceptable salt thereof and a prodrug thereof. Preferably, the 4-nitroimidazole is selected from the group consisting of: isometronidazole, azathioprine, 4-nitromegazol, CGI-17341 and PA-824.

Isometronidazole is the 4-nitro isomer of metronidazole (which is a 5-nitroimidazole). Azathioprine is an example of a 1,5-disubstituted-4-nitroimidazole where R$^1$ is Me; and R$^5$ is heteroarylthio, wherein the heteroarylthio R$^5$ substituent is a purinylthio substituent. An example of a 1,2-disubstituted-4-nitroimidazole is 4-nitromegazol, where R$^1$ is Me; and R$^2$ is an (amino)heteroaryl group where the (amino)heteroaryl group is a 2-amino-1,3,4-thiadiazolyl. CGI-I17341 and PA-824 are examples of bicyclic 4-nitromidazoles where the R$^1$ substituent is connected with the C-2carbon atom of the imidazole ring so as to form a ring structure, which is substituted by an ethyl alkyl group (CGI-I17341) or substituted arylmethoxy group (PA-824). The present disclosure also contemplates 1,2,5-trisubstituted-4-nitromidazoles.

Figure 6:
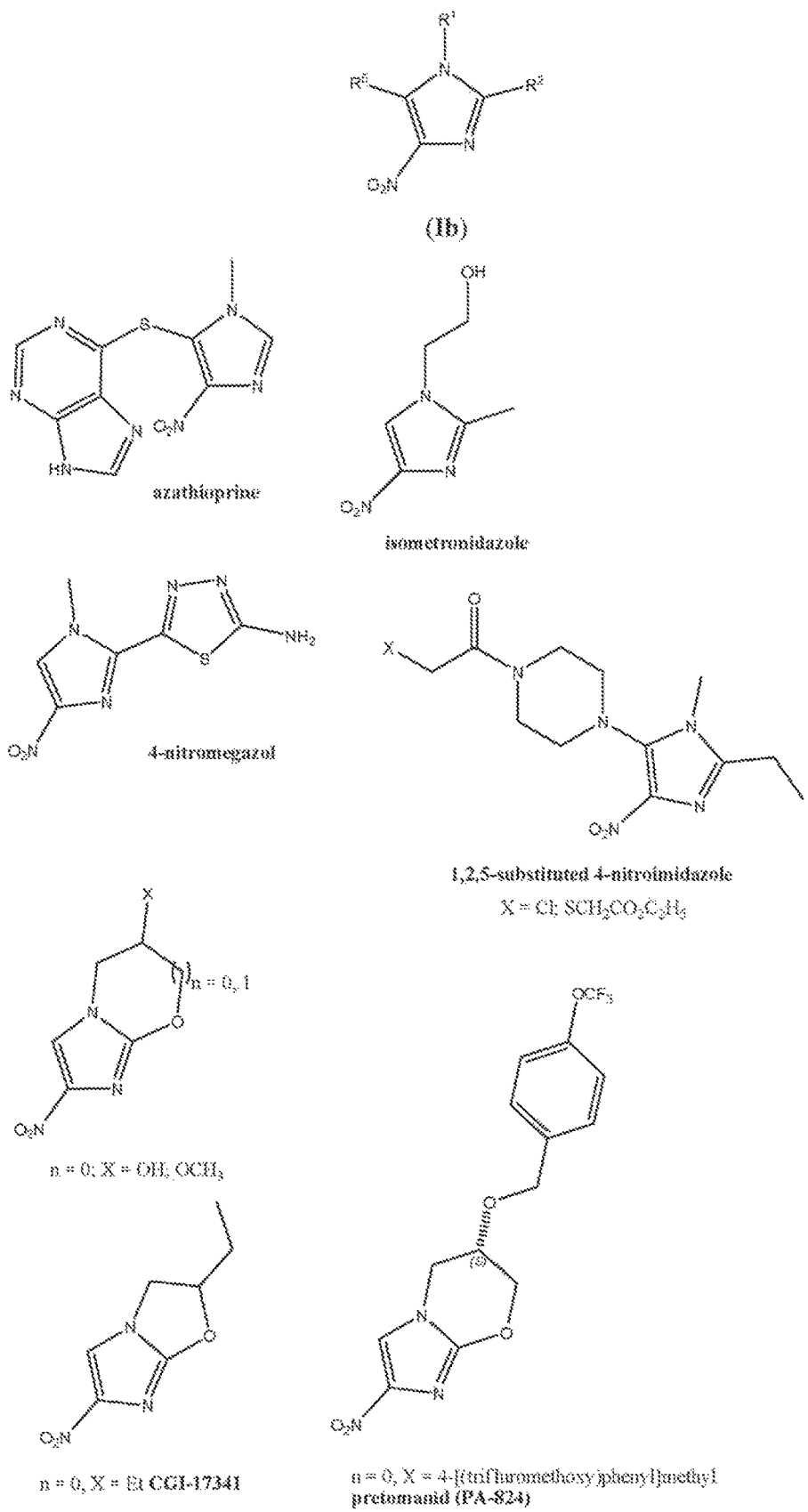
FIG. 6 depicts a general formula for 4-nitroimidazoles and representative examples. Reference molecular structures and compound names/types are shown.

Molecular structures for isometronidazole, azathioprine, 4-nitromegazol, CGI-I17341 and PA-824 and representative 1,2,5-trisubstituted-4-nitromidazoles are shown in FIG. 6.

5-Nitroimidazole Compounds

Preferably, the nitroimidazole is a 5-nitroimidazole. Preferably, the nitroimidazole is a 5-nitroimidazole of Formula (Ic):

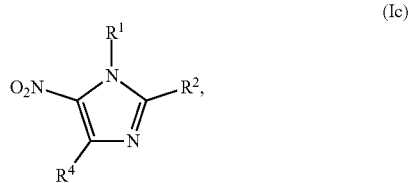

(Ic)

wherein R$^1$, R$^2$ and R$^4$ are each independently absent or a substituent as defined herein.

Preferably, R$^1$, R$^2$ and R$^4$ are each independently selected from: hydrogen, alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocyclylthio, heteroarylthio, alkylsulfonyl, arylsulfonyl, wherein any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocyclylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, oxaalkyl, cyclooxaalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocylthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^V$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, R$^1$, R$^2$ and R$^4$ are each independently selected from: hydrogen, alkyl, cycloalkyl, oxaalkyl, cyclooxaalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocylthio, heteroarylthio, alkylsulfonyl, arylsulfonyl, wherein any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocylthio, heteroarylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^V$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, any one of the groups alkyl, cycloalkyl, alkenyl, cycloalkenyl, oxaalkenyl, cyclooxaalkenyl, alkadienyl, cycloalkadienyl, oxaalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, heteroaralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl (amino)heteroaryl, (amino)heterocyclyl, alkylamino, dialkylamino, hydroxyalkylamino, arylamino, diarylamino, heteroarylamino, heterocyclylamino, heteroaryloxy, aralkyloxy, mercaptoalkyl or thioalkyl, alkylthio, arylthio, heterocylthio, heteroarylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, heteroaralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^V$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, heteroaralkyl, alkylhetereocyclyl and heterocyclylalkyl.

Preferably, R$^1$, R$^2$ and R$^4$ are each independently selected from: hydrogen alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino) alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, alkylhetereocyclyl and heterocyclylalkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, alkylhetereocyclyl, heterocyclylalkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino) alkyl, (dialkylamino)alkyl, (cycloalkylamino)alkyl, (haloalkoxy)alkyl, (amino)aryl, (amino)heterocyclyl, alkylamino, dialkylamino, hydroxyalkylamino, arylamino, diarylamino, heterocyclylamino, aralkyloxy, mercaptoalkyl or thioalkyl, alkylthio, arylthio, heterocycylthio, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, alkylhetereocyclyl, heterocyclylalkyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S) NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl, aralkyl, alkylhetereocyclyl and heterocyclylalkyl.

Preferably, R$^1$, R$^2$ and R$^4$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio, heterocycylthio, alkylsulfonyl, arylsulfonyl, wherein any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino) alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, any one of the groups alkyl, cycloalkyl, alkenyl, cycloalkenyl, alkadienyl, cycloalkadienyl, cyclooxaalkadienyl, alkynyl, aryl, heteroaryl, heterocyclyl, carboxy or carboxyl (—C(=O)OH), alkylcarbonyl, arylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, alkaryl, aralkyl, haloalkyl, haloalkoxy, nitroalkyl, (cyano)alkyl, carboxyalkyl, (alkylcarbonyl)alkyl, (arylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, aryloxy, alkoxyalkyl, (alkylamino)alkyl, (dialkylamino)alkyl, (cycloalkylamino)alkyl, (haloalkoxy)alkyl, (amino)aryl, alkylamino, dialkylamino, hydroxyalkylamino, arylamino, diarylamino, aralkyloxy, mercaptoalkyl or thioalkyl, alkylthio, arylthio,, alkylsulfonyl, arylsulfonyl is further substituted with any one or more of alkyl, cycloalkyl, alkenyl, cycloalkenyl, alkadienyl, cycloalkadienyl, alkynyl, aryl, heteroaryl, hetereocyclyl, alkaryl, aralkyl, -halo, nitro, —CN, C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl, heterocyclyl, alkaryl and aralkyl.

Preferably, R$^1$, R$^2$ and R$^4$ are each independently selected from: hydrogen, alkyl, cycloalkyl, alkenyl, cycloalkenyl, alkadienyl, cycloalkadienyl, alkynyl, aryl, heteroaryl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, alkenyl, cycloalkenyl, alkadienyl, cycloalkadienyl, cylooxaalkadienyl, alkynyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, any one of the groups alkyl, cycloalkyl, alkenyl, cycloalkenyl, alkadienyl, cycloalkadienyl, cylooxaalkadienyl, alkynyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, alkenyl, cycloalkenyl, alkadienyl, cycloalkadienyl, alkynyl, aryl, heteroaryl, hetereocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^y$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, alkenyl, cycloalkenyl, alkadienyl, cycloalkadienyl, alkynyl, aryl, heteroaryl and heterocyclyl.

Preferably, R$^1$, R$^2$ and R$^4$ are each independently selected from: hydrogen, alkyl, cycloalkyl, aryl, heteroaryl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, aryl, heteroaryl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C (=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, any one of the groups alkyl, cycloalkyl, aryl, heteroaryl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, aryl, heteroaryl, heteroecyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl, aryl, heteroaryl and heterocyclyl.

Preferably, R$^1$, R$^2$ and R$^4$ are each independently selected from: hydrogen, alkyl, cycloalkyl, heterocyclyl, halo, nitro, cyano (—CN), carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic acid, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, aralkyloxy, mercaptoalkyl or thioalkyl, alkylthio, heterocycylthio, alkylsulfonyl, wherein any one of the groups alkyl, cycloalkyl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is optionally further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, any one of the groups alkyl, cycloalkyl, heterocyclyl, carboxy or carboxyl (—C(=O)OH), alkylcarbonyl, amido, carboxamido, amino, carbamic acid, carbamate or urethane, thiocarbamate or thiourethane, urea, thiourea, guanidino, hydroxy or hydroxyl (—OH), oxo (=O), mercapto or thiol (—SH), sulfide, disulfide, sulfonic, sulfonyl, sulfoxide, sulfinylamido, sulfonamido, haloalkyl, haloalkoxy, nitroalkyl, (cyano)alkyl, carboxyalkyl, (alkylcarbonyl)alkyl, (amido)alkyl, (carboxamido)alkyl, (amino)alkyl, (carbamic acid)alkyl, (carbamate)alkyl, (thiocarbamate)alkyl, alkylurea, alkylthiourea, alkylguanidino, hydroxyalkyl, alkoxy, alkoxyalkyl, (alkylamino)alkyl, (dialkylamino)alkyl, (cycloalkylamino)alkyl, (haloalkoxy)alkyl, alkylamino, dialkylamino, hydroxyalkylamino, mercaptoalkyl or thioalkyl, alkylthio, alkylsulfonyl is further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, the heterocyclyl group is further substituted with any one or more of alkyl, cycloalkyl, heterocyclyl, halo, nitro, —CN, —C(=O)OR$^x$, —C(=O)R$^x$, —C(=O)NR$^x$R$^y$, —OR$^x$, —NR$^x$R$^Y$, —NR$^x$C(=O)R$^y$, —NR$^x$C(=O)OR$^y$, —NR$^x$C(=S)OR$^y$, —NR$^x$C(=O)NR$^y$R$^z$, —NR$^x$C(=S)NR$^y$R$^z$, —NR$^v$C(=NR$^x$)NR$^y$R$^z$, —OH, =O, —SH, —SO$_q$R$^x$, R$^x$SO$_2$R$^y$, —SO$_q$NR$^x$R$^y$, and —NR$^x$SO$_q$R$^y$ wherein q is 0, 1, 2 or 3, R$^v$, R$^x$, R$^y$ and R$^z$ are the same or different and each independently selected from hydrogen, alkyl, cycloalkyl and heterocyclyl.

Preferably, R$^1$, R$^2$ and R$^4$ are connected to any other one of atoms of the imidazole heterocycle, where permissible, so as to form a ring structure. The ring structure is preferably substituted. Preferably, the ring structure is derivatised.

The 5-nitroimidazole is preferably selected from the group consisting of: metronidazole; azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole, tinidazole, an acceptable salt thereof and a prodrug thereof. Preferably, the 5-nitroimidazole is selected from the group consisting of: metronidazole; azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole and tinidazole.

Preferably, the 5-nitromidazole is in accordance with Formula (Ici) as shown in Table 2, where the R$^1$ substituent is varied; R$^2$ is methyl; and R$^4$ is H.

TABLE 2

Representative 5-nitroimidazoles varying at the 1-position

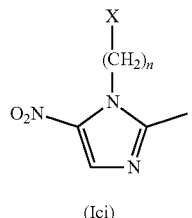

(Ici)

| Compound | N | X |
| --- | --- | --- |
| Metronidazole (Mtz) | 2 | OH |
| Mtz methyl ether | 2 | OMe |
| Mtz acetate | 2 | OC(=O)Me |
| Mtz benzoate | 2 | O(C=O)Ph |
| Bamnidazole | 2 | O(=O)NH$_2$ |
| Carnidazole | 2 | NHC(=S)OMe |
| Dimetridazole | 1 | H |
| Nimorazole | 2 | morpholinyl |
| Panidazole | 2 | pyridin-4-yl |
| Ternidazole | 3 | OH |
| Tinidazole | 2 | SO$_2$Et |

Figure 7:
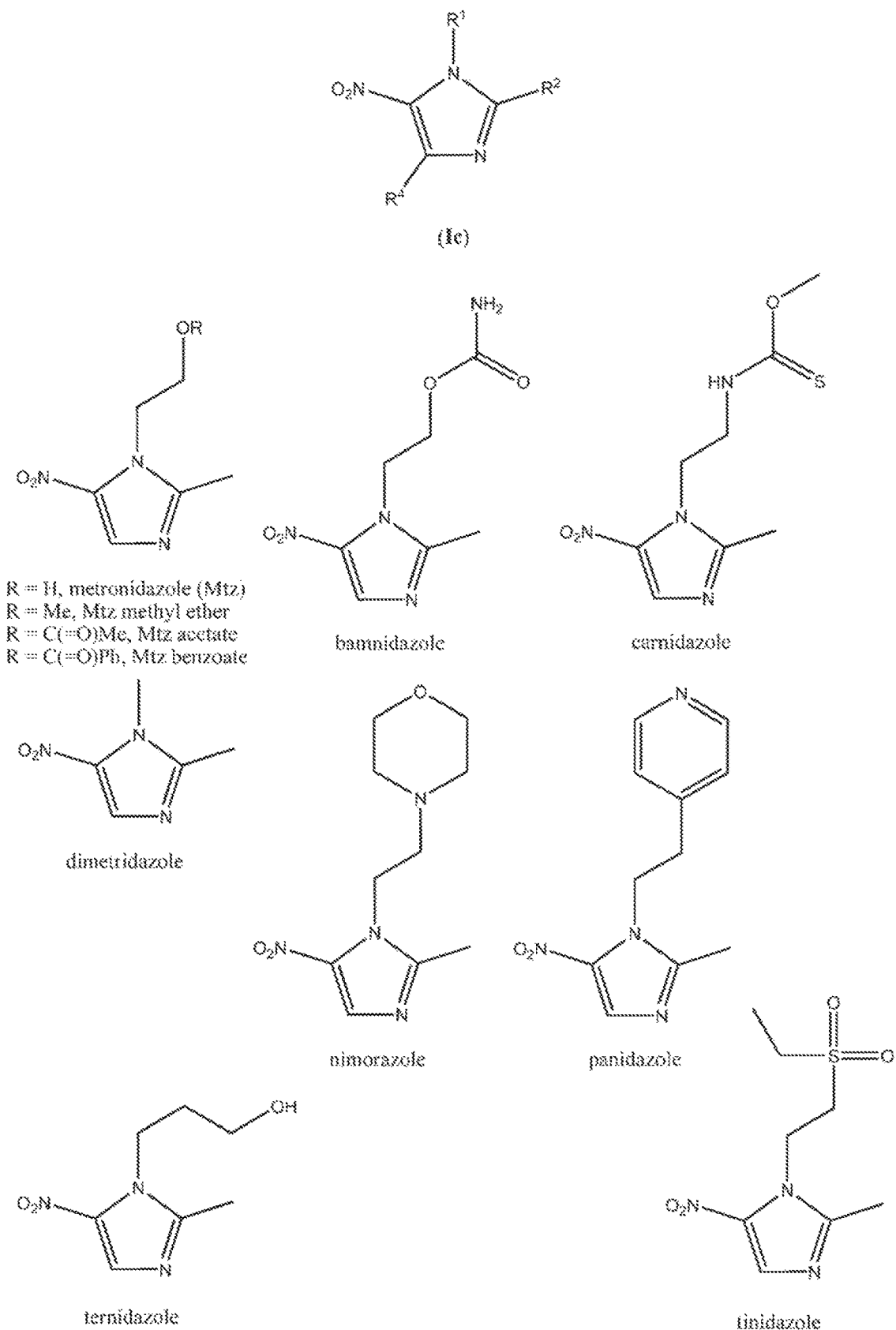
FIG. 7 depicts a general formula for 5-nitroimidazoles, Formula (Ic), and representative examples of 5-nitroimidazoles where the $R^1$ substituent is varied ($R^2$ is methyl; $R^4$ is H). Reference molecular structures and compound names are shown.

Molecular structures for the compounds shown in Table 2 are depicted in FIG. 7.

Thus, the 5-nitrominidazole is preferably selected from the group consisting of: metronidazole, metronidazole methyl ether, metronidazole acetate, bamnidazole; carnidazole; dimetridazole; nimorazole; panidazole; ternidazole and tinidazole.

Figure 8:
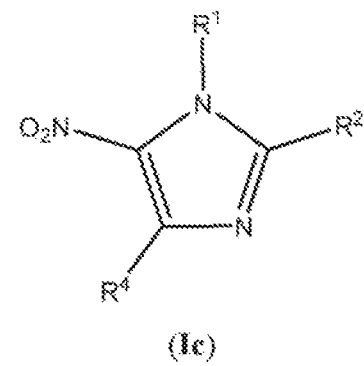
FIG. 8 depicts a general formula for 5-nitroimidazoles, Formula (Ic), and representative examples of 5-nitroimidazoles where the $R^1$ hydroxyethyl substituent is varied at the 2 position ($R^2$ is methyl; $R^4$ is H). Reference molecular structures and compound names are shown.
Figure 8:
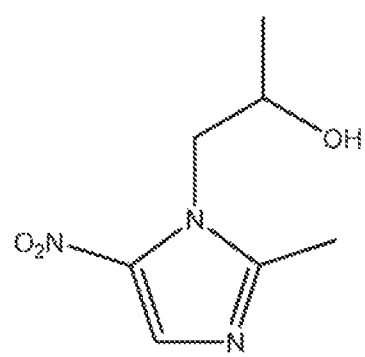
Figure 8:
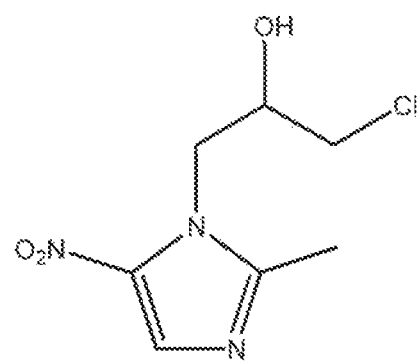

Preferably, the 5-nitroimidazole is where the $R^1$ hydroxyethyl substituent is varied at the 2 position; $R^2$ is methyl; and $R^4$ is H. The 5-nitroimidazole is preferably secnidazole or ornidazole. The molecular structures for secnidazole and ornidazole are shown in FIG. 8.

Preferably, the 5-nitroimidazole is where the $R^2$ substituent is varied; $R^1$ is Me; and $R^4$ is H.

Figure 9:
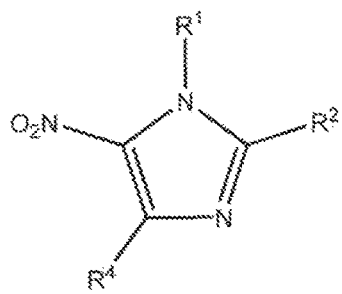
FIG. 9 depicts a general formula for 5-nitroimidazoles, Formula (Ic), and representative examples of 5-nitroimidazoles where the $R^2$ substituent is varied ($R^1$ is Me; $R^4$ is H). Reference molecular structures and compound names are shown.
Figure 9:
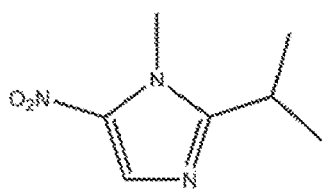
Figure 9:
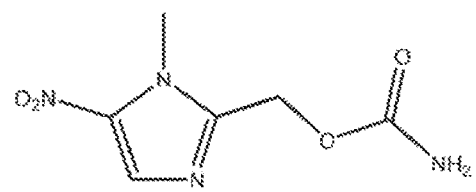
Figure 9:
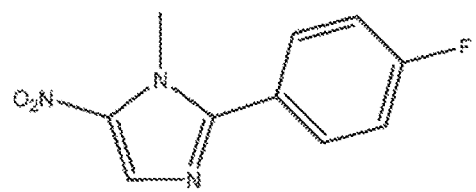
Figure 9:
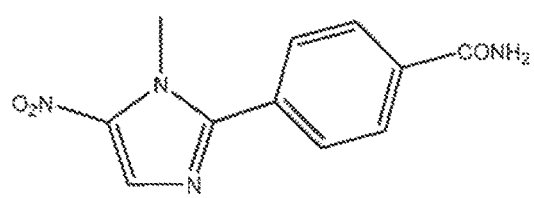
Figure 9:
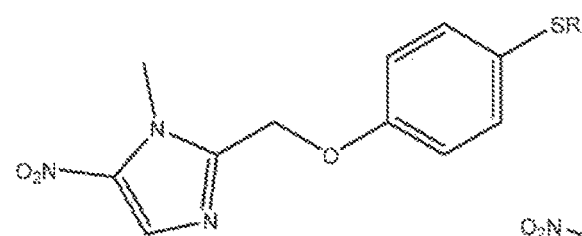
Figure 9:
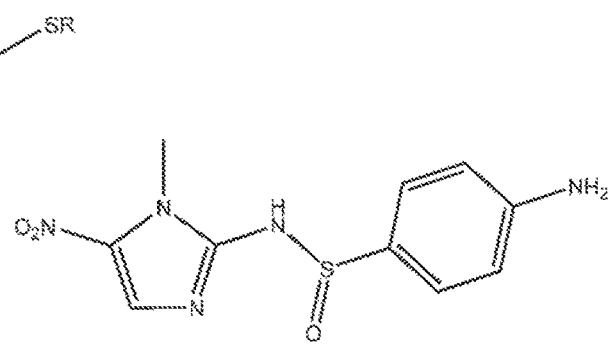
Figure 9:
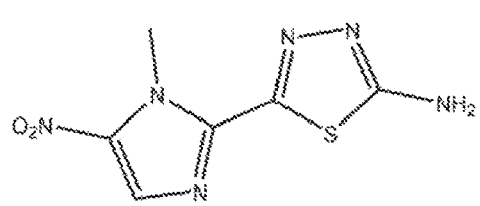
Figure 9:
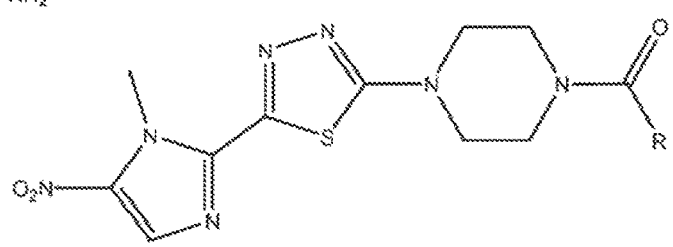

The 5-nitroimidazole is preferably selected from the group consisting of: ipronidazole, ronidazole, "MF" nitroimidazole, "MCA" nitroimidazole, fexinidazole, azanidazole, sulphimidazole, 5-nitromegazol. The molecular structures of these compounds are shown in FIG. 9.

Figure 10:
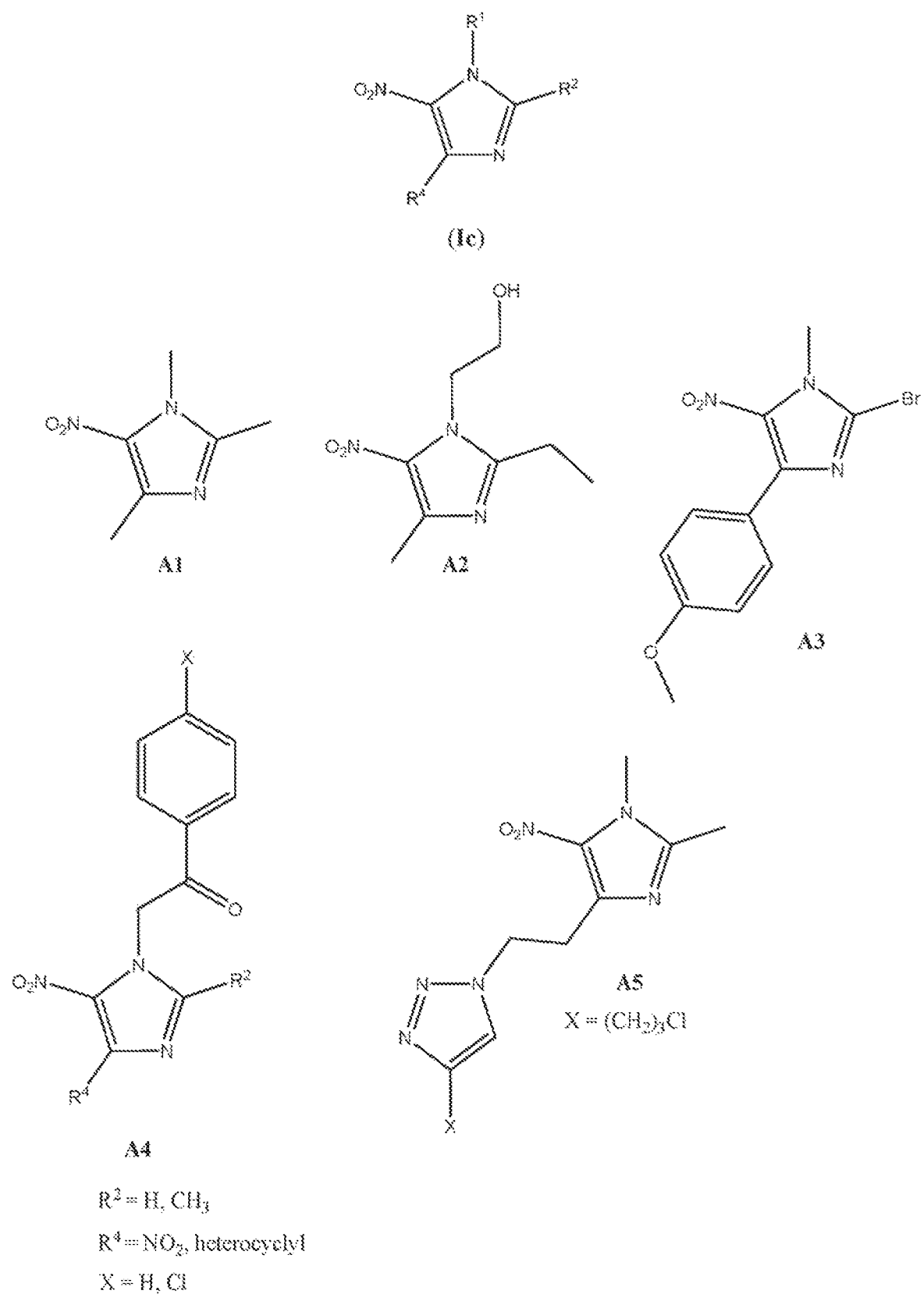
FIG. 10 depicts a general formula for 5-nitroimidazoles, Formula (Ic), and representative examples of 5-nitroimidazoles where the $R^1$, $R^2$ and $R^4$ positions are all substituted (reference structures A1 to A5).

Preferably, the 5-nitroimidazole is where the $R^1$, $R^2$ and $R^4$ positions are all substituted and are all varied. Molecular structures of representative 1,2,4-trisubstituted-5-nitroimidazoles are shown in FIG. 10.

Further examples of 5-nitroimidazole compounds are disclosed in Kapoor et al. 2003; Upcroft et al. 2006, Miyamoto et al. 2013; Mital 2009; Kim et al. 2009; Mathias 2017. The disclosure of these compounds and the subject matter relating to these compounds is hereby incorporated by reference. Thus, the term 5-nitroimidazole includes, but is not limited to the compounds disclosed in the above references. It would also be understood that the term "5-nitroimidazole" as used herein also encompasses, where permitted, all isomeric forms, racemates, amorphous or crystalline forms, acceptable salts, solvates thereof, and prodrugs thereof of the compounds disclosed in the above references.

Preferably, the 5-nitroimidazole is metronidazole.

Infectious Disease where *Clostridium* is Causative Agent

Preferably, the infectious disease is caused by bacteria from the genus *Clostridium*. The infectious disease is preferably caused by an antibiotic-resistant bacterial strain from the genus *Clostridium*. Preferably, the bacteria are *C. difficile*. The infectious disease is preferably diarrhoea and the animal is human. Preferably, the infectious disease is colitis and the animal is human.

Administration of Nitroimidazole Formulations

Preferably, the method further comprises co-administering one or more agents suitable for the prevention and/or treatment of an infectious disease in a mammal. Non-limiting examples of agents suitable for the prevention and/or treatment of an infectious disease in a mammal (anti-infective agents) are selected from the group comprising: β-lactams, macrolides, quinolones, tetracyclines, sulfonamides, aminoglycosides, glycopeptides, lincomycins, and polymxins. Representative examples of β-lactams are selected from the group comprising: penicillins, cephalosporins, and carbapanems.

Agents or medications for the prevention and/or treatment of infectious disease are described, for example, in Goodman & Gilman's 2005, particularly in Section VII: Chemotherapy of Parasitic Infections, pages 1021 to 1093; and Section VIII: Chemotherapy of Microbial Disease, pages 1095 to 1314. It will be understood that the present disclosure encompasses methods for the prevention and/or treatment of an infectious disease in an animal comprising co-administration of one or more agents suitable for the prevention and/or treatment of an infectious disease, an isomeric form, a racemate, an amorphous or a crystalline form, an acceptable salt, a prodrug, or a solvate thereof, or a combination thereof.

Thus, the compounds of the present disclosure may be applied solely as a single agent or as a combination (i.e. where one or more compounds are administered to a subject). The application may involve, in addition, administration of one or more other substances, preventions and/or treatments. Such conjoint treatment may be achieved by way of the simultaneous, sequential or separate administration of the individual components of the prevention and/or treatment.

The individual components of such combinations can be administered separately at different times during the course of therapy or concurrently in divided or single combination forms. The present disclosure is therefore to be understood as embracing all such regimes of simultaneous or alternating prevention and/or treatment and the term "administering" is to be interpreted accordingly.

It will be understood that the scope of combinations of the compounds of this disclosure with other agents includes in principle any combination with any agent or composition suitable for the prevention and/or treatment of an infectious disease. Agents or medications for the prevention and/or treatment of infectious disease are described, for example, in Goodman and Gilman's. It will be understood that the present disclosure encompasses combinations comprising isomeric forms, racemates, amorphous or crystalline forms, solvates, acceptable salts, solvates of said salts, or prodrugs or combinations thereof of agents or medications suitable for the prevention and/or treatment of infectious disease.

Preferably, the one or more agents suitable for the prevention and/or treatment of an infectious disease in a mammal is one or more antimicrobial compounds. The one or more additional compounds is a berberine alkaloid. Preferably, the berberine alkaloid is selected from berberine chloride, berberine iodide or berberine sulfate. The berberine alkaloid is preferably berberine chloride. Preferably, the berberine alkaloid is berberine iodide. The berberine alkaloid is preferably berberine sulfate.

It will be understood that references to an antimicrobial compound herein (for example a berberine alkaloid), encompass, where permitted, all isomeric forms, racemates, amorphous or crystalline forms, acceptable salts, solvates thereof, and prodrugs thereof.

Preferably, the nitroimidazole and the berberine alkaloid are administered together. The administration preferably occurs via the water of the mammal. Preferably, the administration preferably occurs via the feed of the mammal. The feed is preferably in the form of a mash; granule; crumble or a pellet. Preferably the feed is in the form of a mash. The feed is preferably in the form of a granule. Preferably, the feed is the form of a crumble. The feed is preferably in the form of a pellet.

The dosage of nitroimidazole administered to the subject may be in the range of about 5 to 100 mg/kg of body weight; about 10 to 95 mg/kg of body weight; about 15 to about 90 mg/kg of body weight; about 20 to about 85 mg/kg of body weight; about 25 to about 80 mg/kg of body weight; about 30 to about 75 mg/kg of body weight; about 35 to about 70 mg/kg of body weight; about 40 to about 65 mg/kg of body weight; about 45 to about 60 mg/kg of body weight; or about 50 to about 55 mg/kg of body weight. The dosage of nitroimidazole administered to the subject may be 5 mg/kg of body weight, 10 mg/kg of body weight, 15 mg/kg of body weight, 20 mg/kg of body weight, 25 mg/kg of body weight, 30 mg/kg of body weight, 35 mg/kg of body weight, 40 mg/kg of body weight, 45 mg/kg of body weight, 50 mg/kg of body weight, 55 mg/kg of body weight, 60 mg/kg of body weight, 65 mg/kg of body weight, 70 mg/kg of body weight, 75 mg/kg of body weight, 80 mg/kg of body weight, 85 mg/kg of body weight, 90 mg/kg of body weight or 100 mg/kg of body weight. In one preferred example, the nitroimidazole is administered to the subject at a dosage of 25 mg/kg of body weight (see Example 2 which is mouse study).

The dosage of berberine alkaloid administered to the subject may be in the range of about 5 to 100 mg/kg of body weight; about 10 to 95 mg/kg of body weight; about 15 to about 90 mg/kg of body weight; about 20 to about 85 mg/kg of body weight; about 25 to about 80 mg/kg of body weight; about 30 to about 75 mg/kg of body weight; about 35 to about 70 mg/kg of body weight; about 40 to about 65 mg/kg of body weight; about 45 to about 60 mg/kg of body weight; or about 50 to about 55 mg/kg of body weight. The dosage of berberine alkaloid administered to the subject may be 5 mg/kg of body weight, 10 mg/kg of body weight, 15 mg/kg of body weight, 20 mg/kg of body weight, 25 mg/kg of body weight, 30 mg/kg of body weight, 35 mg/kg of body weight, 40 mg/kg of body weight, 45 mg/kg of body weight, 50 mg/kg of body weight, 55 mg/kg of body weight, 60 mg/kg of body weight, 65 mg/kg of body weight, 70 mg/kg of body weight, 75 mg/kg of body weight, 80 mg/kg of body weight, 85 mg/kg of body weight, 90 mg/kg of body weight or 100 mg/kg of body weight. In one preferred example, the berberine alkaloid is administered to the subject at a dosage of 25 mg/kg of body weight. In another preferred example, the berberine alkaloid is administered to the subject at a dosage of 50 mg/kg of body weight (see Example 2 which is mouse study).

Preferably, the nitroimidazole and the berberine alkaloid are administered in a ratio of between about 1:10 and 10:1 by dosage (mg of active agent/kg of mammal body weight). The ratio of nitroimidazole:berberine alkaloid is preferably about: 1:10; 1:9; 1:8; 1:7; 1:6; 1:5; 1:4; 1:3; 1:2; 1:1; 2:1; 3:1; 4:1; 5:1; 6:1; 7:1; 8:1; 9:1 and 10:1. Preferably, the ratio of nitroimidazole:berberine alkaloid is about 1:1. The ratio of nitroimidazole:berberine alkaloid is preferably about 1:2.

Preferably, there is a synergistic effect between the nitroimidazole and the berberine alkaloid.

Preferably, the method further comprises administration of an additive that masks the bitter flavour of the berberine alkaloid.

Nitroimidazole Compositions, Animal Feeds and Animal Feed Additives

The present disclosure contemplates the inclusion of a nitroimidazole in compositions either as a single agent or in combination with other active ingredients i.e. combination compositions. The compositions may be formulated for administration to an animal subject. The present disclosure also contemplates the inclusion of a nitroimidazole or nitroimidazole compositions in animal feeds intended for intake by an animal. Nitroimidazole compounds or nitroimidazole compositions of the present disclosure may be formulated for administration in animal feeds. Nitroimidazole compounds or nitroimidazole compositions of the present disclosure may be formulated as feed additives. The present disclosure also contemplates animal feeds such nitroimidazole feed additives. The nitroimidazole compounds, compositions, animal feeds or animal feed additives of the present disclosure may have application in various methods, dosing regimens and uses. In this regard, the nitroimidazole compounds, compositions, animal feeds or animal feed additives may improve or maintain animal health; improve or maintain gastrointestinal health; improve growth performance; improve weight gain; reduce feed conversion ratio (FCR); or improve feed quality and yield (e.g. meat quality and yield in a food-producing animal).

Nitroimidazole Compositions

The present disclosure also relates to a composition comprising a nitroimidazole. The present disclosure also relates to a composition comprising a nitroimidazole and one or more agents suitable for the prevention and/or treatment of an infectious disease in a mammal.

The present disclosure also relates to a composition comprising a synergistically effective amount of a nitroimidazole and one or more agents suitable for the prevention and/or treatment of an infectious disease in a mammal.

Preferably, the one or more agents suitable for the prevention and/or treatment of an infectious disease in a mammal is one or more antimicrobial compounds.

Preferably, the one or more additional antimicrobial compounds is selected from the group consisting of: a berberine alkaloid, arecoline, baicalin, baicalein, anemonin, matrine, oxymatrine, andrographolide, and piceid.

When combined in the same composition/formulation it would be appreciated that the nitroimidazole and the one or more agents suitable for the prevention and/or treatment of infectious disease are stable and compatible with each other and the other components of the formulation and may be formulated for administration. When formulated separately they may be provided in any convenient formulation, conveniently in such a manner as are known for such compounds in the art. It should be understood that the formulations may include other agents as disclosed herein and agents conventional in the art having regard to the type of formulation in question.

It will be understood that the scope of combinations of the nitroimidazole compounds of this disclosure with other agents includes in principle any combination of a nitroimidazole with any agent or composition suitable for the prevention and/or treatment of an infectious disease. Agents or medications for treating infectious disease are described, for example, in Goodman and Gilman's as noted above.

Metronidazole

Metronidazole is considered to be the protypical 5-nitroimidazole antibiotic. It is produced through chemical synthesis and is isolated a cream coloured solid/crystals. It is soluble in water and ethanol. It is considered effective and safe, but resistance to it is developing. The molecular structure for metronidazole is shown in FIG. 7. With reference to The Merck Index 2006, entry 6157 at page 6159, metronidazole is also named 2-methyl-5-nitroimidazole-1-ethanol. The molecular formula is $C_6H_9N_3O_3$ and molecular weight is 171.15.

It will be understood that the scope of combinations of the nitroimidazole compounds of this disclosure with other agents includes any combination of metronidazole with any agent or composition suitable for the prevention and/or treatment of an infectious disease. Agents or medications for preventing and/or treating infectious disease are described in e.g. Goodman and Gilman's as noted above. Examples of such agents include antimicrobial agents. Representative antimicrobial agents are described below. It will be understood that the invention encompasses isomeric forms, racemates, amorphous or crystalline forms, acceptable salts, solvates, prodrugs and combinations of these agents.

Berberine

Berberine is an isoquinoline alkaloid extracted from *Rhizoma coptidis, Phellodendri chinensis* cortex, and other herbs. According to the Chinese Pharmacopoeia, the berberine content of *Rhizoma coptidis, Phellodendri chinensis* and *Phellodendron amurense* and *Berberidis radix* are 5.5%, 3.0%, 0.6% and 0.6% respectively. *Rhizoma coptidis* (Huanglian in Chinese) belongs to family Ranunculaceae and contains three main *Coptis* species: *Coptis chinensis* (Weilian in Chinese), *Coptis deltoidea* (Yalian in Chinese), and *Coptis teeta* (Yunlian in Chinese). *Rhizoma coptidis* is harvested in autumn and sliced after the removing the fibrous roots. Those with bright yellow sections and very bitter taste are considered of good quality. The bitter taste of berberine (and other berberine alkaloids as disclosed herein) makes taste-masking/palatability an important issue to consider when formulating berberine alkaloids for administration to animal subjects.

Figure 2:
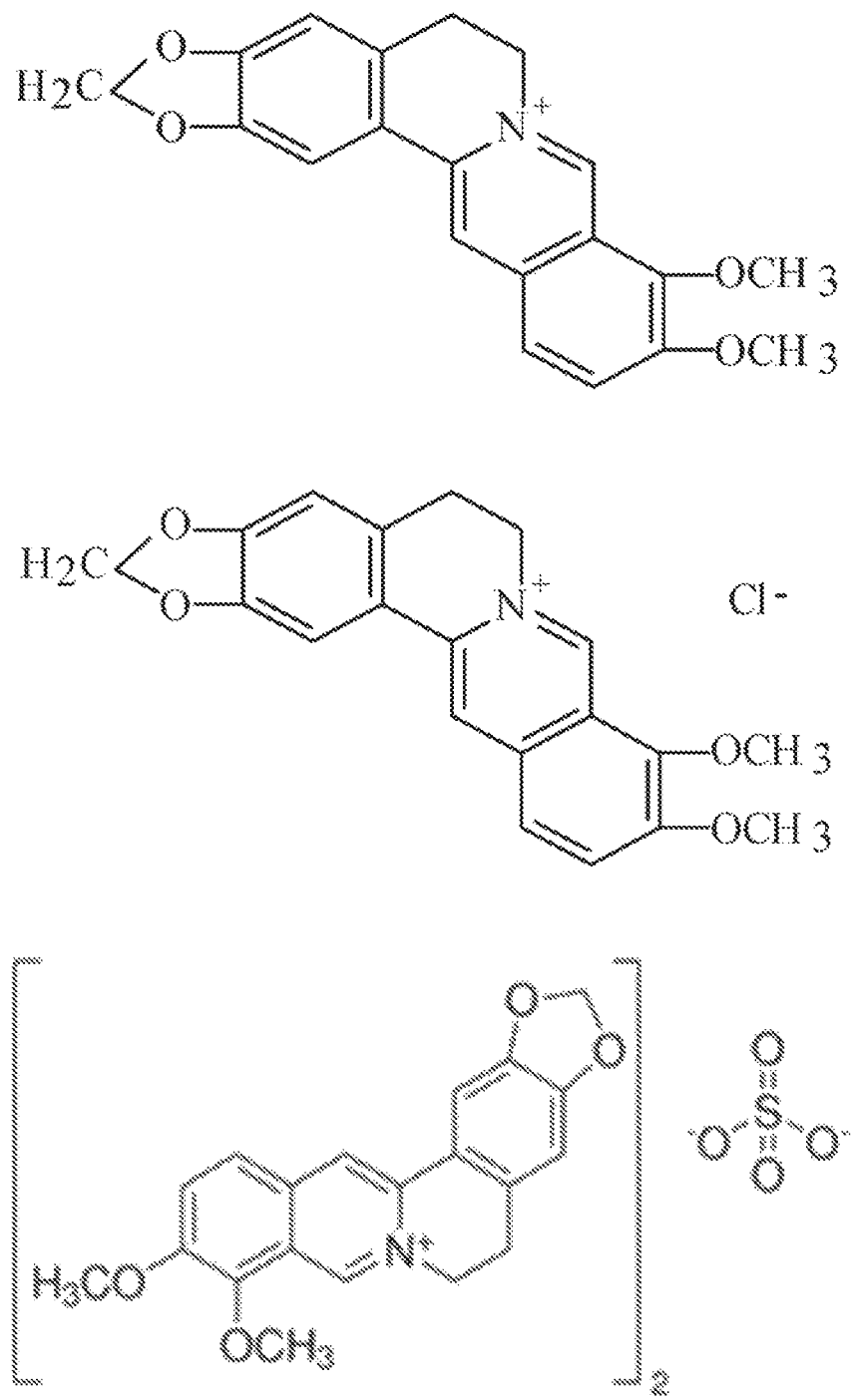
FIG. 2 depicts the molecular structure of berberine quaternary ammonium cation, berberine chloride and berberine hemisulfate.

Berberine is a yellow powder. The chloride salt is slightly soluble in cold water, but freely soluble in boiling water. It is practically insoluble in cold ethanol. The hemisulfate salt is soluble in about 30 parts water, slightly soluble in ethanol. Berberine is a quaternary ammonium cation with molecular formula of $C_{20}H_{18}NO_4^+$ and molecular weight of 336.36. FIG. 2 depicts the molecular structure of the berberine ammonium cation, berberine chloride salt, and berberine hemisulfate salt.

Berberine may be administered in any form acceptable for enteral administration. Suitable non-limiting forms for enteral administration include tablets, capsules, paste, granules, chewable wafers, gel, oral liquid, injectable liquid, medicated water and medicated feed, and suppositories. However with food-producing animals, where economic interests are important, the preferred method of administering berberine is via a feed additive in the form of granules, or a medicated feed. It may also be administered via the drinking water of an animal subject by mixing water with a suitable solution or suspension of berberine.

The present disclosure also contemplates the provision of granules and liquid formulations that can be added to food and water which make the formulations disclosed herein more palatable to, for example, food-producing animal subjects. For example, a palatable berberine alkaloid formulation may comprise berberine and an acceptable excipient which is suitable for forming a granular product. The acceptable excipient which is suitable for forming a granular product is, for example, cornstarch or polyvinylpyrrolidone (PVP). In one example, the liquid formulation is a liquid concentrate.

There are compounds which share similar structures and characteristics to berberine including, for example, the protoberberines berberrubine, coreximine, tetrahydropalmatine, jatrorrhizine, 13-hydroxyberberine chloride, coralyne chloride, 7,8-dihydro-13-methylberberine, fibrauretin (palmatine), and 13-benzylberberine. These protoberberines, together with berberine, are suitable for the compositions/feeds/feed additives/dosing regimens/methods/uses of the disclosure and are referred to herein as "berberine alkaloids".

Fibrauretin (Palmatine)

Fibrauretin or palmatine is a bitter tasting alkaloid extracted from *Fibauera recisa Pierre*. According to the Chinese Pharmacopoeia, *Fibrauera recisa Pierre* consists of no less than 2.0% fibrauretin. Another source is *Coptidis rhizoma*, the rhizome of *Coptis chinensis Franch, Coptis deltoidea* and *Coptis teeta Wall. Coptidiz rhizoma* consists of no less than 1.5% fibrauretin.

Palmatine chloride is a yellow solid, which is soluble in hot water, sparingly soluble in water, and slightly soluble in ethanol. Its melting point is 196-198° C. Its molecular formula is $C_{21}H_{22}NO_4Cl$ with a molecular weight of 387.86. The molecular structure of the palmatine quaternary ammonium cation and the structure of the chloride salt are set out in FIG. 3.

Arecoline

Arecoline is a major alkaloid constituent extracted from the traditional Chinese medicine Semen arecae, semen of *Areca catechu L*. According to Chinese Pharmacopoeia the content of Arecoline in *S Semen arecae* is not less than 0.2%. Semen arecae is manufactured primarily in Hainan province China, however *Areca catechu L*. is produced in southern Yunnan, Fujian, Guangxi, and southern Taiwan and other areas.

Figure 3:
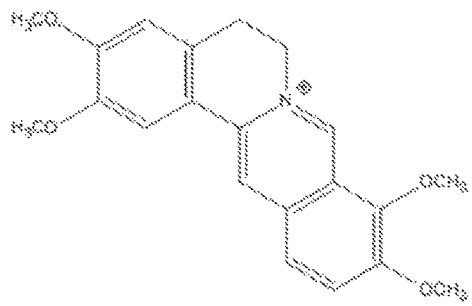
FIG. 3 depicts the molecular structures of fibrauretin (palmatine) and palmatine chloride and the molecular structures of other representative compounds of the disclosure with names.
Figure 3:
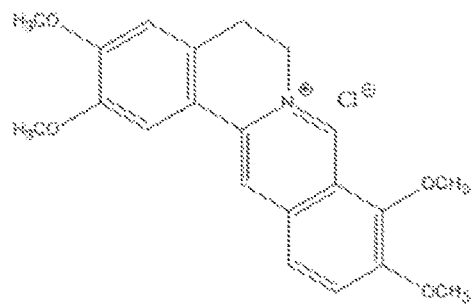
Figure 3:
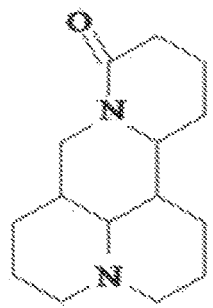
Figure 3:
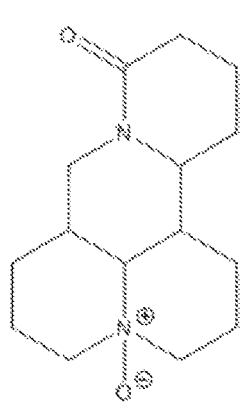
Figure 3:
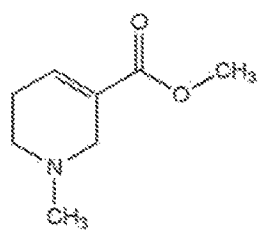
Figure 3:
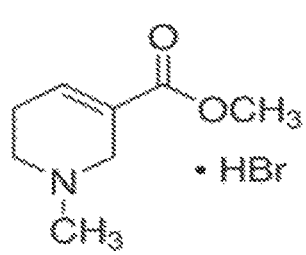
Figure 3:
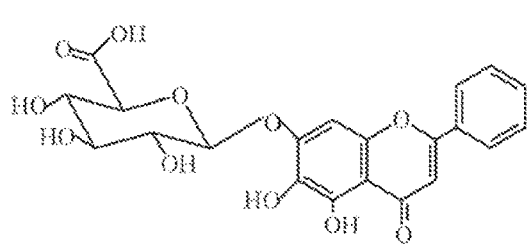
Figure 3:
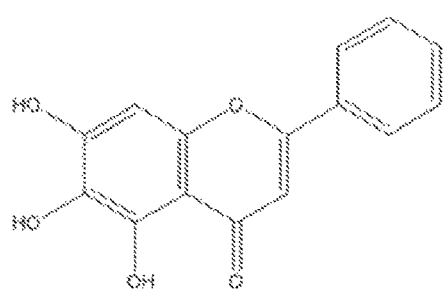

Arecoline is an odourless oily, colourless liquid with a boiling point of 209° C. It produces a solution when mixed with water and ethanol. Its molecular formula is $C_8H_{13}NO_2$, molecular weight is 155.19. Its hydrobromide salt ($C_8H_{14}BrNO_2$, MW=236.11) has a melting point of 170-175° C. and is diffluent in both water and ethanol. The molecular structures of arecoline and arecoline hydrobromide are shown in FIG. 3.

Baicalin and Baicalein

Baicalin is a major flavonoid constituent found in the traditional Chinese medicine, *Scutellaria* Root, the root of *Scutellaria baicalensis Georgi*. According to Chinese Pharmacopoeia the content of Baicalin found in *Scutellaria* Root is 9.0%. *Scutellaria* Root is manufactured mainly in Northeast China; Hebei, Shanxi, Henan, Shanxi, Neimeng province et al., although *Scutellaria* Root can be grown in most provinces of northern China.

Baicalin is a pale yellow powder, and is bitter in taste. It is diffluent in N,N-dimethylformamide, and soluble in alkaline solution, such as sodium bicarbonate, sodium carbonate, sodium hydroxide (however baicalin is unstable in alkaline environment). It is almost insoluble in water. Its molecular formula is $C_{21}H_{18}O_{11}$, molecular weight is 446.36. The molecular structure of baicalin and its aglycone, baicalein, are shown in FIG. 3.

Anemonin

Amemonin is the dry root of the Ranunculaceae plant *Clematis chinensis osbeck, Clematis* ssp *Hexapetala Pall* and *Clematis manshurica rupr*. The dry root and rhizome is called Clematidis radix et *rhizome* and according to the Chinese Pharmacopoeia contains 4.6% B1 *Pulsatilla* glycosides. Clematidis radix et *rhizoma* is produced in Jiangsu, Zhejiang, Jiangxi, Anhui and other provinces, with *Clematis hexapetala* production mainly in the northeast and Shandong while *Manshurica Rupr* lotus production is primarily in the northeast. Other sources include the dry root of *Ranunculus japnicus thunb, R Sceleratus L, Anemone hupehensis lem* and *Pulsatilla chinesis*.

Figure 4:
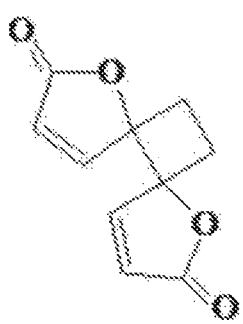
FIG. 4 depicts the molecular structures of other representative compounds of the disclosure with names.
Figure 4:
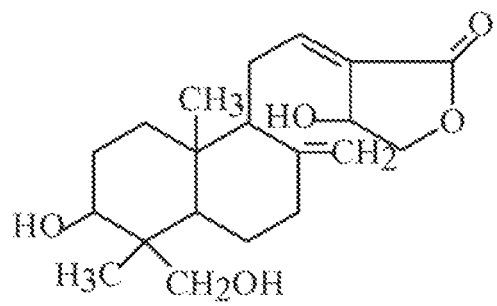
Figure 5:
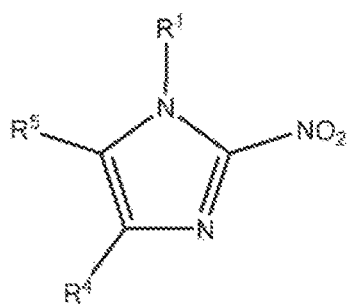
FIG. 5 depicts a general formula for 2-nitroimidazoles and representative examples. Reference molecular structures and compound names are shown.
Figure 5:
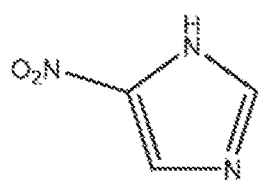
Figure 5:
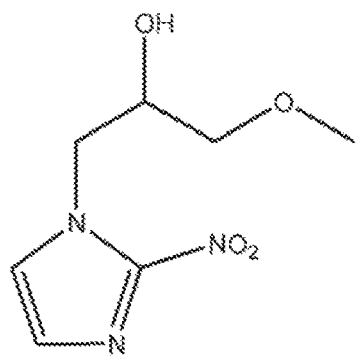
Figure 5:
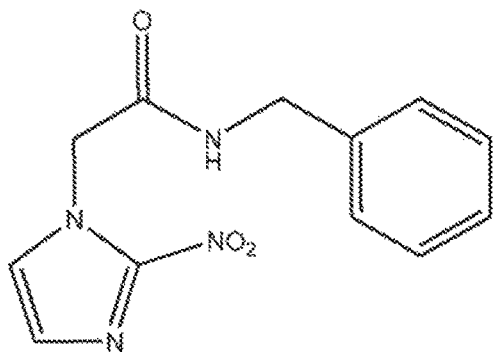

Anemonin is a white powder of bitter taste. Its melting point is around 158° C. and it is slightly soluble in cold water, soluble in hot water, and soluble in hot ethanol. Its molecular formula is $C_{10}H_8O_4$ with a molecular weight of 192.16. The molecular structure of anemonin is depicted in FIG. 4.

Matrine and Oxymatrine

Matrine and its N-oxide derivative, oxymatrine, are alkaloids extracted from the legumes (Fabaceae) and the dry root and fruit of the plant *Sophora* (*Sophora flavescens* var. *Flavescens*). According to the Chinese pharmacopoeia 2010, no less than 1.2% of Matrine is extracted from *Sophora*.

Matrine is a white odourless powder of bitter taste. The molecular formula is C15H25N2), with a molecular weight of 249.Similarly, oxymatrine is a white powder of bitter taste. The molecular formula is $C_{15}H_{24}N_2O_2$, with a molecular weight of 264. The molecular structures of matrine and oxymatrine are set out in FIG. 3.

Andrographolide

Andrographolide is a labdane diterpenoid that is produced by the *Andrographis paniculata* plant. According to the Chinese Pharmacopoeia, *Andrographis paniculata* consists of no less than 0.8% of the active substance.

Andrographolide is a colourless, powder with a crystalline appearance and is bitter in taste. It is soluble in boiling ethanol, poorly soluble in ethanol at ambient temperature, and almost insoluble in water. It has a melting point of 224-230° C. and decomposes upon melting. Its molecular formula is $C_{20}H_{30}O_5$, and has a molecular weight of 350.44. The molecular structure for andrographolide is shown in FIG. 4.

The disclosure contemplates a composition comprising two antimicrobial compounds i.e. a dual compound composition. Thus, the disclosure also relates to a composition comprising a nitroimidazole and a berberine alkaloid.

An example of a dual compound composition for treating an infectious disease in a pig is prepared by mixing a berberine alkaloid and a nitroimidazole together in varying amounts. This composition may be further mixed with a commercial feed to give of prepared feed. Following this procedure 1 kg of prepared feed for example may be obtained.

It will be appreciated that the total effective amount or dose of active agents and the ratio of the individual agents in a composition depends on the purpose of the prevention and/or treatment or other factors including the animal subject (e.g. human versus pig), route of administration, body weight and severity of the disease. Accordingly, the total effective amount of active agents and the ratio of the individual agents may be increased or decreased to suit the above purpose or factors.

An example of a dual compound composition for treating an infectious disease in a pig may comprise:

a high amount of a berberine alkaloid and a low amount of a nitroimidazole; or a high amount of berberine alkaloid and a medium amount of a nitroimidazole.

Another example of a dual compound composition for treating an infectious disease in a pig may comprise:

a medium amount of berberine alkaloid and a low amount of a nitroimidazole;

a medium amount of berberine alkaloid and a medium amount of a nitroimidazole; or a medium amount of berberine alkaloid and a high amount of a nitroimidazole.

Another example of a dual compound composition for treating an infectious disease in a pig may comprise:

a low amount of berberine alkaloid and a low amount of a nitroimidazole;

a low amount of berberine alkaloid and a medium amount of a nitroimidazole; or a low amount of berberine alkaloid and a high amount of a nitroimidazole.

The dose of a dual compound combination comprising a berberine alkaloid and a nitroimidazole in the feed may vary from a low dose to a medium dose to a high dose.

In one example, a low dose comprises a berberine alkaloid (about 0.03 g, about 0.003%) and a nitroimidazole (about 0.0015 g, about 0.00015%) in 1 kg of a prepared composition/feed where the total dose of actives is about 0.0315 g (about 0.00315%). In this example, the berberine alkaloid and nitroimidazole are in a berberine alkaloid:nitroimidazole ratio of about 0.03 g:0.0015 g i.e. about 20:1. Conversely, the nitroimidazole:berberine alkaloid ratio is about 1:20.

In one example, a medium dose comprises a berberine alkaloid (about 0.3 g, about 0.003%) and a nitroimidazole (about 0.015 g, about 0.0015%) in 1 kg of a prepared composition/feed where the total dose of actives is about 0.315 g (about 0.0315%). In this example, the berberine alkaloid and nitroimidazole are in a berberine alkaloid:nitroimidazole ratio of about 0.3 g:0.015 g i.e. about 20:1. Conversely, the nitroimidazole:berberine alkaloid ratio is about 1:20.

In one example, a high dose comprises a berberine alkaloid (about 1 g, about 0.1%) and a nitroimidazole (about 0.045 g, about 0.0045%) in 1 kg of a prepared composition/feed where the total dose of actives is about 1.045 g (about 0.1045%). In this example, the berberine alkaloid and nitroimidazole are in a berberine alkaloid:nitroimidazole ratio of about 1 g:0.045 g i.e. about 22:1. Conversely, the nitroimidazole:berberine alkaloid ratio is about 1:22.

In another example, a low dose comprises a berberine alkaloid (about 0.05 g, about 0.005%) and a nitroimidazole (about 0.003 g, about 0.0003%) in 1 kg of a prepared composition/feed where the total dose of actives is about 0.053 g (about 0.0053%). In this example, the berberine alkaloid and nitroimidazole are in a berberine alkaloid:nitroimidazole ratio of about 0.05 g:0.003 g i.e. about 17:1. Conversely, the nitroimidazole:berberine alkaloid ratio is about 1:17.

In another example, a medium dose comprises a berberine alkaloid (about 0.5 g, about 0.005%) and a nitroimidazole (about 0.03 g, about 0.003%) in 1 kg of a prepared composition/feed where the total dose of actives is about 0.53 g (about 0.053%). In this example, the berberine alkaloid and nitroimidazole are in a berberine alkaloid:nitroimidazole ratio of about 0.5 g:0.03 g i.e. about 17:1. Conversely, the nitroimidazole:berberine alkaloid ratio is about 1:17.

In another example, a high dose comprises berberine alkaloid (1.5 g, 0.15%) and a nitroimidazole (0.9 g, 0.09%) in 1 kg of a prepared composition/feed where the total dose is 2.4 g (0.24%). In this example, the berberine alkaloid and nitroimidazole are in a berberine alkaloid:nitroimidazole ratio of about 1.5 g:0.9 g i.e. about 2:1 by weight. Conversely, the nitroimidazole:berberine alkaloid ratio is about 1:2 by weight.

Preferably, the nitroimidazole and the berberine alkaloid are in a ratio of between about 1:25 and 25:1 by weight. Preferably, the nitroimidazole and the berberine alkaloid are in a ratio of between about 1:10 and about 10:1 by weight. The ratio of nitroimidazole:berberine alkaloid is preferably about: 1:10; 1:9; 1:8; 1:7; 1:6; 1:5; 1:4; 1:3; 1:2; 1:1; 1:2; 1:3; 1:4; 1:5; 1:6; 1:7; 1:8; 1:9 and 1:10. Preferably, the ratio of nitroimidazole:berberine alkaloid is about 1:1. The ratio of nitroimidazole:berberine alkaloid is preferably about 1:2.

The present disclosure also contemplates a composition as described herein when used to prevent and/or treat an infectious disease in a mammal. Preferably, the infectious disease is caused by bacteria from the genus *Clostridium*. The infectious disease is preferably caused by an antibiotic-resistant bacterial strain from the genus *Clostridium*. Preferably, the bacteria is *C. difficile*.

Preferably, the nitroimidazole is a 2-nitroimidazole. The 2-nitroimidazole is preferably a 2-nitroimidazole of Formula (Ia) as described herein. Preferably, the 2-nitroimidazole is selected from the group consisting of: azomycin, misonidazole, benzindazole, an acceptable salt thereof and a prodrug thereof. The 2-nitroimidazole is preferably selected from the group consisting of: azomycin, misonidazole and benzindazole.

Preferably, the nitroimidazole is a 4-nitroimidazole. The 4-nitroimidazole is preferably a 4-nitroimidazole of Formula (Ib) as described herein. Preferably, the 4-nitroimidazole is selected from the group consisting of: azathioprine, CGI-17341, isometronidazole, PA-824, an acceptable salt thereof and a prodrug thereof. The 4-nitroimidazole is preferably selected from the group consisting of: azathioprine, CGI-17341, isometronidazole and PA-824.

Preferably, the nitroimidazole is a 5-nitroimidazole. The 5-nitroimidazole is preferably a 5-nitroimidazole of Formula (Ic) as described herein. Preferably, the 5-nitroimidazole is selected from the group consisting of: metronidazole; azanidazole; bamnidazole; carnidazole; dimetridazole; fexinidazole; impronidazole; "MCA" nitroimidazole; megazol; "MF" nitroimidazole; nimorazole; ornidazole; panidazole; ronidazole; secnidazole; sulphimidazole; ternidazole, tinidazole, an acceptable salt thereof and a prodrug thereof.

Preferably, the 5-nitroimidazole is metronidazole. The 5-nitroimidazole is preferably selected from the group consisting of: metronidazole; azanidazole; bamnidazole; carnidazole; dimetridazole; fexinidazole; impronidazole; "MCA" nitroimidazole; megazol; "MF" nitroimidazole; nimorazole; ornidazole; panidazole; ronidazole; secnidazole; sulphimidazole; ternidazole, and tinidazole.

Preferably, the 5-nitroimidazole is metronidazole.

Preferably, the berberine alkaloid is selected from berberine chloride, berberine iodide or berberine sulfate. The berberine alkaloid is preferably berberine sulfate.

Preferably, the compositions described herein further comprise one or more acceptable excipients. The one or more acceptable excipients are preferably one or more vehicles or one or more acceptable additives. Preferably, the one or more additives are selected from the group consisting of: buffers, solubilisers, gelling agents, viscosity enhancers, preservatives, oils, antioxidants, emulsifiers, foam forming agents, isotonic agents, a propellant gas, thickeners and combinations thereof. The composition preferably further comprises excipients that may mask the off-taste of antimicrobial agents to improve palatability. For example, metronidazole is known to have a metallic taste. In this regard, the composition preferably further comprises an additive that masks the bitter flavour of the berberine alkaloid.

The compositions of the disclosure may also contain other ingredients. The compositions may also contain as non-limiting examples the components as listed hereafter. A binder such as gum, acacia, corn starch or gelatin; excipients such as dicalcium phosphate which may be used as a diluting agent; a disintegrating agent such as corn starch, potato starch, alginic acid and the like; a lubricant such as magnesium stearate; a sweetening agent such as sucrose, lactose or saccharin; and a liquid carrier, may be added. Various other ingredients may be present as coatings or to otherwise modify the physical form of the veterinary composition. The veterinary compositions may contain methyl and propylparabens as preservatives, a dye and flavouring agents such as cherry or orange flavour. Information on additives and excipients that are suitable for pharmaceutical applications may be found in, Remington: The Science and Practice of Pharmacy, 2005 or the Handbook of Pharmaceutical Excipients, 2009. Information on additives and excipients that are suitable for for veterinary applications may be found, for example, in the Merck Veterinary Manual (online at www-.merckvetmanual.com) or the CRC Handbook of Food, Drug and Cosmetic Excipients, 2005. Preferably, ingredients are government approved (e.g. FDA-approved) or GRAS substances.

Compositions of the present disclosure may be formulated for administration by any appropriate route depending on the animal subject. For example by the oral (including buccal or sublingual), rectal, nasal, topical (including buccal, sublingual or transdermal), vaginal or parenteral (including subcutaneous, intramuscular, intravenous or intradermal) route. Therefore, the compositions of the invention may be formulated as solids: for example, as tablets, capsules, powders, granules, lozenges, creams; or as liquid preparations, such as oral or sterile parenteral solutions or suspensions, emulsions (including microemulsions), syrups, elixirs or capsules filled with such liquid preparations or as gels. Formulations may be prepared as enterically coated granules, tablets or capsules suitable for oral administration and delayed release formulations. Formulations may be prepared by any method known in the art of pharmacy, for example by bringing into association an active ingredient, or combination of active ingredients, of with acceptable excipient(s).

Compositions are proposed for administration in animal feed or in the drinking water of an animal. Thus, administration of a composition may occur via the feed of an animal. The feed may be in the form of a mash, granule, crumble or pellet. In one example, administration occurs via granules for mixing through animal feeds. Administration of a composition may occur via the drinking water of an animal. In one example, the composition is dissolved in the drinking water for administration. In one example, the composition may be added as suspension to the drinking water for administration.

When a nitroimidazole compound of the disclosure is used in combination with a second active agent against the same disease, disorder or condition the dose of the compound may differ from that when the compound is used alone; the dose of the second active agent may differ from that when the second active agent is used alone; or the dose of the compound may differ from that when the compound is used alone and the dose of the second active agent may differ from that when the second active agent is used alone. In one example, when a compound of the disclosure is used in combination with a second active agent against the same disease, disorder or condition the dose of the compound is lower than that when the compound is used alone. In one example, the dose of the second active agent agent is lower than that when the second active agent is used alone. In one example, the dose of the compound is lower than that when the compound is used alone and the dose of the second active agent is lower than that when the second active agent is used alone.

The disclosure also relates to a composition comprising a synergistically effective amount of a nitroimidazole and a berberine alkaloid.

Animal Feeds and Animal Feed Additives

The present disclosure also relates to an animal feed comprising a nitroimidazole, wherein the animal feed is for consumption by a mammal. Preferably the animal feed further comprises an animal foodstuff suitable for consumption by a mammal. The mammal is preferably a pig.

The present disclosure also relates to an animal feed additive comprising a nitroimidazole, wherein the animal feed additive is for consumption by a mammal. The present disclosure also relates to a mammal formulated feed additive comprising a nitroimidazole.

It would be understood that preparation of feeds or feed additives can be accomplished using conventional procedures. Guidance on feed formulation is provided by, for example, the Food and Agriculture Organization of the United Nations at (www.fao.org). It would be recognised that formulation of feeds is dependent on the animal subject. For example, animal feed for a monogastric mammal, such as a pig, typically comprises concentrates as well as additives e.g. supplements whereas animal feed for a ruminant mammal, such as cattele, generally comprises forage (including roughage and silage) and may further comprise concentrates as well as supplements.

It will be appreciated that the exact effective amount of a nitroimidazole in the feed or feed additive depends on the purpose of the prevention and/or treatment or on other factors including the animal subject (e.g. human versus pig), route of administration, body weight and severity of the disease. Accordingly, the amounts of the nitroimidazole in the prepared feed or feed additive may be increased or decreased to suit the above purpose or factors. In combined feeds or feed additives comprising more than one active agent it will be appreciated that the total effective amount of active agents and the ratio of the individual agents may be varied to suit the above purpose or factors.

Animal feeds and animal feed additives may include various ingredients e.g. vitamins, minerals (e.g. calcium, phosphorus, trace elements such as zinc, selenium and chromium, sodium), enzymes (e.g. phytases to improve nutrient digestibility), essential oils, direct fed microbial (to maintain gastrointestinal microbiota balance and health), organic acids, amino acids (e.g, methionine, lysine and threonine) which can act as supplements and can be provided in a premix.

Other ingredients include auxiliary components and excipients as described above for the compositions of the disclosure including: binders, anti-oxidants, preservatives, coloring agents, pigments and dyes, flavouring agents, such as sweeteners, which may be used to mask the bitterness of feed ingredients to improve feed palatability, vehicles, diluting agents, emulsifying and suspending agents, attractants, and medications including growth enhancers, immunostimulants, hormones and antimicrobials. In addition, excipients are chosen for their suitability in preparing feed forms such as mash, granules, crumbles, pellets, powders and lickblocks. For example, cornstarch or polyvinylpyrollidone (PVP) are suitable for forming a granular feed product. Guidance on animal feeds, animal feed additives and excipients is also provided by the Food and Agriculture Organization of the United Nations at (www.fao.org) and other resources, for example, the Merck Veterinary Manual (on-line at www.merckvetmanual.com) and the CRC Handbook of Food, Drug and Cosmetic Excipients, 2005

The effective amount or dose of the nitroimidazole in a prepared feed may range from about 0.001 g/kg to about 2 g/kg (i.e. from about 0.0001% w/w to about 0.2% w/w).

Example effective amounts or doses of the nitroimidazole in the prepared feed are: about 0.001 g/kg (about 0.0001% w/w), about 0.003 g/kg (about 0.0003% w/w), about 0.01 g/kg (about 0.001% w/w), about 0.03 g/kg (about 0.003% w/w), about 0.1 g/kg (about 0.01% w/w), about 0.3 g/kg (about 0.03% w/w), about 1.0 g/kg (about 0.1% w/w) or about 2 g/kg (about 0.2% w/w).

Preferably, the nitroimidazole is a 2-nitroimidazole. The 2-nitroimidazole is preferably a 2-nitroimidazole of Formula (Ia) as described herein. Preferably, the 2-nitroimidazole is selected from the group consisting of: azomycin, misonidazole, benzindazole, an acceptable salt thereof and a prodrug thereof. The 2-nitroimidazole is preferably selected from the group consisting of: azomycin, misonidazole and benzindazole.

Preferably, the nitroimidazole is a 4-nitroimidazole. The 4-nitroimidazole is preferably a 4-nitroimidazole of Formula (Ib) as described herein. Preferably, the 4-nitroimidazole is selected from the group consisting of: azathioprine, CGI-17341, isometronidazole, PA-824, an acceptable salt thereof and a prodrug thereof. The 4-nitroimidazole is preferably selected from the group consisting of: azathioprine, CGI-17341, isometronidazole and PA-824.

Preferably, the nitroimidazole is a 5-nitroimidazole. The 5-nitroimdazole is preferably a 5-nitroimidazole of Formula (Ic) as described herein. Preferably, the 5-nitroimidazole is selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole, tinidazole, an acceptable salt thereof and a prodrug thereof. The 5-nitroimidazole is preferably selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole and tinidazole.

Preferably, the 5-nitroimidazole is metronidazole.

The present disclosure also relates to an animal feed comprising a composition as described herein, wherein the animal feed is for consumption by a mammal. The present disclosure also relates to an animal feed comprising a synergistic composition as described herein, wherein the animal feed is for consumption by a mammal. Preferably, the animal feeds further comprise an animal foodstuff suitable for consumption by a mammal.

The present disclosure also relates to an animal feed additive comprising a composition as described herein, wherein the animal feed is for consumption by a mammal. The present disclosure also relates to an animal feed additive comprising a synergistic composition as described herein, wherein the animal feed is for consumption by a mammal.

The present disclosure also relates to a mammal formulated feed additive comprising a composition as described herein. The present disclosure also relates to a mammal formulated feed additive comprising a synergistic composition as described herein.

The amount of the composition in the feed may range from about 0.01 g/kg to about 10 g/kg (i.e., about 0.001% to about 1% w/w); about 0.003% to about 1% w/w; about 0.01% to about 1% w/w; about 0.03% to about 1% w/w; about 0.1% to about 1% w/w; about 0.3% to about 1% w/w. Example amounts of the composition may be: about 0.01 g/kg (about 0.001%); about 0.03 g/kg (about 0.003%); about 0.1 g/kg (about 0.01%); about 0.3 g/kg (about 0.03%); about 1 g/kg (about 0.1%); about 3 g/kg (about 0.3%); about 10 g/kg (about 1%). Further example amounts of the composition in the foodstuff may be: about 0.031 g/kg (about 0.0031%); about 0.06 g/kg (about 0.006%); about 0.11 g/kg (about 0.011%); about 0.1503 g/kg (about 0.015%).

The feed is preferably in the form of a mash; granule; crumble; pellet; or in an aqueous form. Preferably, the feed is in the form of a mash. The feed is preferably in the form of a crumble. Preferably, the feed is in the form of a pellet. The feed is preferably in an aqueous form.

Dosing Regimens

The present disclosure also relates to a dosing regimen comprising administering a nitroimidazole for 1 to 6 weeks and in an amount effective to prevent and/or treat an infectious disease in a mammal.

Preferably, the nitroimidazole is a 2-nitroimidazole. The 2-nitroimidazole is preferably a 2-nitroimidazole of Formula (Ia) as described herein. Preferably, the 2-nitroimidazole is selected from the group consisting of: azomycin, misonidazole, benzindazole, an acceptable salt thereof and a prodrug thereof. The 2-nitroimidazole is preferably selected from the group consisting of: azomycin, misonidazole and benzindazole.

Preferably, the nitroimidazole is a 4-nitroimidazole. The 4-nitroimidazole is preferably a 4-nitroimidazole of Formula (Ib) as described herein. Preferably, the 4-nitroimidazole is selected from the group consisting of: azathioprine, CGI-17341, isometronidazole, PA-824, an acceptable salt thereof and a prodrug thereof. The 4-nitroimidazole is preferably selected from the group consisting of: azathioprine, CGI-17341, isometronidazole and PA-824.

Preferably, the nitroimidazole is a 5-nitroimidazole. The 5-nitroimdazole is preferably a 5-nitroimidazole of Formula (Ic) as described herein. Preferably, the 5-nitroimidazole is selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole, tinidazole, an acceptable salt thereof and a prodrug thereof. The 5-nitroimidazole is preferably selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole and tinidazole.

Preferably, the 5-nitroimidazole is metronidazole.

Preferably, the dosing regimen further comprises co-administering one or more agents suitable for the prevention and/or treatment of an infectious disease. The one or more agents is preferably one or more antimicrobial compounds. Preferably, the one or more antimicrobial compounds is a berberine alkaloid. The dosing regimen preferably further comprises administration of an additive that masks a bitter flavour of the berberine alkaloid. Preferably, the infectious disease is caused by bacteria from the genus *Clostridium*.

The present disclosure also relates to a dosing regimen comprising administering a composition as described herein for 1 to 6 weeks and in an amount effective to prevent and/or treat an infectious disease in a mammal.

The present disclosure also relates to a dosing regimen comprising administering a synergistic composition as described herein for 1 to 6 weeks and in an amount effective to prevent and/or treat an infectious disease in a mammal.

The present disclosure also relates to a dosing regimen comprising administering:
  an animal feed comprising a nitroimidazole as described herein; or
  an animal feed comprising a composition as described herein; or
  an animal feed comprising a synergistic composition as described herein;
for 1 to 6 weeks and in an amount effective to prevent and/or treat an infectious disease in a mammal.

The present disclosure also relates to a dosing regimen comprising administering a composition for 1 to 6 weeks and in an amount effective to prevent and/or treat an infectious disease in a mammal, wherein the infectious disease is caused by bacteria from the genus *Clostridium*.

The present disclosure also relates to a dosing regimen comprising administering a synergistic composition for 1 to 6 weeks and in an amount effective to prevent and/or treat an infectious disease in a mammal, wherein the infectious disease is caused by bacteria from the genus *Clostridium*.

The present disclosure also relates to a dosing regimen comprising administering:
  an animal feed comprising a nitroimidazole as described herein; or
  an animal feed comprising a composition as described herein; or
  an animal feed comprising a synergistic composition as described herein;
for 1 to 6 weeks and in an amount effective to prevent and/or treat an infectious disease in a mammal, wherein the infectious disease is caused by bacteria from the genus *Clostridium*.

Preferably, in the dosing regimens disclosed herein the nitroimidazole or the composition or animal feed is administered for 1, 2, 3, 4, 5 or 6 weeks. Preferably, the nitroimidazole, or the composition or animal feed is administered for 1 to 6; 2 to 5; or between 3 to 4 weeks.

Methods for Administering Compositions, Animal Feeds and Animal Feed Additives

The disclosure also relates to a method for preventing and/or treating an infectious disease in a mammal comprising administering a composition as described herein.

The disclosure also relates to a method for preventing and/or treating an infectious disease in an animal comprising administering a synergistic composition as described herein.

The disclosure also relates to a method for preventing and/or treating an infectious disease in an animal comprising administering:
  an animal feed comprising a nitroimidazole as described herein; or
  an animal feed comprising a composition as described herein; or
  an animal feed comprising a synergistic composition as described herein.

The disclosure also relates to a method for preventing or treating an infectious disease caused by bacteria from the genus *Clostridium* in a mammal, the method comprising administering a composition as described herein.

The disclosure also relates to a method for preventing or treating an infectious disease caused by bacteria from the genus *Clostridium* in a mammal, the method comprising administering a synergistic composition as described herein.

The disclosure also relates to a method for preventing or treating an infectious disease caused by bacteria from the genus *Clostridium* in a mammal, the method comprising administering:
- an animal feed comprising a nitroimidazole as described herein; or
- an animal feed comprising a composition as described herein; or
- an animal feed comprising a synergistic composition as described herein.

In the disclosed dosing regimens and methods for preventing and/or treating an infectious disease caused by bacteria from the genus *Clostridium* through administering the compositions or animal feeds described herein the infectious disease is preferably an infectious intestinal disease. Preferably, the infectious disease is caused by an antibiotic-resistant bacterial strain from the genus *Clostridium*. The bacteria are preferably *C. difficile*. The infectious disease is preferably diarrhoea and the animal is human. Preferably, the infectious disease is colitis and the animal is human.

Methods for Reduction of Feed Conversion Ratio

The disclosure also relates to a method for the reduction of feed conversion ratio in a food-producing animal, wherein the method comprises the step of administering a nitroimidazole to the food-producing animal, wherein the food-producing animal is a mammal.

The disclosure also relates to a method for the reduction of feed conversion ratio in a food-producing animal, wherein the method comprises the step of administering a composition as described herein to the food-producing animal, wherein the food-producing animal is a mammal.

The disclosure also relates to a method for the reduction of feed conversion ratio in a food-producing animal, wherein the method comprises the step of administering a synergistic composition as described herein to the food-producing animal, wherein the food-producing animal is a mammal.

The disclosure also relates to a method for the reduction of feed conversion ratio in a food-producing animal, wherein the method comprises the step of administering:
- an animal feed comprising a nitroimidazole as described herein; or
- an animal feed comprising a composition as described herein; or
- an animal feed comprising a synergistic composition as described herein, to the food-producing animal, wherein the food-producing animal is a mammal.

Preferably, the food-producing animal is free of disease. The food-producing animal is preferably diseased. Preferably, the food-producing animal is a pig.

Methods for Improving or Maintaining Gastrointestinal Health

The disclosure also relates to a method for improving or maintaining gastrointestinal health in a mammal, wherein the method comprises the step of administering a nitroimidazole to the mammal.

The disclosure also relates to a method for improving or maintaining gastrointestinal health in a mammal, wherein the method comprises the step of administering a composition as described herein to the mammal.

The disclosure also relates to a method for improving or maintaining gastrointestinal health in a mammal, wherein the method comprises the step of administering a synergistic composition as described herein to the mammal.

The disclosure also relates to a method for improving or maintaining gastrointestinal health in a mammal, wherein the method comprises the step of administering:
- an animal feed comprising a nitroimidazole as described herein;
- an animal feed comprising a composition as described herein;
- an animal feed comprising a synergistic composition as described herein, to the mammal.

In any one of the above methods for improving or maintaining gastrointestinal health in a mammal the mammal is preferably a human or a pig. Preferably, the mammal is a human. The mammal is preferably a pig.

In any one of the above methods for the reduction of feed conversion ratio or in any one of the above methods for improving or maintaining gastrointestinal health the nitroimidazole is preferably a 2-nitroimidazole. The 2-nitroimidazole is preferably a 2-nitroimidazole of Formula (Ia) as described herein. Preferably, the 2-nitroimidazole is selected from the group consisting of: azomycin, misonidazole, benzindazole, an acceptable salt thereof and a prodrug thereof. The 2-nitroimidazole is preferably selected from the group consisting of: azomycin, misonidazole and benzindazole.

Preferably, the nitroimidazole is a 4-nitroimidazole. The 4-nitroimidazole is preferably a 4-nitroimidazole of Formula (Ib) as described herein. Preferably, the 4-nitroimidazole is selected from the group consisting of: azathioprine, CGI-17341, isometronidazole, PA-824, an acceptable salt thereof and a prodrug thereof. The 4-nitroimidazole is preferably selected from the group consisting of: azathioprine, CGI-17341, isometronidazole and PA-824.

Preferably, the nitroimidazole is a 5-nitroimidazole. The 5-nitroimdazole is preferably a 5-nitroimidazole of Formula (Ic) as described herein. Preferably, the 5-nitroimidazole is selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole, tinidazole, an acceptable salt thereof and a prodrug thereof. The 5-nitroimidazole is preferably selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole and tinidazole.

Preferably, the 5-nitroimidazole is metronidazole.

Uses

The present disclosure also relates to use of a nitroimidazole in the preparation of: a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole and one or more agents suitable for the prevention and/or treatment of an infectious disease in a mammal in the preparation of a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole and a berberine alkaloid in the preparation of a medicament; an animal feed, wherein the animal feed is for consumption by a mammal; an animal feed additive, wherein the animal feed is for consumption by a mammal; or a mammal formulated feed additive.

The present disclosure also relates to use of a nitroimidazole in the preparation of a medicament for
  (i) the prevention and/or treatment of an infectious disease in a mammal, wherein the infectious disease is caused by bacteria from the genus *Clostridium;*
  or
  (ii) improving or maintaining gastrointestinal health in a mammal;
  or
  (iii) the reduction of feed conversion ratio in a food-producing animal, wherein the food-producing animal is a mammal.

The present disclosure also relates to use of a nitroimidazole in the preparation of an animal feed; animal feed additive; or a mammal formulated feed additive for:
  (i) improving or maintaining gastrointestinal health in a mammal; or
  (ii) the reduction of feed conversion ratio in a food-producing animal, wherein the food-producing animal is a mammal.

The present disclosure also relates to use of a nitroimidazole and one or more agents suitable for the prevention and/or treatment of an infectious disease in a mammal in the preparation of a medicament for:
  (i) the prevention and/or treatment of an infectious disease in a mammal, wherein the infectious disease is caused by bacteria from the genus *Clostridium;*
  or
  (ii) improving or maintaining gastrointestinal health in a mammal;
  or
  (iii) the reduction of feed conversion ratio in a food-producing animal, wherein the food-producing animal is a mammal.

The present disclosure also relates to use of a nitroimidazole and one or more antimicrobial compounds in the preparation of an animal feed; animal feed additive; or a mammal formulated feed additive for:
  (i) improving or maintaining gastrointestinal health in a mammal; or
  (ii) the reduction of feed conversion ratio in a food-producing animal, wherein the food-producing animal is a mammal.

The present disclosure also relates to use of a nitroimidazole and a berberine alkaloid in the preparation of a medicament for:
  (i) the control, prevention and/or treatment of an infectious disease in a mammal, wherein the infectious disease is caused by bacteria from the genus *Clostridium;*
  or
  (ii) improving or maintaining gastrointestinal health in a mammal;
  or
  (iii) the reduction of feed conversion ratio in a food-producing animal, wherein the food-producing animal is a mammal.

The present disclosure also relates to use of a nitroimidazole and a berberine alkaloid in the preparation of an animal feed; animal feed additive; or a mammal formulated feed additive for:
  (i) improving or maintaining gastrointestinal health in a mammal; or
  (ii) the reduction of feed conversion ratio in a food-producing animal, wherein the food-producing animal is a mammal.

The present disclosure also relates to use of a nitroimidazole in:
  (i) the prevention and/or treatment of an infectious disease in a mammal, wherein the infectious disease is caused by bacteria from the genus *Clostridium;*
  or
  (ii) improving or maintaining gastrointestinal health in an animal;
  or
  (iii) the reduction of feed conversion ratio in a food-producing animal, wherein the food-producing animal is a mammal.

The present disclosure also relates to use of a nitroimidazole and one or more agents suitable for the prevention and/or treatment of an infectious disease in a mammal in:
  (i) the prevention and/or treatment of an infectious disease in a mammal, wherein the infectious disease is caused by bacteria from the genus *Clostridium;*
  or
  (ii) improving or maintaining gastrointestinal health in an animal;
  or
  (iii) the reduction of feed conversion ratio in a food-producing animal.

The present disclosure also relates to use of a nitroimidazole and one or more antimicrobial compounds in:
  (i) the prevention and/or treatment of an infectious disease in a mammal, wherein the infectious disease is caused by bacteria from the genus *Clostridium;*
  or
  (ii) improving or maintaining gastrointestinal health in an animal;
  or
  (iii) the reduction of feed conversion ratio in a food-producing animal.

The present disclosure also relates to use of a nitroimidazole and a berberine alkaloid in:
  (i) the prevention and/or treatment of an infectious disease in a mammal, wherein the infectious disease is caused by bacteria from the genus *Clostridium;*
  or
  (ii) improving or maintaining gastrointestinal health in a mammal;
  or
  (iii) the reduction of feed conversion ratio in a food-producing animal, wherein the food-producing animal is a mammal.

The present disclosure also relates to use of a nitroimidazole in the preparation of a medicament for the prevention and/or treatment of an infectious disease in a mammal. Preferably, the infectious disease is an infectious intestinal disease.

The present disclosure also relates to use of a nitroimidazole and one or more agents suitable for the prevention and/or treatment of an infectious disease in an animal in the preparation of a medicament for the prevention and/or treatment of an infectious disease in a mammal. Preferably, the infectious disease is an infectious intestinal disease. The one or more agents is preferably one or more antimicrobial compounds. The one or more additional antimicrobial compounds is preferably a berberine alkaloid. Preferably, the use further comprises administration of an additive that masks a bitter flavour of the berberine alkaloid.

The present disclosure also relates to use of a nitroimidazole and a berberine alkaloid in the preparation of a medicament for the prevention and/or treatment of an infectious disease in a mammal. Preferably, the infectious disease is an infectious intestinal disease.

The present disclosure also relates to use of a nitroimidazole in the prevention and/or treatment of an infectious disease in a mammal. Preferably, the infectious disease is an infectious intestinal disease. Preferably, the use further comprises co-administering one or more agents suitable for the prevention and/or treatment of an infectious disease in a mammal. The one or more agents is preferably one or more antimicrobial compounds. The one or more additional antimicrobial compounds is preferably a berberine alkaloid. Preferably, the use further comprises administration of an additive that masks a bitter flavour of the berberine alkaloid.

The present disclosure also relates to use of a nitroimidazole and one or more agents suitable for the prevention and/or treatment of an infectious disease in a mammal in the prevention and/or treatment of an infectious disease in a mammal. Preferably, the infectious disease is an infectious intestinal disease. The one or more agents is preferably one or more antimicrobial compounds. The one or more additional antimicrobial compounds is preferably a berberine alkaloid. Preferably, the use further comprises administration of an additive that masks a bitter flavour of the berberine alkaloid.

The present disclosure also relates to use of a nitroimidazole and a berberine alkaloid in the prevention and/or treatment of an infectious disease in a mammal. Preferably, the infectious disease is an infectious intestinal disease. Preferably, the use further comprises co-administering one or more agents suitable for the prevention and/or treatment of an infectious disease in a mammal. The one or more agents is preferably one or more antimicrobial compounds. The one or more additional antimicrobial compounds is preferably a berberine alkaloid. Preferably, the use further comprises administration of an additive that masks a bitter flavour of the berberine alkaloid.

Preferably, the nitroimidazole and the berberine alkaloid are in a ratio of between about 1:10 and about 10:1. The ratio of nitroimidazole:berberine alkaloid is preferably about: 1:10; 1:9; 1:8; 1:7; 1:6; 1:5; 1:4; 1:3; 1:2; 1:1; 2:1; 3:1; 4:1; 5:1; 6:1; 7:1; 8:1; 9:1 and 10:1. Preferably, the ratio of nitroimidazole:berberine alkaloid is about 1:1. The ratio of nitroimidazole:berberine alkaloid is preferably about 1:2. Preferably, there is a synergistic effect between the nitroimidazole and the berberine alkaloid.

In any one of the above uses, the nitroimidazole is preferably a 2-nitroimidazole. The 2-nitroimidazole is preferably a 2-nitroimidazole of Formula (Ia) as described herein. Preferably, the 2-nitroimidazole is selected from the group consisting of: azomycin, misonidazole, benzindazole, an acceptable salt thereof and a prodrug thereof. The 2-nitroimidazole is preferably selected from the group consisting of: azomycin, misonidazole and benzindazole.

Preferably, the nitroimidazole is a 4-nitroimidazole. The 4-nitroimidazole is preferably a 4-nitroimidazole of Formula (Ib) as described herein. Preferably, the 4-nitroimidazole is selected from the group consisting of: azathioprine, CGI-17341, isometronidazole, PA-824, an acceptable salt thereof and a prodrug thereof. The 4-nitroimidazole is preferably selected from the group consisting of: azathioprine, CGI-17341, isometronidazole and PA-824.

Preferably, the nitroimidazole is a 5-nitroimidazole. The 5-nitroimdazole is preferably a 5-nitroimidazole of Formula (Ic) as described herein. Preferably, the 5-nitroimidazole is selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole, tinidazole, an acceptable salt thereof and a prodrug thereof. The 5-nitroimidazole is preferably selected from the group consisting of: metronidazole, azanidazole, bamnidazole, carnidazole, dimetridazole, fexinidazole, impronidazole, "MCA" nitroimidazole, megazol, "MF" nitroimidazole, nimorazole, ornidazole, panidazole, ronidazole, secnidazole, sulphimidazole, ternidazole and tinidazole.

Preferably, the 5-nitroimidazole is metronidazole.

Preferably, the infectious disease is caused by an antibiotic-resistant bacterial strain from the genus *Clostridium*. The bacteria are preferably *C. difficile*. Preferably, the infectious disease is diarrhoea and the animal is human. The infectious disease is preferably colitis and the animal is human.

Preferably, the berberine alkaloid is selected from berberine chloride, berberine iodide or berberine sulfate. The berberine alkaloid is preferably berberine chloride. Preferably, the berberine alkaloid is berberine iodide. The berberine alkaloid is preferably berberine sulfate.

The present disclosure also relates to a nitroimidazole for use in the prevention and/or treatment of an infectious disease in a mammal. Preferably, the infectious disease is an infectious intestinal disease. The infectious disease is preferably caused by bacteria from the genus *Clostridium*.

The present disclosure also relates to a nitroimidazole for use in improving or maintaining gastrointestinal health in a mammal.

The present disclosure also relates to a nitroimidazole for use in the reduction of feed conversion ratio in a food-producing animal, wherein the food-producing animal is a mammal.

The present disclosure also relates to a nitroimidazole and any one or more agents suitable for the prevention and/or treatment of an infectious disease in a mammal for use in the prevention and/or treatment of an infectious disease in a mammal. Preferably, the infectious disease is an infectious intestinal disease. The infectious disease is preferably caused by bacteria from the genus *Clostridium*.

The present disclosure also relates to a nitroimidazole and any one or more agents suitable for the prevention and/or treatment of an infectious disease in a mammal for use in improving or maintaining gastrointestinal health in a mammal.

The present disclosure also relates to a nitroimidazole and any one or more agents suitable for the prevention and/or treatment of an infectious disease in a mammal for use in the reduction of feed conversion ratio in a food-producing animal, wherein the food-producing animal is a mammal.

The present disclosure also relates a nitroimidazole and a berberine alkaloid for use in the prevention and/or treatment of an infectious disease in a mammal. Preferably, the infectious disease is an infectious intestinal disease. The infectious disease is preferably caused by bacteria from the genus *Clostridium*.

The present disclosure also relates to a nitroimidazole and a berberine alkaloid for use in improving or maintaining gastrointestinal health in a mammal.

The present disclosure also relates to a nitroimidazole and a berberine alkaloid for use in the reduction of feed conversion ratio in a food-producing animal, wherein the food-producing animal is a mammal.

Feed Safety and Residue Levels

Human and animal drugs and animal feed additives are highly regulated for safety reasons. In Australia, the Therapeutic Goods Administration (TGA) is responsible for regulating therapeutic goods for human use while the Australian Pesticides and Veterinary Medicines Authority (APMVA) is responsible for the assessment and registration of pesticides and veterinary medicines. In the US, the Food and Drug Administration (FDA) is responsible for the approval of human and animal drugs and feed additives which are governed by the Federal Food, Drug, and Cosmetic Act (FD&C Act).

The FD&C Act requires that compounds intended for use in food-producing animals are shown to be safe and that food produced from animals exposed to these compounds is shown to be safe for consumption. Otherwise, the compounds may be prohibited. A compound is not prohibited if it can be determined by prescribed methods of examination that there is not an unsafe residue of that compound that will be found in the food produced from food-producing animals under conditions of use reasonably certain to be followed in practice.

In particular, the use in food-producing animals of any compound found to induce cancer when ingested by people or animal is prohibited by statute (21 CFR Part 500, Subpart E—Regulation of carcinogenic compounds used in food-producing animals) unless certain conditions are met (the so-called "Diethylstilbestrol (DES) Proviso"). Under the DES proviso use of a suspected carcinogenic compound is not prohibited if it can be determined by prescribed methods of examination that "no residue" of that compound will be found in the food produced from food-producing animals under conditions of use reasonably certain to be followed in practice.

For illustration, despite the safety of berberine alkaloids as evidenced by, for example, their wide use as dietary supplements for humans for many years in frequent and high doses (berberine, for instance is sold for use once or twice daily at doses as high as 400 mg berberine chloride per capsule) they have come under the suspicion that they are carcinogenic agents even though, berberine, itself, has anti-cancer activity (Ma et al. 2017). Thus, if the FDA decides that berberine should be regulated as a carcinogenic compound, US statue prohibits the use of berberine in food-producing animals unless the "no residue" DES proviso applies.

The term "no residue" refers to any residue remaining in the edible tissues of food-producing animals that is so low that it presents an insignificant risk of cancer to consumers. More specifically, an insignificant risk of cancer is defined as a 1 in 1 million increase in risk. A "safe" residue level of an antimicrobial agent, e.g. berberine, as used herein, is one that poses an insignificant risk of disease, particularly cancer.

Despite the recorded safety of berberine, a toxicology study was commissioned by the US Government (National Centre for Toxicological Research) and this study identified potential carcinogenicity in a high-dose chronic rodent study [Toxicology and Carcinogenesis Studies of Goldenseal Root Powder (*Hydrastis canadensis*) in F344/N Rats and B6C3F1 Mice (Feed Studies). National Toxicology Program Technical Report Series 2010 (562), pp 1-188.Research Triangle Park, NC: National Toxicology Program].

As a result to obtain GRAS status it is necessary to estimate the residue of berberine in the meat of food-producing animals that would be acceptable, given the typical lifetime consumption of that meat. This is ensure that there is a lower than a one in a million risk of cancer resulting from consumption of meat from a food-producing animal. The residue level of an IVP component, e.g. a berberine alkaloid such as berberine, for assessing GRAS status may be determined by experiment relying on mass analysis of the component (as shown in, for example, WO2018/176079 the disclosure of which is herein incorporated by reference).

An example protocol for determining the residue level of a berberine alkaloid in animal tissue using LC-MS/MS is as follows:

Samples of muscle tissue, and tissue from liver and kidney are taken an animal after treatment. A known weight of tissue (approximately 1 g) was homogenized in 2 mL water. Samples were centrifuged and a known volume of the supernatant was removed for analysis of berberine by LC-MS/MS to provide the residue level of berberine in muscle, liver or kidney tissue (ng of berberine per g of tissue).

Further, a "Residue study" can be conducted to determine the residue depletion profile for a naturally occurring IVP administered at the maximum label dose rate through quantification of the marker tissue residue in animals treated via feed administration over a full production cycle. This tissue residue depletion study is to be conducted according to SOPs and good scientific practice. Accordingly, the residue study can determine tissue residues of an IVP when administered orally to mammals. The study investigates whether a combination feed compound of the disclosure i.e. a feed comprising a nitroimidazole and a berberine is safe and suitable for GRAS status.

Summary

Animals receive, for example, a nominated dose of nitroimidazole and berberine alkaloid (e.g., metronidazole and berberine chloride) added into their feed or receive regular feed without additive (i.e. control groups). Treatment is continued for a specified period when tissue collection and analysis occurs. Selected groups of animals are either fed up to tissue collection or fed beyond tissue collection on regular feed to examine residues after a specified washout period. Muscle tissue and/or tissue from an organ may be collected. The organ may be liver, kidney or skin. For example, muscle tissue, liver and/or kidney tissue is collected. Skin tissue may also be collected. IRP001 chloride is extracted from the tissue. The residual mass of IRP001 chloride is determined using a LC-MS/MS assay. The assay is fully validated during each assay run with accuracy, and limits of detection (LLOD) and quantitation (LLOQ) assessed.

Analytical Methods

Details of assay methods for tissue extraction and berberine assay by LC-MS/MS are summarized below. The assay of berberine was calibrated initially from simple solutions and subsequently methods for assay after tissue extraction were validated. Berberine was assayed by LC-MS/MS using tetrahydropalmitine as an internal standard.

Preparation of Tissue Samples

1. Approximately 1 g of tissues are sampled and weighed into M-tubes. The tissues are stored in a freezer at −20° C. until they are ready to be homogenized.
2. For each gram of tissue, 2 volumes of MilliQ water was added to the tubes.
3. The M-tubes were attached onto the GentleMACS homogenizer and the program method RNA_01_01 (60 seconds) was run 3 times to ensure that the tissue was completely homogenized.

4. The tissue homogenates were distributed into Eppendorf tubes in 200 μL aliquots.
5. To each 200 μL aliquot of tissue homogenate, 10 μL internal standard solution was added, followed by 600 μL of 100% methanol. Samples were vortexed at maximum setting for 3×10 seconds and then centrifuged at 10,000 rpm for 3 minutes.
6. 100 μL of supernatant was transferred into LC vials for analysis.

Method Validation
1. The method was validated for selectivity, linearity, LLOQ, accuracy, precision, recovery, stability and matrix effect.
2. Selectivity was assessed by preparing samples spiked with individual analyte at concentrations up to 500 ng/g with 5 replicates each. The peak signal was compared with the calibration standards (spiked with analytes) to ensure that there was no interference.
3. To evaluate LLOQ, the 5 ng/g and 10 ng/g standards were prepared at 6 replicates. The LLOQ was determined at the lowest concentration of the calibration curve which both precision and accuracy were ≤20%.
4. For an indication of accuracy and precision, 4 concentration levels of 20, 50, 100 and 500 ng/g were prepared (5 replicates each). Accuracy was denoted as bias (%) from the nominal concentration and precision was denoted as the relative standard deviation (RSD) of the replicates.
5. To evaluate recovery, matrix recovery samples were prepared by extracting blank tissue and then spiking with the analyte solutions to give various concentration levels up to 500 ng/g (5 replicates each). The recovery was defined by the ratio of the mean peak area of extracted samples to the mean peak area of matrix recovery samples.
6. To evaluate bench-top stability, 4 concentration levels of 20, 50, 100 and 500 ng/g were prepared at 5 replicates each, where they were kept at room temperature for 30 minutes prior to extraction. The mean peak area was compared to that of freshly-prepared standards.
7. To evaluate matrix effect (ME), 4 concentration levels of 20, 50, 100 and 500 ng/g in neat solution were prepared at 5 replicates each. ME was defined as the ratio of the mean peak area of recovery samples to that of the neat standard samples.

Example LC-MS assay conditions are shown in Table 3.

TABLE 3

| LC-MS Assay conditions | |
|---|---|
| Instrument | Shimadzu LC-MS 8050-2 |
| Mobile phase | A: 0.1% formic acid in MilliQ water B: 0.1% formic acid in methanol |
| Column | Phenomenex Kinetex 2.6 μm xB-C18 100 Angstrom 50 × 3 mm |
| Column Temperature | 40° C. |
| Injection Volume | 1 μl |
| Run time | 4.5 min |
| Flow Rate | 0.4 mL/min |
| Needle wash solution | 90:10:1 Methanol-Water-Acetic acid |
| Elution mode | Gradient |
| Gradient conditions: | |
| Time (minutes) | % B |
| 0.01 | 10 |
| 0.5 | 30 |

TABLE 3-continued

| LC-MS Assay conditions | |
|---|---|
| 3 | 70 |
| 3.2 | 95 |
| 3.8 | 95 |
| 4.0 | 10 |
| 4.5 | 10 |

The present disclosure contemplates that there is a low residue level of the berberine alkaloid in the tissue of the mammal after a treatment period. The present disclosure also contemplates that there is a safe residue level of the berberine alkaloid in the tissue of the mammal after a treatment period. The present disclosure also contemplates that there is a low residue level of the berberine alkaloid in the tissue of the mammal after a treatment period and a washout period. The present disclosure also contemplates that there is a safe residue level of the berberine alkaloid in the tissue of the mammal after a treatment period and a washout period.

As used herein, a "safe" residue level of a feed compound, for example berberine, is one that poses an insignificant risk of disease, particularly cancer.

In one example, there is a low residue level of the berberine alkaloid in the muscle tissue of the mammal after a treatment period. In another example, there is a safe residue level of the berberine alkaloid in the muscle tissue of the mammal after a treatment period.

In one example, there is a low residue level of the berberine alkaloid in the muscle tissue of the mammal after a treatment period and a washout period. In another example, there is a safe residue level of the berberine alkaloid in the muscle tissue of the mammal after a treatment period and a washout period.

In one example, there is a low residue level of the berberine alkaloid in the muscle tissue of the mammal and the tissue of an organ of the mammal after a treatment period. In another example, there is a safe residue level of the berberine alkaloid in the muscle tissue of the mammal and the tissue of an organ of the mammal after a treatment period.

In one example, there is a low residue level of the berberine alkaloid in the liver and muscle tissue of the mammal after a treatment period. In another example, there is a safe residue level of the berberine alkaloid in the liver and muscle tissue of the animal after a treatment period.

In one example, there is a low residue level of the berberine alkaloid in the muscle tissue of the mammal and the tissue of an organ of the mammal after a treatment period and a washout period. In another example, there is a safe residue level of the berberine alkaloid in muscle tissue of the animal and the tissue of the organ after a treatment period and a washout period.

In one example, there is a low residue level of the berberine alkaloid in the liver and muscle tissue of the mammal after a treatment period and a washout period. In another example, there is a safe residue level of the berberine alkaloid in the liver and muscle tissue of the animal after a treatment period and a washout period.

In one example, there is a low residue level of the berberine alkaloid in the tissue of an organ of the mammal after a treatment period. In another example, there is a safe residue level of the berberine alkaloid in the tissue of an organ of the mammal after a treatment period. In another example, there is a low residue level of the berberine alkaloid in the tissue of an organ of the mammal after a treatment period and a washout period. In another example, there is a safe residue level of the berberine alkaloid in the tissue of an organ of the mammal after the treatment period and a washout period.

In another example, there is a low residue level of the berberine alkaloid in the liver tissue of the mammal after a treatment period. In another example, there is a safe residue level of the berberine alkaloid in the liver tissue of the mammal after a treatment period. In another example, there is a low residue level of the berberine alkaloid in the liver tissue of the mammal after a treatment period and a washout period. In another example, there is a safe residue level of the berberine alkaloid in the liver tissue of the mammal after the treatment period and a washout period.

Safety of IVPs may be determined by monitoring mammal subjects for any adverse reactions or adverse effects such as behavioural changes e.g. morbidity or unanticipated events. Safety of IVPs may also be determined through histology studies on organ tissue such as gastrointestinal tissue (such as duodenum, jejenum, ileum, colon or any combination thereof), liver tissue, kidney tissue or skin tissue or any combination thereof. Histology studies may include the analysis of lesions in tissue which may comprise the semi-quantitative scoring of lesions to give, for example, a lesion index or a cumulative pathology index. Safety of IVPs may also be determined by hematology studies, investigation of blood and/or serum chemistry.

Development of formulations, dosages and regimens for preventing or treating infectious disease in an animal can be undertaken with respect to the studies below which determine *Clostridium* toxins and spore formation based on example published protocols (ELISA for toxins: Kyne et al. 2001 which refers to Kyne et al. 2000 and Warny et al. 1994; spore formation: Merrigan et al. 2010 which refers to Sambol et al. 2002).

*Clostrium* Toxin Protocols

ELISA Measurement of Serial Serum IgA, IgG, and IgM Concentrations Against *C. difficile* Toxin A, Toxin B, or Non-Toxin Antigens According to the example protocols of Kyne et al. 2000, stool specimens and rectal swabs are cultured for 72 hours under anaerobic conditions in selective (cycloserine, cefoxitin, fructose) broth medium.

Presumptive identification of *C. difficile* is made by subculturing of specimens on solid medium, examination of colony morphology, Gram's staining, and the use of a system of rapid identification based on enzymatic activity (Rapid-Ana, Innovative Diagnostics, Atlanta).

Cytotoxin activity is assessed in filter-sterilized fecal supernatants using the tissue-culture cytotoxin assay. To confirm that a cytotoxin effect is caused by *C. difficile* toxins, the fecal filtrate is mixed with neutralizing antibodies against *C. difficile* toxins according to the manufacturer's instructions (Techlab, Blacksburg, Va.). An aliquot of the fecal filtrate is supplemented with protease inhibitors (complete protease inhibitors, Boehringer Mann-hein, Mannheim, Germany) and used for antibody testing.

Toxin A and Toxin B are purified from the supernatant of a culture of strain VPI 10463 (American Type Culture Collection 43255). Non-toxin antigens are prepared from a sonicate of two non-toxigenic strains of *C. difficile* (American Type Culture Collection 43597 and 43593).

Levels of antibody against *C. difficile* toxin A, toxin B, and the nontoxin antigen preparation are measured by an enzyme-linked immunosorbent assay (ELISA) using a commercially available kit.

ELISA Measurement of IgA, IgG, and Anitoxin A

According to the example protocol of Warny et al. 1994, one volume of stool sample is diluted with 2 volumes of phosphate-buffered saline (PBS) at 4° C. The suspension is vigorously vortexed, and the volume of the stool homogenate is measured to calculate the original stool volume. After centrifugation at 1,000×g for 20 min at 4° C., the supernatant is supplemented with 2 mM phenylmethylsulfonyl fluoride, a protease inhibitor, and centrifuged at 12,000×g for 15 min. The IgA concentration is determined in the supernatant by ELISA.

IgA Concentration as Determined by ELISA

Microtiter plates (Maxisorb; Nunc, Roskilde, Denmark) are coated overnight at 4° C. with rabbit immunoglobulins to human alpha-chains (Dako, Glostrup, Denmark) at 1/1,000 in PBS. The plates are saturated with PBS with 0.05% (vol/vol) Tween 20 (PBST) and 1% bovine serum albumin (PBST-BSA). Two-fold dilutions of stool homogenate in 1% PBST-BSA are incubated for 1 h at room temperature. To detect bound IgA, horseradish peroxidase-labeled rabbit anti-human IgA (Dako) is diluted 1/1,000 in PBST-BSA, and this mixture is incubated for 1 h at room temperature. The plates are washed three times with PBST between incubation steps. The diammonium salt of 2,2'-azino-bis (3-ethyl-benzthiazoline sulfonate-6) (Sigma) in citrate-phosphate buffer is used as the substrate. After incubation for 30 min at room temperature, the optical density at 415 nm (OD415) is measured with a microplate reader (Bio-Rad). Serial two-fold dilutions of purified colostral sigA are used as the standard, and the results are expressed in weight per original stool volume (in micrograms per milliliter).

IgG Concentration as Determined by ELISA

Microtiter plates (Polysorb; Nunc) are coated with rabbit immunoglobulins to human gamma-chains (Dako) at 1/1,000 in PBS. Four-fold dilutions of fecal supernatant in 1% PBST-BSA are incubated for 1 h at room temperature. To detect bound IgG, horseradish peroxidase-labeled rabbit anti-human IgG (Dako) is diluted 1/1,000 in PBST-BSA. Serial two-fold dilutions of a serum control (Ortho Diagnostic System, Beerse, Belgium) is diluted in a pool of 10 normal fecal supernatants and used as the standard. The ODs are similar to those obtained with PBST-BSA as the diluent. Results are expressed in weight per original stool volume (in micrograms per milliliter).

ELISA Measurement of Antitoxin A

Microtiter plates (Polysorb; Nunc) are coated with toxin A. Serum samples are diluted 1/100 in PBST-BSA and incubated for 1 h at room temperature. Fecal supernatants are normalized at 10 µg of IgA per ml in PBST-BSA before testing and incubated overnight at 4° C. Serum and intestinal antibodies are detected with horseradish peroxidase-labeled rabbit anti-human IgA or IgG (Dako) diluted 1/1,000 in PBST-BSA. Horseradish peroxidase-labeled rabbit anti-human secretory component (Dako) are used for assaying for fecal secretory antitoxin at a 1/200 dilution in PBST-BSA. Control sera positive for specific IgG and IgA and stool samples positive for IgA, sIgA, and IgG are obtained from patients with CDAD. Overnight incubation of all controls with increasing concentrations of toxin A induced a dose-dependent reduction of OD values. The mean OD observed when the sample is substituted by PBST-BSA is defined as the background level. In all assays, samples yielding an OD five times greater than the background OD are reported as positive. Specific serum antibody titers are expressed in arbitrary units (AU) by using OD values of serial dilutions of a highly positive serum control. The value of 5 AU is placed arbitrarily as the cutoff level. Fecal antibody titers of 10 μg of IgA per ml are expressed as the test $OD_{415}$ divided by the background $OD_{415}$ ($OD_t/OD_b$) and this value is multiplied by (fecal total IgA concentration×$10^{-1}$) to express specific activity per milliliter of stool. All samples are tested in triplicate and in two assays. The intra-assay coefficient of variation is less than 5% in all assays. A rise is determined as a difference greater than twice the coefficient of variation of the controls.

Spore Formation Protocols

To assess the accumulation of spores over the growth cycle, a differential spore-plating and microscopy method is used. At 8, 20, 28, and 48 h postinoculation into brain heart infusion (BHI) broth as described above, 1-mL samples of each strain are clarified by centrifugation, and the pellets are washed in PBS, heat shocked at 65° C. for 15 min (to kill vegetative cells), serially diluted, and plated on 1% taurocholate (a spore germinant) fructose agar (TFA) plates to enumerate spores (Sambol et al. 2002). The plates are incubated anaerobically for 48 h, after which CFU are enumerated, and the data are represented as total spores per milliliter of starting culture. For microscopy, 10 μL samples of 48-hour cultures are applied to microscope slides, then oven dried at 85° C. for 5 min, and then Gram stained. Spores are to be defined as all fully formed refractile bodies, whether free or attached to mother cell material. For each strain, 10 distinct fields are photographed and enumerated at ×100 magnification under oil immersion. Spores in all fields are counted, and data are represented as the mean number of spores per field and the percentage of spores obtained per total maximum vegetative cell count at the end of exponential phase (3.0 108 CFU/ml at an $OD_{600}$ of 1.03).

EXAMPLES

*Clostridium*

Infections resistant to existing antimicrobial medicines are growing at an alarming rate. For example, use of β-lactam antibiotics and fluoroquinolones can lead to secondary infection and further complications such as overgrowth of *Clostridium difficile* (CD). CD is a bacterium that can cause symptoms ranging from diarrhea to life-threatening inflammation of the colon. CD epidemiology is depicted in FIG. 2 (reproduced from Martin et al. 2016). Illness from CD most commonly affects older adults often in long-term care facilities and typically occurs after use of antibiotic medications. However, studies show increasing rates of CD infection among people traditionally not considered high risk, such as younger and healthy individuals without a history of antibiotic use or exposure to health care facilities. Each year in the United States, about a half million people get sick as a result of release of CD toxins, and in recent years, CD infections have become more frequent, severe and difficult to treat with the rise of antimicrobial resistance. Ironically, the standard treatment for CD is another antibiotic: metronidazole for mild to moderate infection; vancomycin for more severe infection.

However, up to 20 percent of people with CD get sick again. After two or more recurrences, rates of further recurrence increase up to 65 percent. Although antimicrobial therapy with metronidazole is usually effective, resistance and therefore treatment failure is growing [Miyamoto et al. 2013]. Resistance has been observed in *H. pylori*, and *T. vaginalis* and *G. duodenalis* [Upworth et al. 2006; Miyamoto et al. 2013].

Example 1

Antimicrobial Selectivity

Eleven natural compounds, metronidazole and a positive control, vancomycin, were tested against six strains of *C. difficile* as shown in Table 4.

TABLE 4

| *C. difficile* strains used for Example 1 | | |
|---|---|---|
| Strain | Ribotype | Other information |
| M7404 | 027 | Epidemic isolate, Canada 2005 |
| R20291 | 027 | Epidemic isolate, England 2006 |
| CD72 | 014 | Australian Hospital isolate, 2007 |
| CD90 | 002 | Australian Hospital isolate, 2008 |
| 630 | 012 | Historic isolate, Reference strain, Switzerland 1982 |
| VPI10463 | 087 | Historic isolate, Reference strain, high toxin producer |

The eleven natural compounds, or combinations, tested were:
1. Berberine chloride
2. Berberine sulfate
3. Arecoline
4. Anemonin
5. Matrine
6. Oxymatrine
7. Andrographolide
8. Palmatine
9. Berberine Sulfate+Andrographolide
10. Berberine Chloride+Andrographolide
11. Baicalin The natural compounds, metronidazole and vancomycin were obtained from commercial sources, e.g. Sigma-Aldrich.

Results
(1) Berberine sulfate vs. the six strains
MIC range: 256~1024 μg/mL
MBC range: 256~1024 μg/mL
(2) Berberine chloride vs. the six strains
MIC range: 256~1024 μg/mL
MBC range: 256~1024 μg/mL
(3) Palmatine vs. CD72 & CD90
MIC range: 512~1024 μg/mL
MBC range: 512~1024 μg/mL
(4) Other compounds vs. M7404
MIC>1024 μg/mL
(5) Metronidazole vs. 6 strains
MIC range: 0.25~1 μg/mL
MBC range: 0.25~2 μg/mL
(6) Vancomycin vs. 6 strains
MIC range: 0.5~2 μg/mL
MBC range: ≥1 μg/mL Checkerboard Assay for Antibiotic Combinations The three combinations below were tested vs. 6 strains of *C. difficile* following the experimental protocols and synergy calculations set out in Magi et al. 2015.
Berberine+Metronidazole
Berberine+Vancomycin
Metronidazole+Vancomycin In accordance with Magi et al. 2015, synergy is calculated using the equation below:

$$\Sigma FIC = FIC_A + FIC_B = MIC_{A\ (combine)}/MIC_{A\ (alone)} + MIC_{B\ (combine)}/MIC_{B\ (alone)}$$

When $\Sigma FIC \leq 0.5$, synergy is observed.

Results are shown as follows in Table 5 (first replicate) and Table 6 (second replicate).

TABLE 5

Replicate 1: Berberine + Metronidazole

| | 0 | 16 | 32 | 64 | 128 | 256 | 512 | Berb |
|---|---|---|---|---|---|---|---|---|
| 0 | | | | | | | ** | |
| 0.03125 | | | | | | | | |
| 0.0625 | | | | | | | | |
| 0.125 | | | | | | | | |
| 0.25 | | | | | | ** | | |
| 0.5 | | ** | ** | * | | | | |
| 1 | | | | | | | | |
| Met | | | | | | | | |

$MIC_{Berb\ (alone)} = 1024$
$MIC_{Met\ (alone)} = 1$
$MIC_{Berb\ (combine)}, MIC_{Met\ (combine)}$: 256, 0.5; 128, 0.5; 256, 0.25
$\Sigma FIC = 0.75; 0.625; 0.5$ therefore $\Sigma FIC = 0.5$.

TABLE 6

Replicate 2: Berberine + Metronidazole

| | 0 | 16 | 32 | 64 | 128 | 256 | 512 | Berb |
|---|---|---|---|---|---|---|---|---|
| 0 | | | | | | | ** | |
| 0.03125 | | | | | | | ** | |
| 0.0625 | | | | | | | ** | |
| 0.125 | | | | | | | | |
| 0.25 | | | | | | ** | | |
| 0.5 | | ** | ** | ** | * | | | |
| 1 | | * | | | | | | |
| Met | | | | | | | | |

$MIC_{Berb\ (alone)} = 512$
$MIC_{Met\ (alone)} = 2$
$MIC_{Berb\ (combine)}, MIC_{Met\ (combine)}$: 256, 0.5; 128, 0.5; 256, 0.25
$\Sigma FIC = 0.75; 0.5; 0.625$ therefore $\Sigma FIC = 0.5$.

Figure 11:
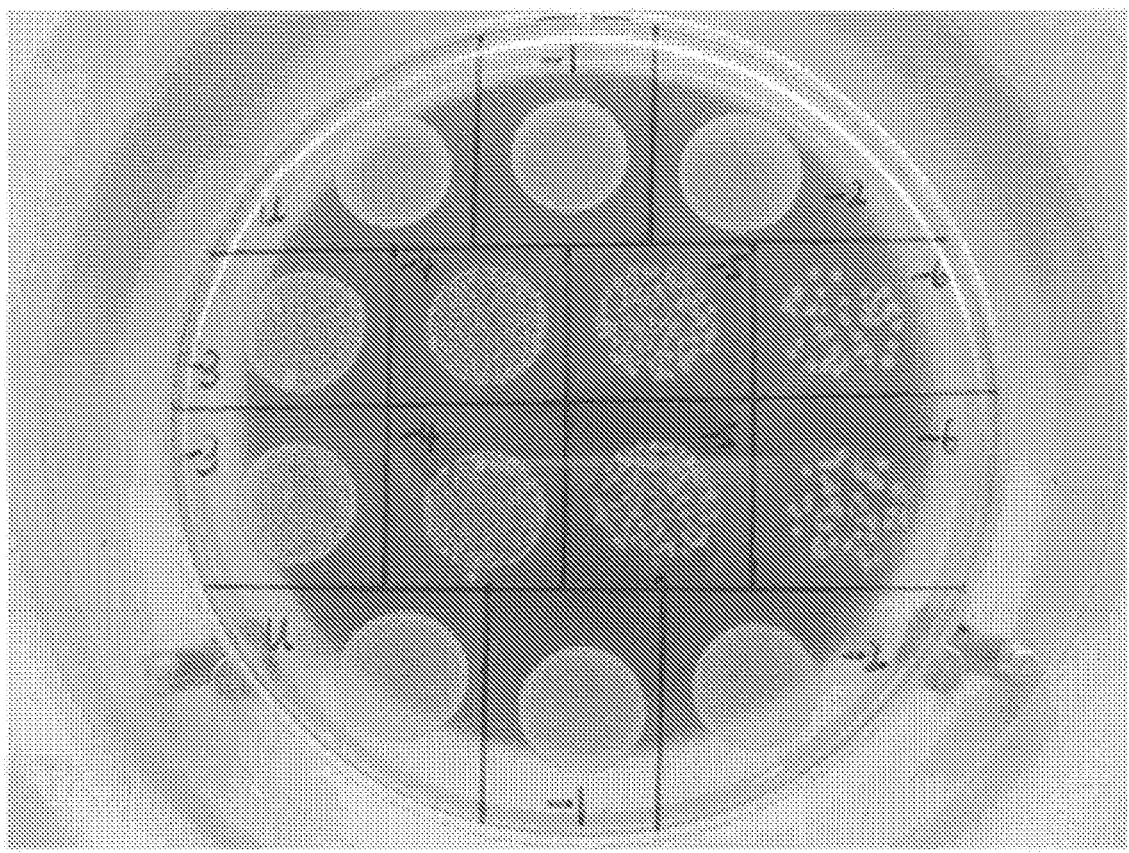
FIGS. 11 to 13 depict colony counting experiments from Example 1 study.
Figure 12:
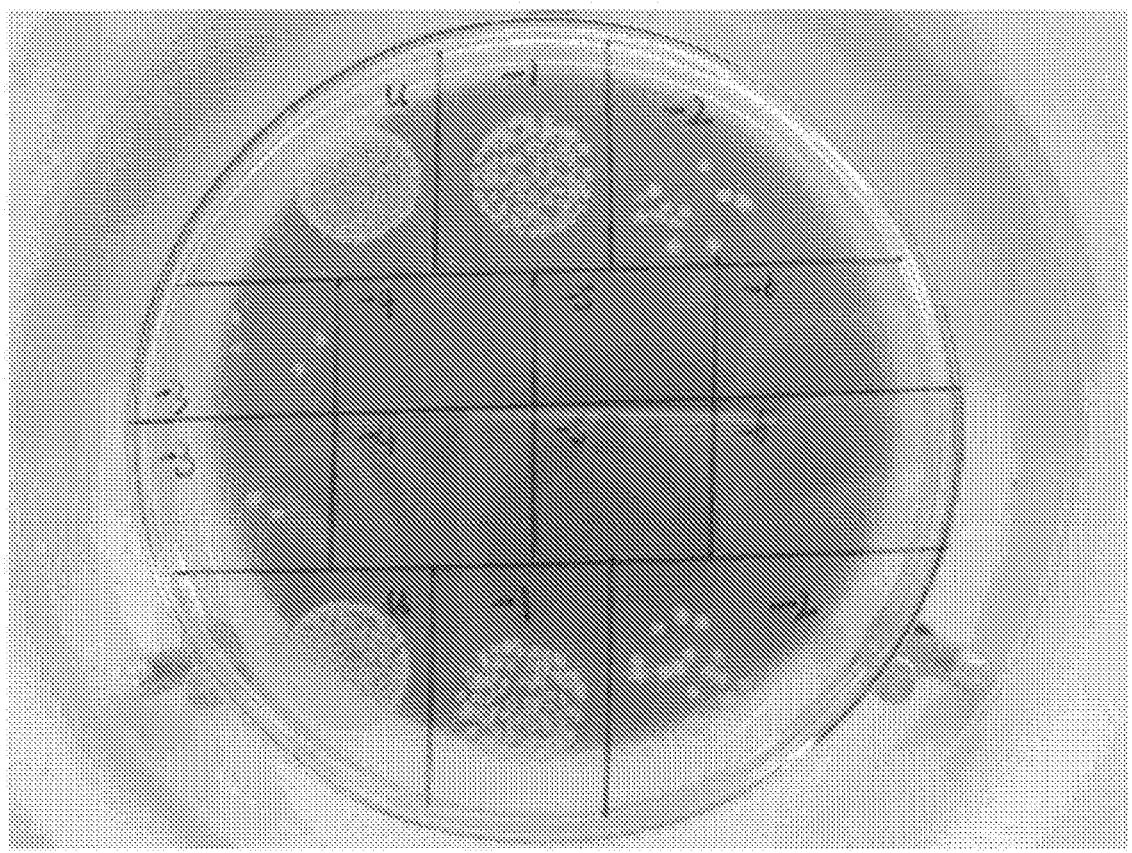
Figure 13:
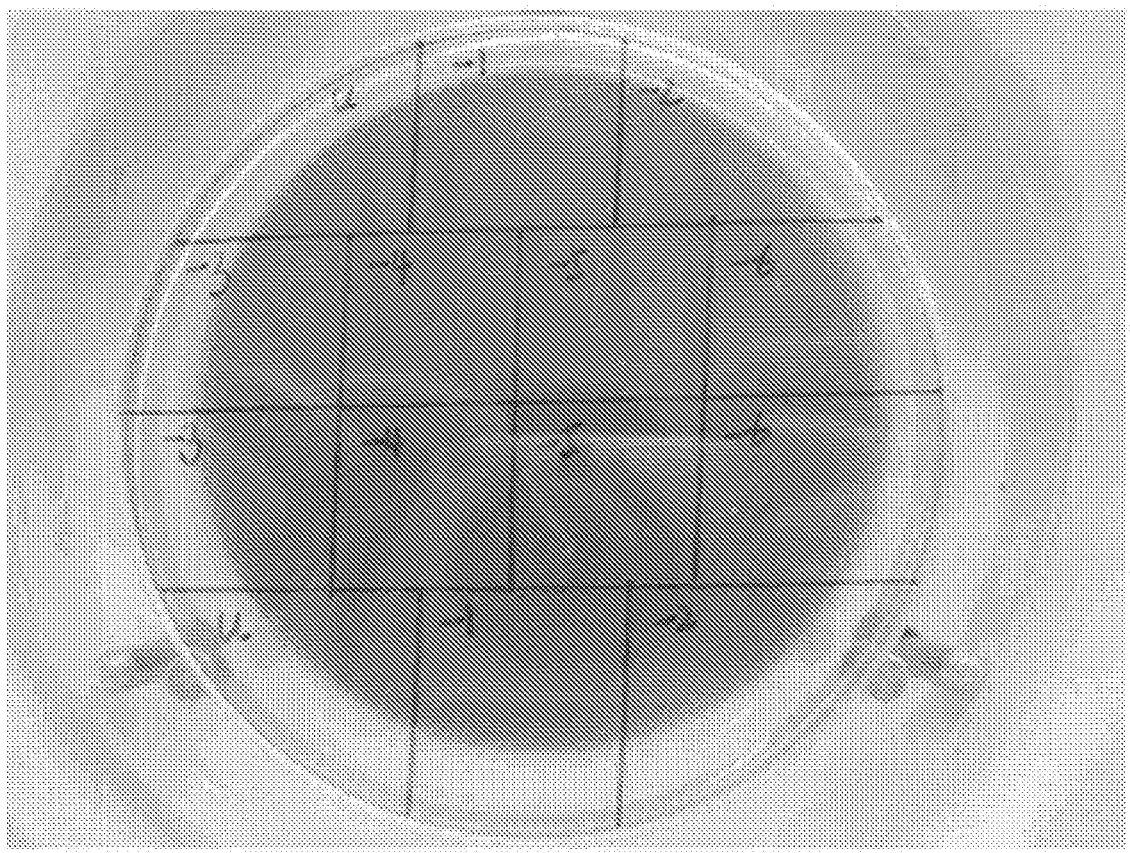

Both replicate experiments show synergy as indicated by ΣFIC value and comparison of results from cell colony experiments in FIGS. 11 to 13. In these experiments, it has been shown that administration of berberine sulfate in combination with metronidazole (128 μg/mL of berberine sulfate and 0.25 μg/mL of metronidazole together) significantly lowers the dose of metronidazole required to prevent and/or treat infectious disease caused by *Clostridium* compared to when metronidazole is used alone (i.e. metronidazole alone at a concentration of 0.25 μg/mL). This surprising lowering of dose has the potential to lower the risk of metronidazole resistance developing in *Clostridium*.

Conversely the administration of metronidazole in combination with berberine has the surprising effect of lowering the dose of berberine required to to prevent and/or treat infectious disease caused by *Clostridium* compared to when berberine is used alone (i.e. berberine sulfate alone at at concentration of 128 μg/mL). The findings point to a synergistic effect between metonidazole and berberine.

Example 2

In Vivo Mouse Trial
Study Design:
Groups of five, six week old, male, C57BL6/J mice were pre-treated with an antibiotic cocktail in the drinking water containing kanamycin (0.4 mg/ml), gentamicin (0.035 mg/ml), colistin (850 U/ml), metronidazole (0.215 mg/ml), vancomycin (0.045 mg/ml) and cefaclor (0.3 mg/ml) for 7 days, followed by three days of cefaclor alone. These antibiotics disrupt the resident microbiota and induce susceptibility to infection with *Clostridium difficile*. On the day of infection, antibiotic pre-treatment was ceased and mice were switched to plain drinking water prior to infection with a ribotype 027 *C. difficile* strain (M7404) at a dose of $10^5$ spores/mouse by oral gavage. Eight hours post-infection, mice were orally administered 100 ul of the respective treatments, followed by the immediate addition of the treatment to the drinking water. The treatments were replenished fresh daily. The mice were monitored twice daily for signs of infection and faecal samples were analysed by microbiological techniques for the presence of *C. difficile* spores. Mice were humanely killed when they reached ethical endpoints, which include 10% acute weight loss (in the first 24 hours) or 15% chronic weight loss.

Treatment groups (1 to 7):
Untreated (received plain water)
Metronidazole (Met, 50 mg/kg)
Metronidazole (Met, 25 mg/kg)
Berberine (Berb, 50 mg/kg)
Berberine (Berb, 25 mg/kg)
Metronidazole (25 mg/kg) and Berberine (50 mg/kg)
Metronidazole (25 mg/kg) and Berberine (25 mg/kg)
Results are shown in Table 7.

TABLE 7

Results of in vivo mouse trial

| Grp. | Trt | D0 | D1 | D1½ | D1¾ | D2 | D3 | D4 |
|---|---|---|---|---|---|---|---|---|
| 1 | — | 100% | 50% | 0% | 0% | 0% | 0% | 0% |
| 2 | Met (50 mg/kg) | 100% | 100% | 100% | 100% | 20% | 20% | 20% |
| 3 | Met (25 mg/kg) | 100% | 60% | 20% | 20% | 0% | 0% | 0% |
| 4 | Berb (50 mg/kg) | 100% | 20% | 0% | 0% | 0% | 0% | 0% |
| 5 | Berb (25 mg/kg) | 100% | 0% | 0% | 0% | 0% | 0% | 0% |
| 6 | Berb (50 mg/kg) + Met (25 mg/kg) | 100% | 100% | 100% | 60% | 20% | 20% | 20% |
| 7 | Berb (25 mg/kg) + Met (25 mg/kg) | 100% | 100% | 100% | 100% | 0% | 0% | 0% |

Figure 14:
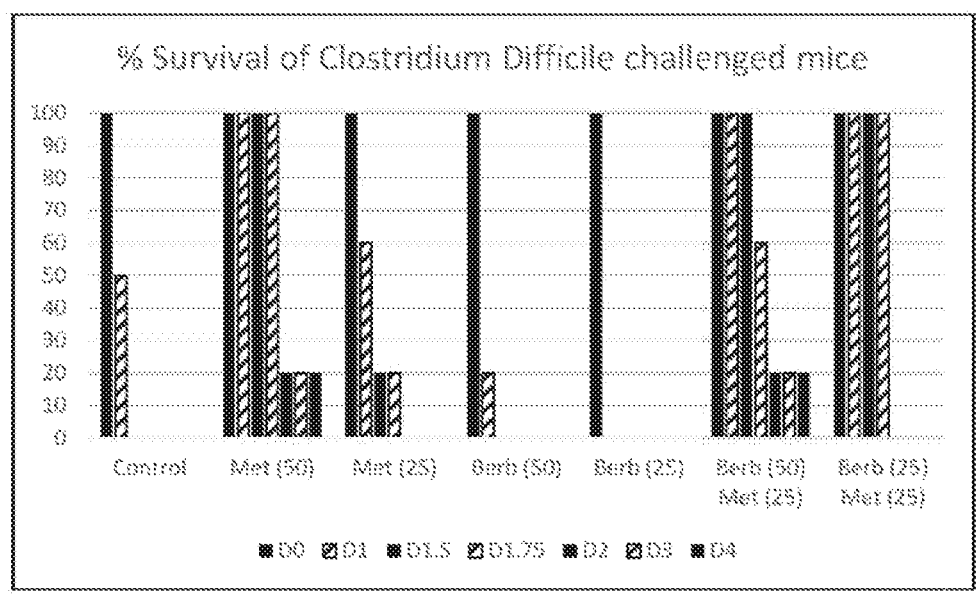
FIG. 14 is a bar graph depicting the survival results shown in Table 6.

A graph of the results shown in Table 7 is presented in FIG. 14.

Summary of results:
The doses of metronidazole administered to the mice were not high enough to result in survival of the mice, with no statistical difference in survival observed between mice that were administered either 25 mg/kg or 50 mg/kg of metronidazole compared to untreated mice.
Berberine administered at either 25 mg/kg or 50 mg/kg did not increase the survival time of mice.
Importantly, combining berberine with metronidazole significantly increased the survival time of mice and delayed disease compared to metronidazole alone. Mice that received a combination of metronidazole (25 mg/kg) and berberine (50 mg/kg) showed a significant delay in fulminant disease compared to mice receiving 25 mg/kg of metronidazole alone (p=0.0349). Similarly, mice that received a combination of metronidazole (25 mg/kg) and berberine (25 mg/kg) showed a significant delay in fulminant disease compared to mice receiving 25 mg/kg of metronidazole alone (p=0.017). Note that 1/5 mice survived to the end of the experiment (day 4) from the Metronidazole (50 mg/kg) group and the Metronidazole (25 mg/kg) and Berberine (50 mg/kg). These two mice did lose weight (so were sick), but did not reach 15% weight loss, so did not have to be humanely killed.

In summary, it has been found that administration of metronidazole in combination with berberine sulfate unexpectedly and significantly increases efficacy compared to metronidazole and berberine sulfate alone in the prevention and/or treatment of infectious disease caused by *Clostridium*.

The results surprisingly demonstrate that a nitroimidazole antibiotic has synergy in combination with a berberine alkaloid in the prevention and/or treatment of infectious disease caused by *Clostridium*.

The results indicate that doses of metronidazole and berberine could be optimised further to protect mice from *C. difficile* disease and permit overall survival.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

REFERENCES

Martin J S, Monaghan T M, Wilcox M H. "*Clostridium difficile* infection: epidemiology, diagnosis and understanding transmission" (2016) *Nat Rev Gastroenterol Hepatol.* 13(4): 206-16.

Remington: The Science and Practice of Pharmacy, 21$^{st}$ Edition, Lippincott Williams and Wilkins, 2005.

Handbook of Pharmaceutical Excipients, 6$^{th}$ Ed., R. C. Rowe, P. J. Shesky, M. E. Quinn (Editors), Pharmaceutcial Press and American Pharmacists Association, 2009.

CRC Handbook of Food Drug and Cosmetic Excipients, 1$^{st}$ Ed., 1992, S. C. Smolinkse, CRC Press.

P. L. Gould (1986) *International Journal of Pharmaceutics*, November, 33 (1-3), 201-217.

S. M. Berge et al. (1997) *Journal of Pharmaceutical Science*, January, 66 (1), 1/P. Heinrich Stahl, Camille G. Wermuth (Eds.) (2011) Handbook of Pharmaceutical Salts: Properties, Selection and Use, Second Revised Edition, Wiley.

Edwards D (1993) "Nitroimidazole drugs—action and resistance mechanisms I. Mechanism of action" *Journal of Antimicrobial Chemotherapy*, 31(1):9-20.

Kapoor V K, Chadha R, Venisetty P K, Prasanth S (2003) "Medicinal Significance of Nitroimidazoles—Some Recent Advances" Journal of Scientific & Industrial Research, 62:659-665.

Stella, V. J. et al. (1985) "Prodrugs", *Drug Delivery Systems*, pp. 112-176; Drugs, 29, pp. 455-473 and "Design of Prodrugs", ed. H. Bundgard, Elsevier.

Zhang, L. et al. (2013) "Synthesis and bioactive evaluation of novel hybrids of metronidazole and berberine as new type of antimicrobial agents and their transportation behavior by human serum albumin" *Bioorganic & Medicinal Chemistry*, 21: 4158-4169.

Fang, et al., "Synthesis and biological activities of novel amine-derived bis-azoles as potential antibacterial and antifungal agents", European Journal of Medicinal Chemistry, 2010, 45: 4388-4398.

Upcroft J A, Dunn L A, Wright J M, Benakli K, Upcroft P, Vanelle P (2006) "5-Nitroimidazole drugs effective against metronidazole-resistant Trichomonas vaginalis and Giardia duodenalis" *Antimicrob. Agents Chemother.* 2006, 50(1):344-7.

Miyamoto Y, Kalisiak J, Korthals K, Lauwaet T, Cheung D Y, Lozano R, Cobo E R, Upcroft P, Upcroft J A, Berg D E, Gillin F D, Fokin V V, Sharpless K B, Eckmann L. "Expanded therapeutic potential in activity space of next-generation 5-nitroimidazole antimicrobials with broad structural diversity" Proc. Natl. Acad. Sci. USA. 2013, 110(43):17564-9.

Mital, A. (2009) "Synthetic Nitroimidazoles: Biological Activity and Mutagenicity Relationship", *Scientia Pharmaceutica* 77: 497-520.

Kim, P. et al. (2009) "Structure-activity relationships of antitubercular nitroimidazoles. I. Structural features associated with aerobic and anaerobic activities of 4- and 5-nitroimidazoles", *J. Med. Chem.* 52(5): 1317-1328

Mathias, F. et al., (2017) "An Efficient One-Pot Catalyzed Synthesis of 2,4-Disubstituted 5-Nitroimidazoles Displaying Antiparasitic and Antibacterial Activities" *Molecules,* 22: 1278

Goodman & Gilman's (2005) "The Pharmacological Basis of Therapeutics", 11$^{th}$ Ed., L. L. Brunton (Ed.), J. S. Lazo and K. L. Parker (Assoc. Eds.), McGraw-Hill.

The Merck Index (2006) "The Merck Index: An Encyclopedia of Chemicals, Drugs, and Biologicals" (The Merck Index), M. J. O'Neil (Ed.), Fourteenth edition (Merck & Co., Inc., Whitehouse Station, NJ, USA.

Ma, W.; Zhu, M.; Zhang, D.; Yang, L.; Yang, T.; Li, X.; and Zhang, Y. "Berberine inhibits the proliferation and migration of breast cancer ZR-75-30 cells by targeting Ephrin-B2*" Phytomedicine* 2017, 25: 45-51.

Kyne, L. et al. (2001) "Association between antibody response to toxin A and protection against recurrent *Clostridium difficile* diarrhoea", *Lancet,* 2001; 357: 189-93.

Kyne, L. et al. (2000) "Asymptomatic carriage of *Clostridium difficile* and serum levels of IgG antibody against toxin A" *N. Engl. J. Med.* 342: 390-97.

Warny M, Vaerman J P, Avesani V, Delmée M. (1994) "Human antibody response to *Clostridium difficile* toxin A in relation to clinical course of infection" *Infect Immun.* 62(2):384-9

Merrigan M, et al., "Human Hypervirulent *Clostridium difficile* Strains Exhibit Increased Sporulation as Well as Robust Toxin Production", *Journal of Bacteriology,* 2010, 192(19): 4904-4911.

Sambol S P, Merrigan M M, Tang J K, Johnson S, Gerding D N. "Colonization for the prevention of *Clostridium difficile* disease in hamsters" *J. Infect. Dis.* 2002, 186 (12):1781-9.

Magi G, Marini E, Facinelli B. 2015 "Antimicrobial activity of essential oils and carvacrol, and synergy of carvacrol and erythromycin, against clinical, erythromycin-resistant Group A Streptococci" *Front Microbiol.* 6:165.

The invention claimed is:

1. A method for the prevention or treatment of an infectious disease in a mammal caused by an antibiotic-resistant bacterial strain from the genus *Clostridium*, comprising administering an effective amount of a composition comprising a 5-nitroimidazole selected from the group consisting of: metronidazole; azanidazole; bamnidazole; carnidazole; dimetridazole; fexinidazole; ipronidazole; "MCA"

nitroimidazole; 5-nitromegazol; "MF" nitroimidazole; nimorazole; ornidazole; panidazole; ronidazole; secnidazole; sulphimidazole; ternidazole, tinidazole, and acceptable salts thereof and a berberine alkaloid or salts thereof, wherein the 5-nitroimidazole and the berberine alkaloid are in a weight ratio of between 1:10 and 10:1 by dosage.

2. The method according to claim 1, wherein the 5-nitroimidazole is metronidazole.

3. The method according to claim 1, wherein the mammal is a pig.

4. The method according to claim 1, wherein the mammal is human.

5. The method according to claim 1, wherein the infectious disease is diarrhoea or colitis.

6. The method according to claim 1 wherein the ratio of 5-nitroimidazole:berberine alkaloid is: 1:10; 1:9; 1:8; 1:7; 1:6; 1:5; 1:4; 1:3; 1:2; 1:1; 2:1; 3:1; 4:1; 5:1; 6:1; 7:1; 8:1; 9:1 or 10:1.

7. The method according to claim 6, wherein the berberine alkaloid is selected from berberine chloride, berberine iodide or berberine sulfate.

8. The method according to claim 6 wherein the ratio of 5-nitroimidazole:berberine alkaloid is: 1:1.

9. The method according to claim 6 wherein the ratio of 5-nitroimidazole:berberine alkaloid is 1:2.

* * * * *